(12) United States Patent
Ji et al.

(10) Patent No.: US 11,007,250 B2
(45) Date of Patent: May 18, 2021

(54) METHODS AND KITS FOR TREATING PAIN

(71) Applicant: Duke University, Durham, NC (US)

(72) Inventors: Ru-Rong Ji, Durham, NC (US); Gang Chen, Durham, NC (US); Zilong Wang, Durham, NC (US); Changyu Jiang, Durham, NC (US); Kaiyuan Wang, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/612,909

(22) PCT Filed: May 12, 2018

(86) PCT No.: PCT/US2018/032475
§ 371 (c)(1),
(2) Date: Nov. 12, 2019

(87) PCT Pub. No.: WO2018/209329
PCT Pub. Date: Nov. 15, 2018

(65) Prior Publication Data
US 2020/0078443 A1 Mar. 12, 2020

Related U.S. Application Data

(60) Provisional application No. 62/505,226, filed on May 12, 2017.

(51) Int. Cl.
  *A61K 38/17* (2006.01)
  *A61K 31/485* (2006.01)
  *A61P 25/04* (2006.01)
  *A61B 5/00* (2006.01)
  *C07K 16/28* (2006.01)

(52) U.S. Cl.
  CPC ........ *A61K 38/1774* (2013.01); *A61B 5/4824* (2013.01); *A61B 5/4848* (2013.01); *A61K 31/485* (2013.01); *A61P 25/04* (2018.01); *C07K 16/2818* (2013.01); *C07K 16/2827* (2013.01); *C07K 2317/76* (2013.01)

(58) Field of Classification Search
  None
  See application file for complete search history.

(56) References Cited

U.S. PATENT DOCUMENTS

2011/0245708 A1  10/2011  Finkel et al.
2014/0242077 A1*  8/2014  Choi .................. C07K 16/2809
                                                        424/136.1
2016/0220636 A1   8/2016  Bacus et al.

FOREIGN PATENT DOCUMENTS

WO    WO2017069291 A1    4/2017

OTHER PUBLICATIONS

Chen et al., PD-L1 inhibits acute and chronic pain by suppressing nociceptive neuron activity via PD-1, Jul. 2017, Nature Neuroscience 20(7):917-926 (Year: 2017).*

Clohisy et al. Bone cancer pain. Cancer. Feb. 1, 2003, vol. 97, Supplement 3, 866-873.
Grace et al. Peripheral immune contributions to the maintenance of central glial activation underlying neuropathic pain. Brain, Behavior and Immunity. Apr. 7, 2011, vol. 25, 1322-1332.
Acosta, C, et al. TREK2 Expressed Selectively in IB4-Binding C-Fiber Nociceptors Hyperpolarizes Their Membrane Potentials and Limits Spontaneous Pain. J Neurosci, 2014, 34:1494-1509.
Ansell, SM, et al. PD-1 Blockade with Nivolumab in Relapsed or Refractory Hodgkin's Lymphoma. N.Engl.J.Med., 2015, 372:311-319.
Basbaum, AI, et al. Cellular and Molecular Mechanisms of Pain. Cell, 2009, 139:267-284.
Bennett, DL & Woods, CG. Painful and painless channelopathies. Lancet Neurol, 2014, 13:587-599.
Berta, T, et al. Extracellular caspase-6 drives murine inflammatory pain via microglial TNF-α secretion. J Clin Invest, 2014, 124:1173-1186.
Brahmer, JR, et al. Nivolumab: targeting PD-1 to bolster antitumor immunity. Future Oncol, 2015, 11:1307-1326.
Brahmer, JR, et al. Safety and Activity of Anti-PD-L1 Antibody in Patients with Advanced Cancer. N.Engl.J.Med., 2012, 366:2455-2465.
Braz, J., et al. Transmitting paint and itch messages: A contemporary view of the spinal cord circuits that generate Gate Control. Neuron, 2014, 82:522-536.
Butte, MJ, et al. PD-L1 interacts specifically with B7-1 to inhibit T cell proliferation. Immunity, 2007, 27:111-122.
Cain DM, et al. Functional Interactions between Tumor and Peripheral Nerve: Changes in Excitability and Morphology of Primary Afferent Fibers in a Murine Model of Cancer Pain. J Neurosci, 2001, 21:9367-9376.
Chen, G, et al. Intrathecal bone marrow stromal cells inhibit neuropathic pain via TGF-β secretion. J Clin Invest, 2015, 125:3226-3240.
Day, CL, et al. PD-1 expression on HIV-specific T cells is associated with T-cell exhaustion and disease progression. Nature, 2006, 443:350-354.
Devor, M, et al. Systemic lidocaine silences ectopic neuroma and DRG discharge without blocking nerve conduction. Pain, 1992, 48:261-268.
Fessas P et al. A molecularandpreclinicalcomparisonofthePD-1-targetedT-cell checkpoint inhibitors nivolumab and pembrolizumab. Seminars in Oncology, 2017, 44: 136-140.
Grace, PM, et al. Pathological pain and the neuroimmune interface. Nat Rev Immunol, 2014, 14(4): 217-231.
Guan, Z, et al. Injured sensory neuron-derived CSF1 induces microglial proliferation and DAP12-dependent pain. Nat Neurosci, 2016, 19:94-101.

(Continued)

Primary Examiner — John D Ulm
(74) Attorney, Agent, or Firm — Polsinelli PC; Michelle L. McMullen; J. Wendy Davis

(57) ABSTRACT

The present disclosure provides methods and kits for treating pain. More particularly, the present disclosure relates to methods of using PD-L1/PD-1-associated compounds to treat pain and/or bone destruction from bone cancer, and associated kits. The present disclosure also provides methods to assess the efficacy of compounds to suppress PD-1-associated nociceptive neuron activity.

11 Claims, 30 Drawing Sheets

Specification includes a Sequence Listing.

(56) References Cited

OTHER PUBLICATIONS

Hamanishi, J., et al. Safety and Antitumor Activity of Anti-PD-1 Antibody, Nivolumab, in Patients with Platinum-Resistant Ovarian Cancer. J.Clin.Oncol., 2015, 33: 4015-4022.

Hebeisen, M, et al. SHP-1 phosphatase activity counteracts increased T cell receptor affinity. J Clin Invest, 2013, 123:1044-1056.

Herbst, RS, et al. Predictive correlates of response to the anti-PD-L1 antibody MPDL3280A in cancer patients. Nature, 2014, 515: 563-567.

Honore P, et al. Osteoprotegerin blocks bone cancer-induced skeletal destruction, skeletal pain and pain-related neurochemical reorganization of the spinal cord. Nature Medicine, 2000, 6(5): 521-528.

Hucho, T & Levine, JD. Signaling pathways in sensitization: toward a nociceptor cell biology. Neuron, 2007, 55: 365-376.

Ji, RR, et al. Emerging targets in neuroinflammation-driven chronic pain. Nat Rev Drug Discov., 2014, 13:533-548.

Ji, RR, et al. Pain regulation by non-neuronal cells and inflammation. Science, 2016, 354: 572-577.

Jimenez-Andrade, JM, et al. Preventive or late administration of anti-NGF therapy attenuates tumor-induced nerve sprouting, neuroma formation, and cancer pain. Pain, 2011, 152: 2564-2574.

Keir, ME, et al. PD-1 and its ligands in tolerance and immunity. Annu.Rev.Immunol., 2008, 26: 677-704.

Kleffel, S, et al. Melanoma Cell-Intrinsic PD-1 Receptor Functions Promote Tumor Growth. Cell, 2015, 162:1242-1256.

Li, Y, et al. Toll-like receptor 4 signaling contributes to Paclitaxel-induced peripheral neuropathy. J Pain. 2014, 15:712-725.

Mogil, JS. Animal models of pain: progress and challenges. Nat Rev Neurosci, 2009, 10:283-294.

Mantyh, PW. Cancer pain and its impact on diagnosis, survival and quality of life. Nat.Rev.Neurosci, 2006,7:797-809.

Mantyh, PW. Bone cancer pain: Causes, consequences, and therapeutic opportunities. Pain, 2013, 154 Suppl 1, S54-S62.

McMahon, SB, et al. Crosstalk between the nociceptive and immune systems in host defence and disease. Nat Rev Neurosci, 2015, 16:389-402.

Negin, BP, et al. Symptoms and signs of primary melanoma: important indicators of Breslow depth. Cancer, 2003, 98:344-348.

Park, CK, et al. Extracellular microRNAs activate nociceptor neurons to elicit pain via TLR7 and TRPA1. Neuron, 2014, 82:47-54.

Patel, SP & Kurzrock, R. PD-L1 Expression as a Predictive Biomarker in Cancer Immunotherapy. Mol Cancer Ther, 2015, 14:847-856.

Postow, MA, et al. Nivolumab and Ipilimumab versus Ipilimumab in Untreated Melanoma. N.Engl.J.Med, 2015, 372:2006-2017.

Reichling, DB & Levine, JD. Critical role of nociceptor plasticity in chronic pain. Trends Neurosci, 2009, 32:611-618.

Schmidt, BL. The neurobiology of cancer pain. Neuroscientist, 2014, 20:546-562.

Scholz, J. & Woolf, CJ. The neuropathic pain triad: neurons, immune cells and glia. Nat.Neurosci, 2007, 10:1361-1368.

Schweizerhof, M, et al. Hematopoietic colony-stimulating factors mediate tumor-nerve interactions and bone cancer pain. Nat.Med., 2009, 15:802-807.

Selvaraj, D, et al. A Functional Role for VEGFR1 Expressed in Peripheral Sensory Neurons in Cancer Pain. Cancer Cell, 2015, 27:780-796.

Sharma, P & Allison, JP. The future of immune checkpoint therapy. Science, 2015, 348:56-61.

Sorge, RE, et al. Different immune cells mediate mechanical pain hypersensitivity in male and female mice. Nat Neurosci, 2015, 18:1081-1083.

Talbot, S, et al. Neuroimmunity: Physiology and Pathology. Annu Rev Immunol, 2016, 34:421-447.

Todd, AJ. Neuronal circuitry for pain processing in the dorsal horn. Nat Rev Neurosci, 2010, 11 :823-836.

Topalian, SL, et al. Safety, Activity, and Immune Correlates of Anti-PD-1 Antibody in Cancer. N.Engl.J.Med., 2012, 366:2443-2454.

Uceyler, N, et al. Deficiency of the negative immune regulator B7-H1 enhances inflammation and neuropathic pain after chronic constriction injury of mouse sciatic nerve. Exp. Neurol., 2010, 222:153-160.

Weber, JS, et al. Nivolumab versus chemotherapy in patients with advanced melanoma who progressed after anti-CTLA-4 treatment (CheckMate 037): a randomised, controlled, open-label, phase 3 trial. Lancet Oncol., 2015, 16:375-384.

Woolf, CJ. Overcoming obstacles to developing new analgesics. Nat Med, 2010, 16:1241-1247.

Xu, ZZ, et al. Inhibition of mechanical allodynia in neuropathic pain by TLR5-mediated A-fiber blockade. Nat. Med., 21: 1326-1331.

Yang, Y, et al. Delayed Activation of Spinal Microglia Contributes to the Maintenance of Bone Cancer Pain in Female Wistar Rats via P2X7 Receptor and IL-18. J. Neurosci., 2015, 35:7950-7963.

Zhang F, et al. Structural basis of the therapeutic anti-PD-L1 antibody atezolizumab. Oncotarget, 2017, 8: 90215-90224.

* cited by examiner

Human DRG and spinal nerve sections

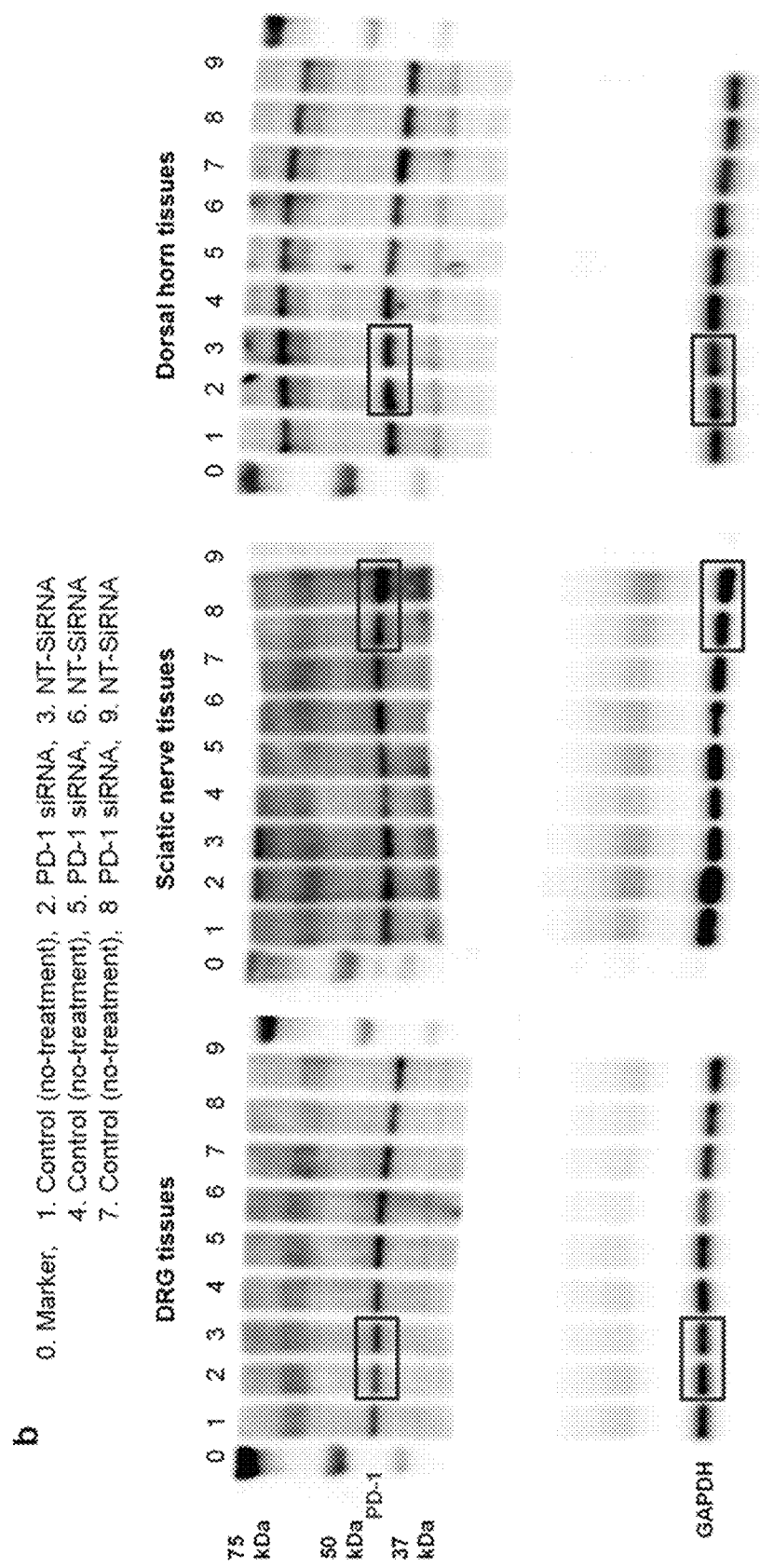

A

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Mus musculus TNF forward primer

<400> SEQUENCE: 1
ccccaaaggg atgagaagtt                                               20

<210> SEQ ID NO 2
<211> LENGTH: 20
<212> TYPE: DNA
<213> ORGANISM: Artificial Sequence
<220> FEATURE:
<223> OTHER INFORMATION: Mus musculus TNF reverse primer

<400> SEQUENCE: 2
cacttggtgg tttgctacga                                               20

<210> SEQ ID NO 3
<211> LENGTH: 20
<212> TYPE: DNA
<213> ORGANISM: Artificial Sequence
<220> FEATURE:
<223> OTHER INFORMATION: Mus musculus IL-1B forward primer

<400> SEQUENCE: 3
tgtcttggcc gaggactaag                                               20

<210> SEQ ID NO 4
<211> LENGTH: 21
<212> TYPE: DNA
<213> ORGANISM: Artificial Sequence
<220> FEATURE:
<223> OTHER INFORMATION: Mus musculus IL-1B reverse primer

<400> SEQUENCE: 4
tgggctggac tgtttctaat g                                             21

<210> SEQ ID NO 5
<211> LENGTH: 21
<212> TYPE: DNA
<213> ORGANISM: Artificial Sequence
<220> FEATURE:
<223> OTHER INFORMATION: Mus musculus IL-6 forward primer

<400> SEQUENCE: 5
tccatccagt tgccttcttg g                                             21
```

```
<210> SEQ ID NO 6
<211> LENGTH: 22
<212> TYPE: DNA
<213> ORGANISM: Artificial Sequence
<220> FEATURE:
<223> OTHER INFORMATION: Mus musculus IL-6 reverse primer

<400> SEQUENCE: 6
ccacgatttc ccagagaaca tg                                              22

<210> SEQ ID NO 7
<211> LENGTH: 22
<212> TYPE: DNA
<213> ORGANISM: Artificial Sequence
<220> FEATURE:
<223> OTHER INFORMATION: Mus musculus IFNG forward primer

<400> SEQUENCE: 7
cctagctctg agacaatgaa cg                                              22

<210> SEQ ID NO 8
<211> LENGTH: 22
<212> TYPE: DNA
<213> ORGANISM: Artificial Sequence
<220> FEATURE:
<223> OTHER INFORMATION: Mus musculus IFNG reverse primer

<400> SEQUENCE: 8
ttccacatct atgccacttg ag                                              22

<210> SEQ ID NO 9
<211> LENGTH: 20
<212> TYPE: DNA
<213> ORGANISM: Artificial Sequence
<220> FEATURE:
<223> OTHER INFORMATION: Mus musculus CCL2 forward primer

<400> SEQUENCE: 9
cccaatgagt aggctggaga                                                 20

<210> SEQ ID NO 10
<211> LENGTH: 20
<212> TYPE: DNA
<213> ORGANISM: Artificial Sequence
<220> FEATURE:
<223> OTHER INFORMATION: Mus musculus CCL2 reverse primer

<400> SEQUENCE: 10
aaaatggatc cacaccttgc                                                 20

<210> SEQ ID NO 11
<211> LENGTH: 20
<212> TYPE: DNA
<213> ORGANISM: Artificial Sequence
<220> FEATURE:
<223> OTHER INFORMATION: Mus musculus CD2 forward primer

<400> SEQUENCE: 11
cacaggtcag ggttgtgttg                                                 20

<210> SEQ ID NO 12
<211> LENGTH: 20
<212> TYPE: DNA
<213> ORGANISM: Artificial Sequence
<220> FEATURE:
<223> OTHER INFORMATION: Mus musculus CD2 reverse primer
```

-continued

```
<400> SEQUENCE: 12
aatgggatga ctaggctgga                                                    20

<210> SEQ ID NO 13
<211> LENGTH: 19
<212> TYPE: DNA
<213> ORGANISM: Artificial Sequence
<220> FEATURE:
<223> OTHER INFORMATION: Mus musculus CD8 forward primer

<400> SEQUENCE: 13
ccgttgaccc gctttctgt                                                     19

<210> SEQ ID NO 14
<211> LENGTH: 21
<212> TYPE: DNA
<213> ORGANISM: Artificial Sequence
<220> FEATURE:
<223> OTHER INFORMATION: Mus musculus CD8 reverse primer

<400> SEQUENCE: 14
ttcggcgtcc attttctttg g                                                  21

<210> SEQ ID NO 15
<211> LENGTH: 20
<212> TYPE: DNA
<213> ORGANISM: Artificial Sequence
<220> FEATURE:
<223> OTHER INFORMATION: Homo sapiens CD68 forward primer

<400> SEQUENCE: 15
accgccatgt agtccaggta                                                    20

<210> SEQ ID NO 16
<211> LENGTH: 20
<212> TYPE: DNA
<213> ORGANISM: Artificial Sequence
<220> FEATURE:
<223> OTHER INFORMATION: Homo sapiens CD68 reverse primer

<400> SEQUENCE: 16
atccccacct gtctctctca                                                    20

<210> SEQ ID NO 17
<211> LENGTH: 21
<212> TYPE: DNA
<213> ORGANISM: Artificial Sequence
<220> FEATURE:
<223> OTHER INFORMATION: Mus musculus GAPDH forward primer

<400> SEQUENCE: 17
tccatgacaa ctttggcatt g                                                  21

<210> SEQ ID NO 18
<211> LENGTH: 21
<212> TYPE: DNA
<213> ORGANISM: Artificial Sequence
<220> FEATURE:
<223> OTHER INFORMATION: Mus musculus GAPDH reverse primer

<400> SEQUENCE: 18
cagtcttctg ggtggcagtg a                                                  21
```

METHODS AND KITS FOR TREATING PAIN

CROSS-REFERENCE TO RELATED APPLICATIONS

This application is a U.S. national phase application of International Patent Application No. PCT/US2018/032475, filed on May 12, 2018, which claims the benefit of the filing date of U.S. provisional application No. 62/505,226, filed May 12, 2017, both of which are incorporated herein by reference in their entirety.

FEDERAL FUNDING STATEMENT

This invention was made with Government support under Federal Grant Nos.: R01 DE17794 and R01 NS87988, awarded by the NIH. The Government has certain rights to this invention.

BACKGROUND OF THE INVENTION

Field of the Invention

The present disclosure provides methods and kits for treating pain. More particularly, the present disclosure relates to methods of using PD-L1/PD-1-associated compounds to treat pain and/or bone destruction from bone cancer, and associated kits.

Description of the Related Art

Chronic pain is a major health problem, affecting 30% Americans, and costs US economy USD 625 billion every year. Current treatments are only partially effective and cause significant side effects (e.g., addiction by opioids). There is an urgent demand for effective and safe pain medicine.

Cancer pain dramatically impairs the quality of life in patients. Breast, lung, and prostate cancers frequently metastasize to multiple bones and cause bone cancer pain, by releasing algogenic substances. These substances include protons, bradykinin, endothelins, prostaglandins, proteases, and growth factors such as nerve growth factor (NGF) and vascular endothelial growth factor (VEGF) (Mantyh, P W. *Nat. Rev. Neurosci*, 2006, 7:797-809; Manthy, P. *Pain*, 2013, 154 Suppl 1, S54-S62; Selvaraj, D, et al. *Cancer Cell*, 2015, 27:780-796; Jimenez-Andrade, J M, et al. *Pain*, 2011, 152: 2564-2574) that can interact with peripheral nerve and cause increased hypersensitivity and excitability of nociceptive neurons (Selvaraj, D, et al. 2015; Cain D M, et al. *J Neurosci*, 2001, 21:9367-9376; Schweizerhof, M, et al. *Nat. Med.*, 2009, 15:802-807), NGF and VEGF also induce outgrowth of pain-conducting nerve fibers in cancer affected areas (Selvaraj, D, et al. 2015; Jimenez-Andrade, J M, et al. 2011). Despite current focus on cancer-produced pronocicepetive mediators (Schmidt, B L. *Neuroscienist*, 2014, 20:546-562), early-stage cancers before metastasis to bone tissues are often not painful (Manthy, P. 2013; Brahmer, J R, et al. *N. Engl. J. Med.*, 2012, 366:2455-2465) and pain in melanoma is not common prior to metastasis (Negin, B P, et al. *Cancer*, 2003, 98:344-348). It is conceivable that different cancers and even the same cancers at different growth stages may produce different pain mediators that can differentially regulate pain sensitivity via positive or negative modulation (Ji, R R, et al. *Science*, 2016, 354:572-577).

Mounting evidences suggests that cancers, such as melanoma, express the checkpoint inhibitory protein PD-L1 (programmed cell death protein 1, ligand 1), which can suppress T cell function and induce immune tolerance via its receptor PD-1 (programmed cell death protein 1) (Sharma, P & Allison, J P. *Science*, 2015, 348:56-61; Butte, M J, et al. *Immunity*, 2007, 27:111-122; Keir, M E, et al. *Annu. Rev. immunol.*, 2008, 26:677-704; Day, C L, et al. *Nature*, 2006, 443:350-354). Emerging immune therapy such as anti-PD1 and anti-PD-L1 treatments have shown success in treating cancers such as melanoma (Schmidt, B L. 2014; Herbst, R S, et al. *Nature*, 2014, 515:563-567; Topalian, S L, et al. *N. Engl. J. Med.*, 2012, 366:2443-2454), as well as lymphoma, lung cancer, ovarian cancer, and head and neck cancers (Ansell, S M, et al. *N. Engl. J. Med.*, 2015, 372:311-319; Hamanishi, J., et al. *J. Clin. Oncol.*, 2015; Postow, M A, et al. *N. Engl. J. Med*, 2015, 372:2006-2017). The global immunotherapy drug market is projected to reach USD 200 billion by 2021.

SUMMARY OF THE INVENTION

We observed that only a portion of patients respond to pain therapies and that current options for treating and managing pain are limited in effectiveness and fraught with significant side effects, particularly opioid addiction. Thus, we recognized that there is an urgent need for effective treatments of pain and the ability to predict efficacy of treatments. PD-L1 therapies are safe non-narcotic alternatives which have the potential to be more effective in managing acute and chronic pain. It is against the above background that the present invention provides certain advantages and advancements over the prior art.

Although this invention as disclosed herein is not limited to specific advantages or functionality, in one aspect the present disclosure comprises a method of treating a subject suffering from pain comprising administering to the subject a therapeutically effective amount of a compound capable of suppressing PD-1-associated nociceptive neuron activity such that the pain is treated.

In another aspect, the present disclosure comprises A method of determining the efficacy of PD-1-associated nociceptive neuron activity suppression in a subject comprising: administering to the subject a therapeutically effective amount of a compound capable of suppressing PD-1-associated nociceptive neuron activity; and conducting one or more quantitative sensory test(s) on the subject, wherein the one or more quantitative sensory test(s) is administered immediately after administration of the compound, and wherein a rapid change in mechanical pain sensitivity within a time period after administration of the compound indicates target engagement and efficacy of the therapy.

In another aspect, the present disclosure comprises a method of treating pain in a subject suffering from bone cancer pain comprising administering to the subject a therapeutically effective amount of an anti-PD-1 compound.

In another aspect, the present disclosure comprises a kit for the treatment of pain in a subject comprising a therapeutically effective amount of a compound capable of suppressing PD-1-associated nociceptive neuron activity, an apparatus for administering said compound, and instructions for use.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 3A(a)-(f): (a-d) provide In situ hybridization (ISH) images showing Pd1 mRNA expression in DRG of wild-type (WT) not Pd1 knockout (Pd1$^{-/-}$) mice. Specifically, (a) provides low magnification image of ISH with anti-sense probe showing Pd1 mRNA in DRG neurons of WT mice. Scale, 50 μm; (b) provides high magnification image of double ISH (red) and Nissl staining (green) in DRG sections. Scale, 20 μm; (c) ISH image showing loss of Pd1 mRNA expression in DRG neurons in Pd1$^{-/-}$ mice. Scale, 50 μm; (d) ISH image of sense control probe. Scale, 50 μm. (e) Left, image of immunostaining showing PD-1 expression in mouse DRG neurons. Middle, PD-1 expression lost in Pd1$^{-/-}$ mice. Right, absence of PD-1 immunostaining by treatment of a blocking peptide. Blue DAPI staining shows cell nuclei in DRG sections. Scale, 50 μm. (f) Size frequency distribution of PD-1-positive and total neurons in mouse DRGs. A total of 1555 neurons from 4 WT mice were analyzed. FIG. 3B(g)-(i):_(g,h) Double staining of PD-1 and NF200 in DRG (g) and sciatic nerve (h) sections of mice. Scales, 50 μm. (i) Double immunostaining of PD-1 and CGRP in mouse sciatic nerve. Scale, 50 μm. Arrows in g-i indicate the double-labeled neurons and axons.

FIG. 8A(a)-(f): (a) Tumor growth after melanoma cell inoculation (MCI) in hindpaw. Left, images of ipsilateral hindpaw (red arrow) and contralateral hindpaw and an isolated melanoma (top) at MCI-4w. Scales, 5 mm. Right, time course of tumor growth after MCI. BL, baseline. *P<0.05, vs. BL, One-Way ANOVA, n=25 mice/group. (b) Serum PD-L1 levels in sham control mice and melanoma-bearing mice (MCI-4w). *P<0.05, two-tailed Student's t-test. n=6 mice/group. (c,d) Time course of mechanical pain (c) and spontaneous pain (duration of licking/flinching, d) after MCI. n=21 and 25 mice/group. (e) Induction of spontaneous pain by soluble PD-1 (sPD-1) following i.pl. injection at MCI-4w. *P<0.05, compared with vehicle, two-tailed Student's t-test. n=6 and 7 mic/group. (f) Induction of ongoing pain (CPP) in melanoma-bearing mice by sPD-1 (i.pl.). Left, paradigm for assessing CPP in two-chamber test. Right, difference in time spent in drug-paired compartment between pre-conditioning and post-conditioning phases. *P<0.05, two-tailed Student's t-test, n=7-8 mice/group.

FIG. 1). PD-L1 secretion in melanoma cells and Pdl1 miRNA expression in mouse DRG neurons. (a) ELISA analysis showing PD-L1 secretion in culture medium collected from B16F10 mouse melanoma cell line or control medium (without cells). 1~1.5×10$^6$ cells were included per well. *P<0.05, two-tailed student t-test, n=3 cultures. Data are mean±s.e.m. (b,c) In situ hybridization (ISH) image showing Pdl1 mRNA expression in mouse DRG neurons. (b) Left and middle panels, low and high magnification images of ISH with anti-sense probe. Scales, 50 and 20 µm. Right, high magnification image of double ISH and Nissl staining in mouse DRG neurons. Scale, 20 µm. (c) ISH image of sense probe showing absence of Pdl1 mRNA expression in mouse DRG neurons. Scale, 50 µm.

FIG. 2). Spontaneous pain and mechanical sensitivity in nave mice and Nivolumab binding in mouse DRG neurons and sciatic nerve. (a) Soluble PD-1 (sPD-1, 5 µg, i.pl.) does not induce spontaneous pain. n.s., not significant; n=5 mice/group. (b) Prevention of PD-L1 (5 µg, i.pl.) induced analgesia (increase in paw withdrawal threshold) by pretreatment of RMP1-14 (mouse anti-PD-1 antibody, 5 µg, i.pl.) or Nivolumab (human anti-PD-1 antibody, 10 µg, i.pl.). Human IgG included as a control. *P<0.05, vs. human IgG/PD-L1, repeated measures Two-Way ANOVA, n=4 mice/group. Arrows indicate drug injections. Human IgG or monoclonal antibody injected 30 min prior to injection of PD-L1. BL, baseline. (c) Nivolumab (10 mg/ml) binds DRG neurons and sciatic nerve axons in VVT but not PdI KO mice. Nivolumab is detected by 2$^{nd}$ antibody (mouse monoclonal HP6025 Anti-Human IgG4, FITC; 1.25 mg/ml). Arrows indicate nerve fibers. Data are mean s.e.m.

FIG. 3). PD-L1 or anti-PD-1 treatment fails to change mechanical sensitivity in Pd1$^{-/-}$ mice. (a,b) von Frey test showing effects of PD-L1 (5 µg, i.pl.) and RMP1-14 (mouse anti-PD-1 antibody, 5 µg, i.pl.) on paw withdrawal threshold in VVT and KO mice. (a) PD-L1 increases withdrawal threshold in VVT but not KO mice. (b) RMP1-14 decreases withdrawal threshold in VVT but not KO mice. *P<0.05, #P<0.05, vs. baseline (BL), Two-Way repeated ANOVA, n=6 mice/group. Data are mean±s.e.m.

FIG. 4). Pd1$^{-1}$ mice display normal central innervations in the spinal cord dorsal horn. (a) Immunostaining of IB4, CGRP and NF200 on L4-spinal cord sections from VVT or Pd1$^{-/-}$ mice. Scale bar, 100 µm. (b) Nissl staining on L4-spinal cord sections of KO mice. Scale bar, 100 µm. (c) Quantification of immunofluorescence of IB4, CGRP, and NF200 staining in dorsal horn of WT and KO mice. n.s., not significant; Two-tailed Student's t-test, n=4 mice/group. Three to five sections from each animal included for quantification. Data are mean±s.e.m.

FIG. 5). Pd1$^{-1}$ mice display normal distribution patterns of C-fiber and A-fiber neurons and have no neuronal loss in DRGs. (a) Immunostaining of IB4, CGRP and NF200 and Nissl staining on L4-DRG sections from WT or Pd1$^{-/-}$ mice. Scale bar, 100 µm. (b, c) Quantification of percentages of IB4-binding, CGRP-IR, and NF200-IR neurons (b) and total numbers of neurons with Nissl staining (c) in DRG sections from WT and Pd1$^{-/-}$ mice. All the DRG sections (14 µm) were collected and every 5th section was used for respective immunostaining or Nissl staining. n=4 mice/group. n.s., not significant; Two-tailed Student's t-test. Data are mean±s.e.m.

FIG. 6). Spinal application of PD-L1 suppresses excitatory synaptic transmission in lamina 110 neurons in spinal cord slices and inhibits neuropathic pain and baseline pain in mice. (a-d) Patch clamp recordings of excitatory synaptic transmission and quantification of frequency and amplitude of spontaneous excitatory postsynaptic synaptic currents (sEPSCs) in lamina 110 neurons of spinal cord slices of nave mice. (a) Perfusion of sEPSCs with PD-L1 (30 ng/ml). Left, traces of sEPSCs before (1) and after (2) PD-L1 perfusion. Right, frequency (upper) and amplitude (bottom) of sEPSCs. *P<0.05, before vs. after treatment, paired two-tailed Student's t-test, n=14 neurons/ 3-4 mice. (b) Perfusion of sEPSCs with sPD-1 (30 ng/ml). *P<0.05, compared with control, n.s., no significance, paired two-tailed Student's t-test, n=9 neurons/3 mice. (c) Incubation of spinal cord slices with Nivolumab (300 ng/ml, 3 h). *P<0.05, One-way ANOVA, followed by Bonferroni's post-hoc test, n=21 neurons/3-4 mice. (d) Incubation with Nivolumab (300 ng/ml, 3 h) blocks the effects of PD-L1. n.s., no significance; n=6 neurons/3 mice. The data are mean±s.e.m.

FIG. 7). Spinal application of PD-L1 inhibits mechanical hypersensitivity and firing of spinal WDR neurons in a model of bone cancer in rats. (a) Inhibition of bone cancer-induced mechanical allodynia by i.t. PD-L1 in rats. *P<0.05, vs. baseline (BL), § F<0.05, vs. pre-injection baseline on post-tumor implantation day 14 (PTD 14), #P<0.05, vs. vehicle, repeated measures Two-Way ANOVA, n=5 rats/group. Arrow indicates drug injection. (b,c) Suppression of brush, von Frey filaments, and pinch evoked spikes of spinal WDR neurons by PD-L1 (20 µg, i.t., 3 h) on post-tumor implantation day 14. (b) Histograms of evoked spikes of WDR neuron firing by brush, von Frey filaments, and pinch stimulation. (c) Mean spikes of WDR neurons following low and high intensity mechanical stimuli. *P<0.05, vs. vehicle control, student t-test, n=5 rats/group. (d,e) Enhancement of brush, von Frey filaments, and pinch evoked spikes of WDR neurons by intrathecal Nivolumab (10 µg, 1 h) on post-tumor implantation day 8. (d) Histograms of evoked spikes of WDR neurons firing by brush, von Frey filaments, and pinch stimulation. (e) Mean spikes of WDR neurons following low and high intensity mechanical stimuli. *P<0.05, vs. vehicle; #P<0.05 vs. human IgG, One-Way ANOVA, n=4-5 rats/group. Data are mean±s.e.m.

FIG. 8). PD-L1 induces phosphorylation of SHP1 in mouse DRG neurons. (a) Double IHC and ISH staining shows co-localization of pSHP-1 and Pd1 mRNA in DRG neurons 30 min after intrathecal PD-L1 injection (1 µg). Scale, 50 µm. (b) Enlarged images of boxes in a. Arrows indicate double-labeled neurons. Scale, 20 µm. (c) PD-L1 treatment (10 ng/ml, 30 min) increases phosphorylation of SHP-1 (pSHP-1) in dissociated mouse DRG neurons. Left, pSHP-1 immunostaining and effects of PD-L1 and the SHP-1 inhibitor SSG (11 µM). Scales, 50 µm. Right, intensity of immunofluorescence of pSHP-1-positive neurons. *P<0.05, n=98-104 neurons from 3 separate dishes, One-Way ANOVA, n.s., no significance. Data are mean±s.e.m.

FIG. 9). TREK2 activation by PD-L1 in CHO cells and schematic illustration of PD-L1 induced silence of nociceptive neurons. (a) TREK2 immunostaining in mouse DRG. Scale, 50 µm. (b) PD-L1 increases TREK2-mediated outward currents (up-left and up-right), causes negative shift in reversal potential ($E_{rev}$) of outward currents (low-left), and changes RMP (low-right) via PD-1. CHO cells were co-transfected with Trek2 and Pd1 cDNAs or only transfected with Trek2 or Pd1 cDNA alone. *P<0.05, One-Way ANOVA, n=6-8 cells/2 cultures. Also see FIG. 6d,e. Data are mean±s.e.m. (c) Schematic illustration of mechanisms by which PD-L1 silences nociceptive neurons.

FIG. 10). PD-1 immunofluorescence in DRG neurons and nerve axons of human tissue sections. (a,b) PD-1 immunofluorescence in human DRG neurons and dorsal root axons. Right panels in (a) and (b) showing absence of PD-1 immunostaining by blocking peptide. Blue DAPI staining shows all cell nuclei in DRG and nerve sections. Scales, 50 µm. (c) Double immunostaining of PD-1 and NF200 in human spinal nerve axons. The Box in the left panel is enlarged in three panels. Scales, 50 µm. Arrows indicate the double-labeled axon.

FIG. 11). Intraplantar (i.pl.) injection of soluble PD-1 (sPD-1) evokes spontaneous pain and mechanical allodynia in melanoma mice. (a,b) Induction of spontaneous pain (a, flinching/licking behavior) and evoked pain (b, mechanical allodynia) by soluble PD-1 (sPD-1) following i.pl. injection at MCI-4w. Arrow indicates drug injection. *P<0.05, compared with vehicle, two-tailed Student's t-test (f) and repeated measures Two-Way ANOVA (g). n=6 and 7 mice per group.

FIG. 12). Intraplantar (i.pl.) injection of soluble PD-1 (sPD1) does not change immune responses in melanoma-bearing hindpaw skins in the acute phase. sPD1 (5 µg, i.pl.), given to melanoma mice at 4w does not change immune responses in hindpaw skins at 3 h after injection. *P<0.05, vs. contralateral control (for all 8 markers), n.s., no significance (for all 8 markers), One-Way ANOVA, n=5 mice/group. All the data are expressed as mean±s.e.m.

FIG. 21A and FIG. 21B (Supp. FIG. 13). Pd1-targeting siRNA decreases PD-1 expression in DRG and sciatic nerve but not spinal cord dorsal horn tissues. FIG. 21A: (a) Western blot analysis showing effects of Pd1-targeting siRNA and non-targeting (NT) control siRNA on PD-1 expression in DRG, sciatic nerve, and spinal cord tissues. Low panels, quantification of PD-1 expression in different mouse tissues. *P<0.05, PD-1 vs. NT, n.s., no significance, two-tailed Student's t-test, n=5 mice/group. siRNA was applied via peri sciatic injection (2 µg) given at MCI-4w. FIG. 21B: (b) Uncut gels for PD-1 and GAPDH western blots of DRG, sciatic nerve, and dorsal horn tissues. The represented blots are highlighted in the red boxes, respectively. The images (flipped) show non-targeting (NT) siRNA treatment on the left and PD-1 siRNA treatment on the right.

FIG. 14). Induction of mechanical allodynia and spontaneous pain by systemic or local injection of anti-PD-1 antibodies and SHP-1 inhibitor in melanoma mice. FIG. 22A(a)-(c): (a,b) Intravenous RMP1-14 (mouse anti-PD-1 antibody, 10 mg/kg) induces mechanical allodynia (a) and spontaneous pain (b) in melanoma-bearing mice at MCI-4w. *P<0.05, compared to control rat IgG2A, Two-Way ANOVA, repeated measures (a), or Student's t-test (b), n=6 mice/group. Drug injection is indicated by arrow. (c) Intrathecal injection of Nivolumab (1 and 10 µg, n=6 and 7 mice/group), given at MCI-4w (shown with the arrow), induces mechanical allodynia. *P<0.05, compared with control human IgG4, repeated measures Two-Way ANOVA.

DETAILED DESCRIPTION OF THE INVENTION

Figure 1:
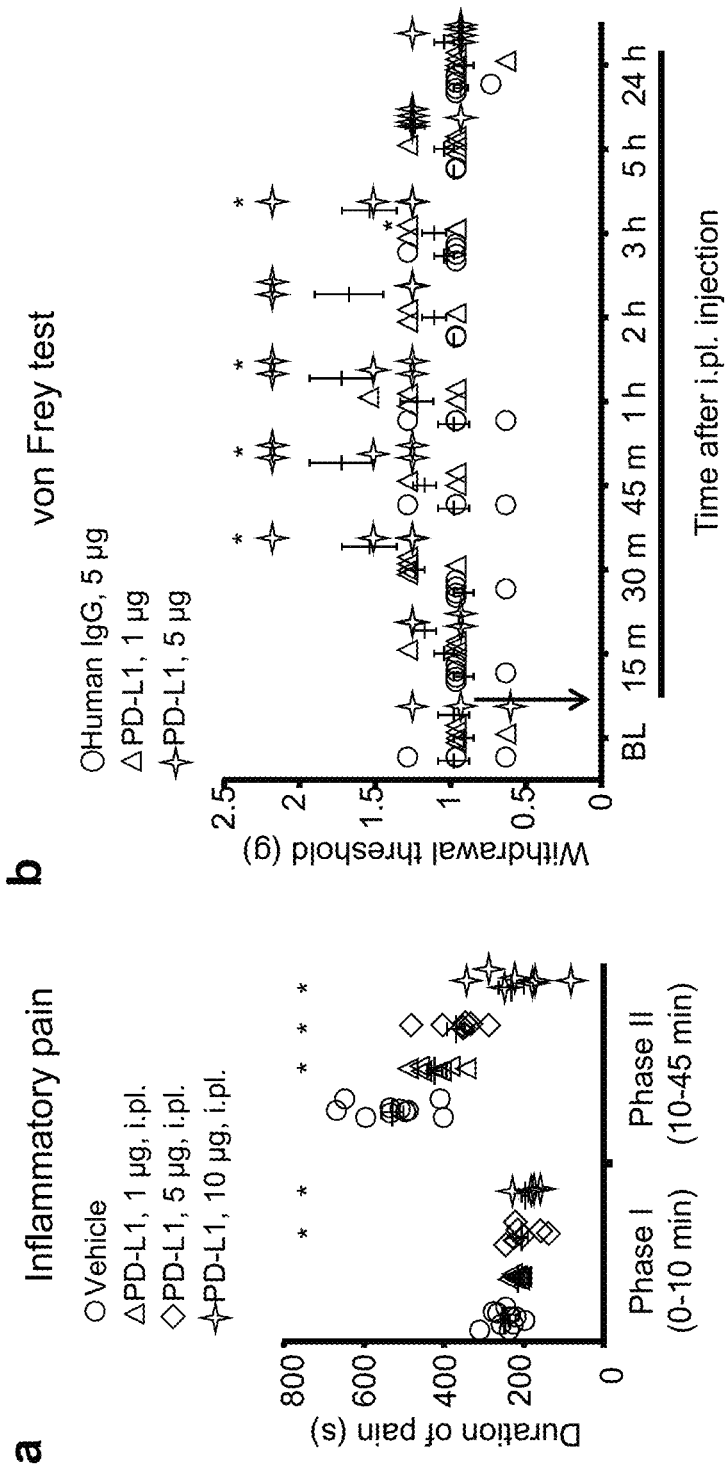
FIG. 1. Exogenous PD-L1 inhibits formalin-induced inflammatory pain and increases pain threshold in naïve mice. (a) Formalin-induced Phase-I and Phase-II inflammatory pain, measured by duration of spontaneous pain behavior (flinching/licking) every 5 min. *P<0.05, vs. vehicle (PBS), One-Way ANOVA, n=7-10 mice/group. PD-L1 was administered 30 min prior to the formalin injection. (b) Basal mechanical pain assessed in von Frey test in naïve mice. Notice an increase in paw withdrawal threshold after PD-L1 injection (1 and 5 μg, i.pl.). *P<0.05, vs. human IgG, repeated measures Two-Way ANOVA, n=5 mice/group. Arrow indicates drug injection. Data are mean±s.e.m.

Before the disclosed processes and materials are described, it is to be understood that the aspects described herein are not limited to any specific embodiment, apparatus, or configuration, and as such can, of course, vary. It is also to be understood that the terminology used herein is for the purpose of describing particular aspects only and, unless specifically defined herein, is not intended to be limiting.

It is also to be understood that unless clearly indicated otherwise by the context, embodiments disclosed for one aspect or embodiment of the invention can be used in other aspects or embodiments of the invention as well, and/or in combination with embodiments disclosed in the same or other aspects of the invention. Thus, the disclosure is intended to include, and the invention includes, such combinations, even where such combinations have not been explicitly delineated.

Definitions

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

"About" is used to provide flexibility to a numerical range endpoint by providing that a given value may be "slightly above" or "slightly below" the endpoint without affecting the desired result.

As used herein, "treatment" refers to a clinical intervention made in response to a disease, disorder or physiological condition manifested by a patient or to which a patient may be susceptible. The aim of treatment includes the alleviation of symptoms, slowing or stopping the progression or worsening of a disease, disorder, or condition and/or the remission of the disease, disorder or condition. In some embodiments, the treatment comprises pain. As used herein, the term "pain" refers to any type of pain (acute or chronic). Examples, include, but are not limited to, inflammatory pain, neuropathic pain, cancer pain, and the like. In some embodiments, the pain comprises neuropathic pain. In other embodiments, the pain comprises inflammatory pain. In yet other embodiments, the pain comprises cancer pain.

The term "effective amount" or "therapeutically effective amount" refers to an amount sufficient to effect beneficial or desirable biological and/or clinical results.

The term "biological sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, tissue, mucus and tears. In one embodiment, the biological sample is a blood sample (such as a plasma sample). A biological sample may be obtained directly from a subject (e.g., by blood or tissue sampling) or from a third party (e.g., received from an intermediary, such as a healthcare provider or lab technician).

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is suffering from pain.

The prevailing view in the field is that cancers secrete pronociceptive mediators to activate or sensitize primary afferent neurons in the cancer microenvironment. This microenvironment contains growth factors such as NGF and VEGF that cause sprouting of pain-sensing afferent fibers (Selvaraj, D, et al. 2015; Jimenez-Andrade, J M, et al. 2011). Programmed cell death ligand-1 (PD-L1) is typically produced by cancer cells and suppresses immunity through PD-1 receptor expressed on T cells. However, the role of PD-L1/PD-1 in regulating pain and neuronal function is unclear. Specifically, it is unclear whether and how the PDL1/PD-1 pathway can regulate pain sensitivity via non-immune modulation such as neuronal modulation. It is increasingly appreciated that primary nociceptive neurons (nociceptors) share similarities with immune cells and can both listen and talk to immune cells (Ji, R R, et al. 2016; Talbot, S, et al. *Annu Rev Immunol*, 2016, 34:421-447; McMahon, S B, et al. *Nat Rev Neurosci*, 2015, 16:389-402). Nociceptors not only respond to immune mediators such as cytokines and chemokines and bacterial infection (Chiu, I M, et al. *Nature*, 2013, 501:52-57) but also produce cytokines and chemokines and express Toll-like receptors (TLRs), key regulators of immunity (Talbot, S, et al. 2016; Ji, R R, et al. *Nat Rev Drug Discov.*, 2014, 13:533-548; Li, Y, et al. *J Pain.* 2014, 15:712-725; Xu, Z Z, et al. *Nat. Med.*, 2015). In primary sensory neurons, TLRs rapidly regulate pain sensitivity via interacting with ion channels (Ji, R R, et al. 2016; Park, C K, et al. *Neuron*, 2014, 82:47-54).

We have discovered that cancers also produce the antinociceptive mediator PD-L1 to suppress pain. In particular, we have found that PD-L1 is a previously unrecognized endogenous inhibitor of pain: PD-L1 is produced not only by melanoma but also by non-malignant tissues such as skin, DRG, and spinal cord. It was previously unclear whether nociceptive neurons express functional PD-1 receptor, an important immune regulator, in mouse and human dorsal root ganglion (DRG). The present inventors have assessed the expression and function of PD-1 in primary sensory neurons of mouse and human DRG and demonstrated that activation of PD-1 by PD-L1 potently suppresses neuronal activities in mouse and human nociceptive neurons. Moreover, PD-L1 inhibits acute baseline pain and inflammatory pain and chronic neuropathic pain after nerve injury. Both melanoma and normal neural tissues including dorsal root ganglia (DRG) produce PD-L1 that can potently inhibit acute and chronic pain. Intraplantar injection of PD-L1 evokes analgesia in nave mice via PD-1, whereas PD-L1 neutralization or PD-1 blockade induces mechanical allodynia. Mice lacking Pd1 exhibit thermal and mechanical hypersensitivity. PD-1 activation in DRG nociceptive neurons by PD-L1 induces SHP-1 phosphorylation, inhibits sodium channels, and causes hyperpolarization through activation of TREK2 $K^+$ channels. In addition to malignant melanoma tissue, endogenous PD-L1 can be detected in normal neural tissues including spinal cord DRG nerve and skin. The inventors also discovered that PD-L1 potently suppresses spinal cord synaptic transmission in the pain circuit as a unique neuromodulator. Finally, PD-L1 masks pain in melanoma, and conversely, blocking PD-L1 or PD-1 elicits spontaneous pain and allodynia in melanoma-bearing mice. These findings within the present disclosure identify a previously unrecognized role of PD-L1 as an endogenous pain inhibitor and a neuromodulator.

In naïve mice, exogenous application of PD-L1 induced analgesia, whereas blockade of endogenous PD-L1 and PD-1 signaling via sPD-L1, PD-1 antibodies, or Pd1 deletion resulted in hyperalgesia. PD-L1 increased pain threshold via PD-1 receptor because the analgesic effect of PD-L1 was completely lost in mice lacking Pd1. In addition to physiological pain in nave animals, PD-L1 potently suppressed formalin-induced acute inflammatory pain. Furthermore, PD-L1 effectively reduced chronic pain including nerve injury-induced neuropathic pain and bone cancer pain in rodents via both peripheral and central actions.

We have also discovered that PD-L1 modulates neuronal excitability in mouse and human DRGs of the peripheral nervous system and synaptic transmission in the spinal cord of the central nervous system through activation of PD-1 receptor. It has been generally believed that PD-1 is expressed by immune cells such as T cells (Keir, M E, et al. 2008). However, non-immune cells such as melanoma cells also express PD-1 (Kleffel, S, et al. *Cell*, 2015, 162:1242-1256). Our analyses using immunohistochemistry, in situ hybridization, and electrophysiology in dissociated DRG neurons clearly demonstrate the presence of anatomical and functional PD-1 receptor in mouse and human DRG neurons.

Figure 14:
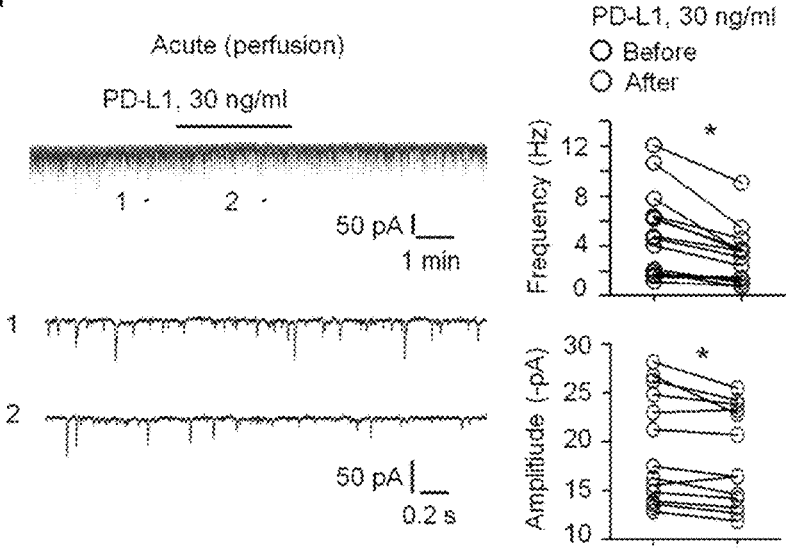
FIG. 14 (Supp.
Figure 14:
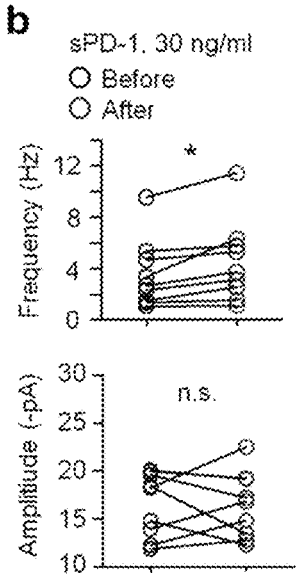
Figure 14:
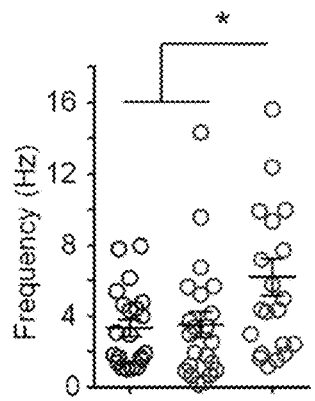
Figure 14:
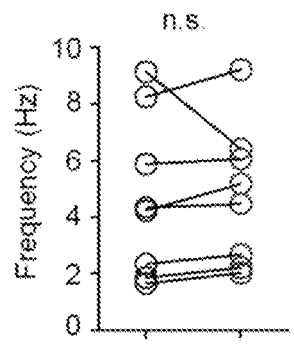

Mechanistically, our results show that activation of PD-1 by PD-L1 inhibited action potential induction and suppressed transient sodium currents in mouse and human DRG neurons. PD-L1 also regulated RMPs and caused hyperpolarization via PD-1/SHP activation and subsequent activation of two-pore $K^+$ channel TREK2. Furthermore, PD-L1 was present in spinal cord tissue and bath application of PD-L1 suppressed excitatory synaptic transmission (sEPSC) in lamina 110 neurons in the spinal cord pain circuit. PD-L1 also inhibited bone cancer-induced hyperexcitability in spinal WDR neurons. These results strongly suggest that as a neuromodulator PD-L1 modulates pain sensitivity via both peripheral and central mechanisms. Because PD-L1 affects both the frequency and amplitude of sEPSCs in spinal cord slices (FIG. 14), PD-1 may also be present in postsynaptic neurons in the spinal cord and brain. Future study is necessary to investigate signaling mechanisms by which PD-L1/PD-1 regulates synaptic transmission and synaptic plasticity in the spinal cord and brain. Given an important role of immune cells in chronic pain sensitization (Ji, R R, et al. 2016; Scholz, J. & Woolf, C J. *Nat. Neurosci*, 2007, 10:1361-1368) it is conceivable that PD-L1 could control chronic pain by suppressing T-cell activation and proinflammatory responses (Uceyler, N, et al. *Exp. Neurol.*, 2010, 222:153-160). However, given the time scale of neuromodulation (minutes and hours), the rapid changes in pain behavior after the manipulations of the PD-L1/PD-1/SHP pathway are likely to be mediated by neuronal activation. Growing evidence supports an important role of glial cells such as microglia and astrocytes in the pathogenesis of pain (Ji, R R., et al. 2016; Guan, Z, et al. *Nat Neurosci,* 2016, 19:94-101; Grace, P M, et al. *Nat Rev Immunol,* 2014; Sorge, R E, et al. *Nat Neurosci,* 2015, 18:1081-1083). We should not exclude the possibility that PD-L1/PD-1 may also regulate glial signaling in persistent pain.

It is noteworthy that we discovered that PD-L1 suppresses pathological pain not only in models of inflammatory, neuropathic, and bone cancer pain but also in a melanoma model, which exhibited high PD-L1 levels in circulation. We provided several lines of pharmacological and behavioral evidence to demonstrate a critical role of the PD-L1/PD-1 axis in masking pain in melanoma-bearing mice. First, inoculation of B16-melanoma cells resulted in robust melanoma growth but not spontaneous pain and mechanical allodynia. Second, intraplantar neutralization of PD-L1 with soluble PD-1 induced spontaneous pain, ongoing pain (CPP), and mechanical allodynia; and furthermore, systemic or local injection of either human anti-PD-1 antibody (Nivolumab) or mouse anti-PD-1 antibody (RMP1-14), or siRNA knockdown of PD-1 expression in DRGs each induced robust pain symptoms in melanoma-bearing hindpaw. Finally, inhibition of SHP also evoked spontaneous pain. It is of great interest to investigate whether PD-L1 can still mask pain after melanoma metastasis.

What is the biological significance of PD-L1 in suppressing the function of both immune system and nociceptive system? Because these two systems are important for host defense (Talbot, S, et al. 2016; McMahon, S B, et al. 2015), it is conceivable that tumor can shut off both defense systems via PD-L1 secretion for optimal host invasion and cancer growth. Emerging immune therapies with anti-PD1 and anti-PD-L1 antibodies have shown efficacy in treating cancers such as melanoma (Brahmer, J R, et al. 2012; Herbst, R S, et al. 2014; Topalian, S L, et al. 2012). Our findings suggest the importance of examining the pain caused by individual tumor sites in patients with melanoma and other malignancies before, after, and during immune therapies. On the other hand, it is also of great interest to identify novel pain inhibitors produced by cancer cells, which will open a new avenue to developing future pain medicine. Given the high potency of PD-L1 in suppressing activities of human nociceptive neurons, local targeting of PD-L1/PD-1 signaling in sensory neurons may lead to the development of novel analgesics.

In view of the present disclosure, the methods described herein can be configured by the person of ordinary skill in the art to meet the desired need. In general, the present disclosure provides methods of treating a subject suffering from pain comprising, consisting of, or consisting essentially of administering to the subject a therapeutically effective amount of a compound capable of suppressing PD-1-associated nociceptive neuron activity such that the pain is treated.

In some embodiments, the compound comprises one or more of PD-L1 and derivatives thereof, small molecular activators of PD-1, SHP-1 phosphatase activators, and combinations thereof. In some embodiments, the compound comprises PD-L1. "Derivatives" of PD-L1 are structural analogs of PD-L1 or compounds of which PD-L1 is a precursor that inhibit PD-1. In other embodiments, the compound comprises PD-L1.

The compound comprising one or more of PD-L1 and derivatives thereof, small molecular activators of PD-1, SHP-1 phosphatase activators, and combinations thereof may be administered to a subject by any technique known in the art, including local or systemic delivery. Routes of administration include, but are not limited to, subcutaneous, intravenous, intrathecal, intramuscular, epidural injection or implantation, or intranasal administration. In some embodiments, the compound is administered intrathecally (e.g., an administration into the spinal canal, or into the subarachnoid space, or into space under the arachnoid membrane of the brain) or intravenously (IV). In other embodiments, the compound is administered to the subject's skin, muscle, joint, cerebral spinal fluid (CSF) or dorsal root ganglia. In other embodiments, the subject is a human.

Said compound may be administered in a single dose or in multiple doses (e.g., two, three, or more single doses per treatment) over a time period (e.g., hours or days). Said compound may be present in a therapeutically effective concentration. In certain embodiments, the concentration of said compound is is about 0.1 nmol/L to about 1000 nmol/L at the time of administration; e.g., about 0.1 nmol/L to about 500 nmol/L, or about about 0.1 nmol/L to about 250 nmol/L, or about 0.1 nmol/L to about 100 nmol/L, or about 0.1 nmol/L to about 50 nmol/L, or about 0.1 nmol/L to about 10 nmol/L, or about 0.1 nmol/L to about 1 nmol/L, or about 1 nmol/L to about 500 nmol/L, or about 1 nmol/L to about 250 nmol/L, or about 1 nmol/L to about 100 nmol/L, or about 1 nmol/L to about 50 nmol/L, or about 1 nmol/L to about 10 nmol/L, or about 10 nmol/L to about 500 nmol/L, or about 10 nmol/L to about 250 nmol/L, or about 10 nmol/L to about 100 nmol/L, or about 10 nmol/L to about 50 nmol/L, or about 100 nmol/L to about 500 nmol/L, or about 100 nmol/L to about 250 nmol/L. One of skill in the art will recognize that suitable volume of the dose may be selected based on the desired route of administration.

Another aspect of the present disclosure provides a method of determining the efficacy of PD-1-associated nociceptive neuron activity suppression in a subject comprising, consisting of, or consisting essentially of administering to a subject a therapeutically effective amount of a compound capable of suppressing PD-1-associated nociceptive neuron activity, and conducting one or more quantitative sensory test(s) on the subject, wherein the one or more quantitative sensory test(s) is administered immediately after administration of the compound, and wherein a rapid change in mechanical pain sensitivity within a time period after administration of the compound indicates target engagement and efficacy of the therapy. In some embodiments, the compound comprises one or more of PD-L1 and derivatives thereof, small molecular activators of PD-1, SHP-1 phosphatase activators, and combinations thereof. In other embodiments, the time period after administration of said compound comprises 30 minutes, 45 minutes, 1 hour, 2 hours, 3 hours, 6 hours or 12 hours.

Another aspect of the present disclosure provides a kit for the treatment of pain in a subject comprising a therapeutically effective amount a compound capable of suppressing PD-1-associated nociceptive neuron activity, an apparatus for administrating said compound, and instructions for use. In some embodiments, the compound comprises, consists of, or consists essentially of one or more of PD-L1 and derivatives thereof, small molecular activators of PD-1, SHP-1 phosphatase activators, and combinations thereof. In some embodiments, the compound comprises PD-L1. In other embodiments, the subject is a human.

Another aspect of the present disclosure provides methods of treating a subject suffering from pain comprising administering to the subject PD-L1 and a pain reliever, wherein the PD-L1 potentiates the analgesic effect of said pain reliever. In some embodiments, administration of PD-L1 along with the pain reliever increases the effectiveness of said pain reliever. In some embodiments, administration of PD-L1 along with the pain reliever increases the likelihood that a subject will respond to the pain reliever. In some embodiments, the subject is a human. In other embodiments, the pain reliever is morphine.

Another aspect of the present disclosure provides methods of alleviating pain in a subject suffering from bone cancer pain comprising, consisting of, or consisting essentially of administering to the subject an effective amount of anti-PD-1 compound. In some embodiments, the anti-PD-1 compound is Nivolumab, Pembrolizumab, Pidilizumab (CT-011, Cure Tech), Atezolizumab (Tecentriq) or Durvalumab (Imfinzi). In some embodiments, the anti-PD-1 compound is Nivolumab. In some embodiments, the subject is a human.

Another aspect of the present disclosure provides methods of treating or slowing bone destruction in a subject suffering from bone cancer comprising, consisting of, or consisting essentially of administering to the subject an effective amount of anti-PD-1 compound. In some embodiments, the anti-PD-1 compound is Nivolumab, Pembrolizumab Pidilizumab (CT-011, Cure Tech), Atezolizumab (Tecentriq) or Durvalumab (Imfinzi). In some embodiments, the anti-PD-1 compound is Nivolumab. In some embodiments, the subject is a human.

The anti-PD-1 compound may be administered to a subject by any technique known in the art, including local or systemic delivery. Routes of administration include, but are not limited to, subcutaneous, intravenous, intrathecal, intramuscular, epidural injection or implantation, or intranasal administration. In some embodiments, the compound is administered intrathecally (e.g., an administration into the spinal canal, or into the subarachnoid space, or into space under the arachnoid membrane of the brain) or intravenously (IV). In other embodiments, the compound is administered to the subject's skin, muscle, joint, cerebral spinal fluid (CSF) or dorsal root ganglia The anti-PD-1 compound may be present in a therapeutically effective concentration. In certain embodiments, the concentration of said compound is is about 0.1 nmol/L to about 100 nmol/L at the time of administration; e.g., about 0.1 nmol/L to about 75 nmol/L, or about about 0.1 nmol/L to about 50 nmol/L, or about 0.1 nmol/L to about 25 nmol/L, or about 0.1 nmol/L to about 10 nmol/L, or about 0.1 nmol/L to about 1 nmol/L, or about 1 nmol/L to about 100 nmol/L, or about 1 nmol/L to about 75 nmol/L, or about 1 nmol/L to about 50 nmol/L, or about 1 nmol/L to about 25 nmol/L, or about 1 nmol/L to about 10 nmol/L, or about 10 nmol/L to about 100 nmol/L, or about 10 nmol/L to about 75 nmol/L, or about 10 nmol/L to about 50 nmol/L, or about 10 nmol/L to about 25 nmol/L. One of skill in the art will recognize that a suitable volume of the dose may be selected based on the desired route of administration.

The following examples are offered by way of illustration and not by way of limitation.

Examples

Materials and Methods

Reagents. Mouse PD-1 (Catalog: 1021-PD-100) and Rat IgG2A Isotype control (Catalog: MAB006) was obtained from R&D. Mouse PD-L1 (Catalog: ab180058) and human IgG4 (Catalog: ab90286) were purchased from Abcam. Nivolumab (OPDIVO®), a humanized anti-PD-1 antibody, was purchased from Bristol-Myers Squibb. Anti-mouse PD-1 antibody RMP1-14 (Catalog: BEO146) was from Bio X Cell. Mouse Pd1-targeting siRNA (Catalog: L-040330-01-0005) and non-targeting siRNA (Catalog: D-0018100-01-20) were purchased from Thermo Scientific Dharmacon. RVG peptide was synthetized by Invitrogen and mixed with siRNA to increase neuronal uptake of siRNA by axons in the sciatic nerve (Berta, T, et al. *J Clin Invest*, 2014, 124:1173-1186). SHP-1 inhibitor sodium stibogluconate (SSG) was from Calbiochem (Catalog: 567565). PD1/PDCD1 cDNA construct (SC117011, NM_005018) and TREK2/KCNK10 cDNA construct (SC110477, NM_021161) were purchased from Origene Technologies.

Animals. Adult mice (males, 8-10 weeks) were used for behavioral and biochemical studies. Pd1 knockout mice with C57BL/6 background were purchased from the Jackson laboratory (Stock No: 021157) and maintained at Duke animal facility. Young mice (5-7 weeks of both sexes) were used for electrophysiological studies in the spinal cord and DRG neurons. All mouse procedures were approved by the Institutional Animal Care & Use Committee of Duke University.

For bone cancer pain experiments, adult Wistar rats (females, 8 weeks) were obtained from Shanghai Experimental Animal Center of Chinese Academy of Sciences and the rat experiments were approved by the Animal Care and Use Committee of Fudan University. All animals were housed under a 12-hour light/dark cycle with food and water available ad libitum. No statistical method was used to predetermine sample size. No randomization was applied to the animal experiments. Sample sizes were estimated based on our previous studies for similar types of behavioral, biochemical, and electrophysiological analyses (Xu, Z Z, et al. 2015; Berta, T, et al. 2014; Chen, G, et al. *J Clin Invest*, 2015, 125:3226-3240). Two to five mice or rats were housed in each cage. Animal experiments were conducted in accordance with the National Institutes of Health Guide for the Care and Use of Laboratory Animals. The numbers of mice and rats used in different experiments were summarized in Table 1.

TABLE 1

Numbers of animals (mice and rats) used in study.

| Experiment | Sample size | No. of groups | No. of samples | No. of animals/donors |
|---|---|---|---|---|
| 1. In vivo | | | | |
| 1.1 Behavioral test (mouse) | n = 4-25 mice | 57 | 342 | 342 mice |
| Behavioral test (rat) | n = 5, 6 rats | 5 | 27 | 27 rats |
| 1.2 Tissue ELISA analysis | n = 3, 4 mouse tissues | 14 | 44 | 7 mice |
| 1.3 Serum ELISA analysis | n = 6 mice | 2 | 12 | 12 mice |

TABLE 1-continued

Numbers of animals (mice and rats) used in study.

| Experiment | Sample size | No. of groups | No. of samples | No. of animals/donors |
|---|---|---|---|---|
| 1.4 Western Blot analysis | n = 5 mice | 2 | 10 | 10 mice |
| 1.5 In situ hybridization | n = 4 mice | 5 | 20 | 15 mice |
| 1.6 Mouse tissues (IHC) | n = 4 mice | 10 | 40 | 24 mice |
| 1.7 Recording in sciatic nerve | n = 5 mice | 2 | 10 | 10 mice |
| 1.8 Recording in rat spinal cord | n = 4, 5 rats | 5 | 24 | 24 rats |
| 2. Ex vivo | | | | |
| 2.1 Patch-clamp recording in whole-mount DRGs | n = 6-18 whole-mount DRGs | 9 | 95 | 47 mice |
| 2.2 Patch-clamp recording in spinal cord slices | n = 6-22 spinal cord slices | 9 | 122 | 42 mice |
| 2.3 Human tissues (IHC) | n = 4 tissues | 6 | 4 | 4 donors |
| 3. In vitro | | | | |
| 3.1 Patch-clamp recording | | | | |
| 3.1.1 Human DRG neurons | n = 7-17 human DRG neurons | 8 | 81 | 5 donors |
| 3.1.2 Mouse DRG neurons | n = 6-9 mouse DRG neurons | 2 | 12 | 5 mice |
| 3.2 Immunocytochemistry (ICC) | n = 98-104 mouse DRG neurons | 4 | 407 | 4 mice |
| 3.3 Culture medium ELISA analysis | n = 3 cultures | 2 | 6 | Cell line |
| 3.4 Cell culture for implantation | n = 30 cultures | 1 | 30 | Cell line |
| 3.5 Cell transfection for recording | n = 6-10 cultures | 7 | 38 | Cell line |
| Total number of mice | | | | 528 |
| Total number of rats | | | | 51 |
| Total number of human donors | | | | 9 |

Culture of murine melanoma cells. Murine melanoma cell line B16-F10 was obtained from ATCC (ATCC®CRL-6475, Rockville, Md.). Melanoma cells were grown in Dulbecco's modified Eagle medium containing 4500 mg/l glucose, 100 mg/l penicillin, 100 mg/l streptomycin, and supplemented with 10% fetal bovine serum in 5% $CO_2$/95% air at 37° C. Cells were collected for experiments following enzymatic digestion with trypsin.

Mouse and rat models of cancer and pain. We produced the following rodent models of pain:

Mouse model of melanoma: Murine B16-F10 melanoma cells ($5\times10^5$ cells/20 µl, suspended in PBS) were subcutaneously injected into the plantar region of a left hindpaw of mouse.

Mouse model of inflammatory pain: Acute inflammatory pain was induced by intraplantar injection of 20 µl diluted formalin (5%).

Mouse model of neuropathic pain: Chronic constriction injury (CCI) model of neuropathic pain was produced under isoflurane anesthesia (Chen, G, et al. 2015). After the left sciatic nerve was exposed, three ligatures (7-0 prolene) were placed around the nerve proximal to the trifurcation with one millimeter between each ligature. The ligatures were loosely tied until a short flick of the ipsilateral hind limb was observed. Animals in the sham group received surgery identical to those described but without nerve ligation.

Rat bone cancer pain model. Tumor cells were extracted from the ascetic fluid of rats that received Walker 256 rat mammary gland carcinoma cells, and suspension of $1\times10^8$/ml tumor cells in PBS was prepared. The inoculation was performed as previously described (Yang, Y, et al. J. Neurosci., 2015, 35:7950-7963). Briefly, rats were anesthetized with sodium pentobarbital (50 mg/kg, intraperitoneal). The right leg was shaved, and the skin was disinfected with iodine tincture and 75% ethanol. A 22-gauge needle was inserted at the site of the intercondylar eminence of the right tibia and was then replaced with a 10 µl microinjection syringe containing a 4 µl suspension of tumor cells ($4\times10^5$). The contents of the syringe were slowly injected into the tibia cavity. To prevent leakage of cells outside the bone, the injection site was sealed with bone wax. For the sham group (control), 4 µl of PBS was injected instead of carcinoma cells into the tibia. At the end of the experiment, radiological, postmortem, and histological evaluations were performed. Rats that showed no obvious tumor growth and bone destruction after inoculation of tumor cells were excluded from the experiments.

Drug injection. For intravenous injection, anti-PD-1 antibody (Nivolumab, 3 or 10 mg/kg or RMP1-14, 10 mg/kg in 100 µl PBS) or control antibody (human IgG4 or rat IgG2A) was administered into the tail vein of mouse. For local intraplantar injection, drugs (20 µl PBS) were injected using a Hamilton microsyringe (Hamilton) with a 30-gauge needle. For intrathecal injection, spinal cord puncture was made with a 30-G needle between the L5 and L6 level to deliver reagents (10 µl) to the cerebral spinal fluid (Chen, G, et al. 2015). For peri-sciatic injection, a mixture of 2 µg siRNA and 1.5 µg of transfection reagent (Chimeric Rabies Virus Glycoprotein Fragment, RVG-9R (Berta, T, et al. 2014)) in 6 µl D5W (5% dextrose in water) was injected with a 30-G needle under the mesoneurium of the left sciatic nerve at mid-thigh level. Care was taken to avoid solution entry into the epineurium of the sciatic nerve.

In situ hybridization. We used probes directed against mouse Pdl1 (NM_021893) and Pdcd1 (NM_008798) designed by Advanced Cell Diagnostics and the RNAscope multiplex fluorescent assay according to the manufacturer's instructions. Pre-hybridization, hybridization and washing were performed according to standard methods (Xu, Z Z, et al. 2015)

Immunohistochemistry in mouse and human tissues and quantification. After appropriate survival times, mice were deeply anesthetized with isoflurane and perfused through the ascending aorta with PBS, followed by 4% paraformaldehyde. After the perfusion, the L4-L5 spinal cord segments, L4-L5 DRGs, sciatic nerves, and melanoma tissues were removed and postfixed in the same fixative overnight. Fresh human DRGs (L4-L5) of 4 non-diseased donors from NDRI (National Disease Research Interchange) (Xu, Z Z, et al. 2015) and the attached spinal nerves were immediately fixed upon delivery in fresh 4% paraformaldehyde overnight. Spinal cord, DRG, and nerve tissue sections (10 or 14 µm) and free-floating spinal cord and skin sections (30 µm) were cut in a cryostat. The sections were blocked with 2% goat or donkey serum for 1 h at room temperature and then incubated overnight at 4° C. with the following primary antibodies: anti-PD-1 (rabbit, 1:500, Sigma, Catalog: PRS4065), anti-phosphorylated SHP-1 (pSHP-1, rabbit, 1:500, Abcam, Catalog: ab51171), anti-NeuN (mouse, 1:1000, Millipore, Catalog: MAB377), anti-NF200 (mouse, 1:1000, Sigma, Catalog: N0142), anti-TREK2 (rabbit, 1:200, Alomone labs, Catalog: APC-055), and anti-CGRP (goat, 1:500, Abcam, Catalog: ab36001) antibodies. After washing, the sections were incubated with cyanine 3(Cy3)- and/or FITC-conjugated secondary antibodies (1:400; Jackson ImmunoResearch) for 2 h at room temperature. For double immunofluorescence, sections were incubated with a mixture of polyclonal and monoclonal primary antibodies, followed by a mixture of Cy3- and FITC-conjugated secondary antibodies or FITC-conjugated IB4 (10 µg/ml; Sigma-Aldrich, Catalog: L2895) (Xu, Z Z, et al. 2015). In some cases, DAPI (1:1000, Vector laboratories, Catalog: H-1200) or Nissl staining (1:200, ThermoFisher Scientific, Catalog: N21483) was used to stain cell nuclei or neurons in tissue sections. The stained sections were examined with a Nikon fluorescence microscope, and images were captured with a CCD Spot camera. For high resolution images, sections were also examined under a Zeiss 510 inverted confocal microscope. To confirm the specificity of PD-1 antibody, blocking experiments were conducted in DRG, nerve, spinal cord, and skin sections using a mixture of anti-PD-1 antibody (1:500=2 µg/ml) and immunizing blocking peptide (1:300=0.7 µg/ml, i.e. 10 fold of the mole concentration of the antibody, Sigma, Catalog: SBP4065), based on a protocol recommended for blocking with immunizing peptide (www.abcam.com/technical).

To determine if there is neuronal loss in Pd1 deficient mice, we conducted semi-quantification of different neuronal populations in DRGs of WT and Pd1$^{-1}$ mice. All the series L4 DRG sections (14 µm) were collected and every 5th section was used for respective immunostaining (CGRP, NF200), IB4 staining, or Nissl staining. The number of positive neurons for each staining was counted and the percentage of the labeled population was calculated based on the Nissl-stained total population in DRG sections. To quantify immunostaining in the dorsal horn, immunofluorescence intensity in spinal cord sections of WT and KO mice (3-5 spinal sections/per mouse) were included.

ELISA. Mouse PD-L1 ELISA kit was purchased from US Biological (Catalog: 027620). ELISA was performed using culture medium, serum and different normal tissues including paw skin, sciatic nerve, gastrocnemius, DRG, brain, spinal cord, lung, thymus, kidney, spleen, liver, as well as malignant skin tissue baring melanoma. Cultured cells and tissues were homogenized in a lysis buffer containing protease and phosphatase inhibitors. Serum was obtained from whole blood, collected by cardiac puncture. After 30 minutes at room temperature, the clot was removed in a refrigerated centrifuge at 2,000×g for 10 min to collect the supernatant (serum). For each ELISA assay, 50 µg proteins, 50 µl of culture medium, or 50 µl of serum were used. ELISA was conducted according to manufacturer's instructions. The standard curve was included in each experiment.

Quantitative real-time RT-PCR. Hindpaw skins of MCI-4W mice were collected 3 h after the intraplantar injection. Total RNA was extracted using Direct-Zol™ RNA MiniPrep Kit (Zymo Research Corporation) and 0.5-1 µg of RNA was reverse-transcribed using the iScript cDNA Synthesise (Bio-Rad). Specific primers including GAPDH control were designed using IDT SciTools Real-Time PCR software. We performed gene-specific mRNA analyses using the MiniOpticon Real-Time PCR system (BioRad)[35]. Quantitative PCR amplification reactions contained the same amount of Reverse transcription (RT) product, including 7.5 µL of 2× iQSYBR-green mix (BioRad) and 100-300 nM of forward and reverse primers in a final volume of 15 µL. The primer sequences were shown in Table 2. Primer efficiency was obtained from the standard curve and integrated for calculation of the relative gene expression, which was based on real-time PCR threshold values of different transcripts and groups.

TABLE 2

Figure 20:
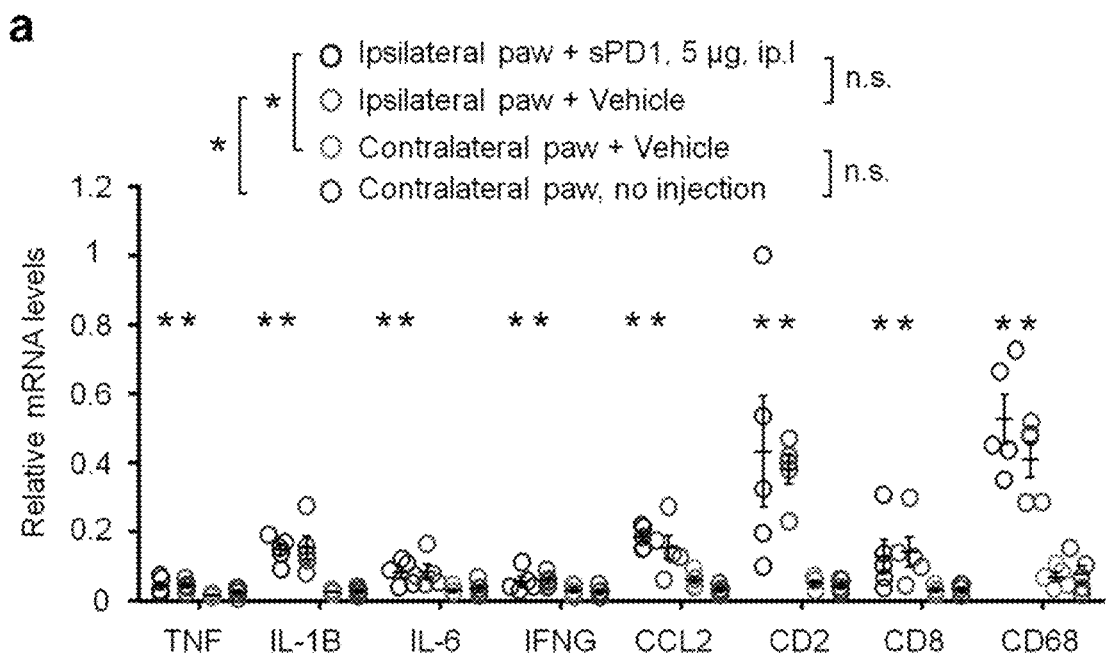
FIG. 20 (Supp.

Primer sequences used for qPCR (FIG. 20).

| Gene | SEQ ID NO | Forward Primers | SEQ ID NO | Reverse Primers | Genbank No. |
| --- | --- | --- | --- | --- | --- |
| TNF | 1 | CCCCAAAGGGATGAGAAGTT | 2 | CACTTGGTGGTTTGCTACGA | NM013693 |
| IL-1B | 3 | TGTCTTGGCCGAGGACTAAG | 4 | TGGGCTGGACTGTTTCTAATG | NM008361 |
| IL-6 | 5 | TCCATCCAGTTGCCTTCTTGG | 6 | CCACGATTTCCCAGAGAACATG | NM031168 |
| IFNG | 7 | CCTAGCTCTGAGACAATGAACG | 8 | TTCCACATCTATGCCACTTGAG | NM008337 |
| CCL2 | 9 | CCCAATGAGTAGGCTGGAGA | 10 | AAAATGGATCCACACCTTGC | NM011333 |
| CD2 | 11 | CACAGGTCAGGGTTGTGTTG | 12 | AATGGGATGACTAGGCTGGA | NM013486 |
| CD8 | 13 | CCGTTGACCCGCTTTCTGT | 14 | TTCGGCGTCCATTTTCTTTGG | NM009857 |
| CD68 | 15 | ACCGCCATGTAGTCCAGGTA | 16 | ATCCCCACCTGTCTCTCTCA | NM001251 |
| GAPDH | 17 | TCCATGACAACTTTGGCATTG | 18 | CAGTCTTCTGGGTGGCAGTGA | NM008084 |

Figure 21A:
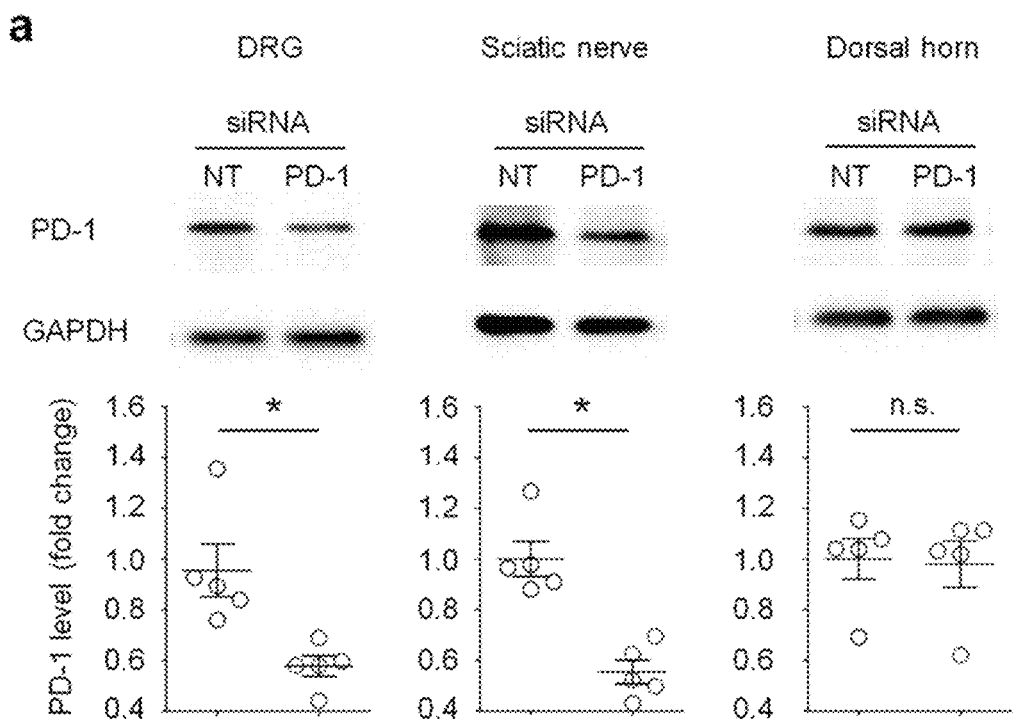

Western blot. Protein samples were prepared in the same way as for ELISA analysis, and 20-50 µg of proteins were loaded for each lane and separated by SDS-PAGE gel (4-15%; Bio-Rad). After the transfer, the blots were incubated overnight at 4° C. with polyclonal antibody against PD-1 (1:1000, rabbit; Sigma, Catalog: PRS4065). For loading control, the blots were probed with GAPDH antibody (1:20000, mouse; Sigma, Catalog: G8795). These blots were further incubated with HRP-conjugated secondary antibody and developed in ECL solution (Pierce). Specific bands were evaluated by apparent molecular sizes. The intensity of the selected bands was analyzed using NIH Image J software. Uncut gels for the represented blots in were included in FIG. 21.

Whole-cell patch clamp recordings in dissociated mouse DRG neuron. DRGs were aseptically removed from 4-7 week-old mice and digested with collagenase (0.2 mg/ml, Roche)/dispase-II (3 mg/ml, Roche) for 120 min. Cells were placed on glass cover slips coated with poly-D-lysine and grown in a neurobasal defined medium (10% fetal bovine serum and 2% B27 supplement) at 37° C. with 5% $CO_2$/95% air for 24 h before experiments. Whole-cell voltage clamp recordings were performed at room temperature to measure transient sodium currents and action potentials, respectively, with an EPC10 amplifier (HEKA) and an Axopatch-200B amplifier with a Digidata 1440A (Axon Instruments) (Xu, Z Z, et al. 2015). The patch pipettes were pulled from borosilicate capillaries (Chase Scientific Glass Inc.). When filled with the pipette solution, the resistance of the pipettes was 4-5 MQ. The recording chamber (300 µl) was continuously superfused (3-4 ml/min). Series resistance was compensated for (>80%), and leak subtraction was performed. Data were low-pass-filtered at 2 KHz, sampled at 10 KHz. The pClamp10 (Axon Instruments) software was used during experiments and analysis. For sodium current recording, pipette solution contained (in mM): CsCl 130, NaCl 9, $MgCl_2$ 1, EGTA 10, HEPES 10, adjusted to pH 7.4 with CsOH. The external solution was composed of (in mM): NaCl 131, TEACl 10, CsCl 10, $CaCl_2$ 1, $MgCl_2$ 2, $CdCl_2$ 0.3, 4-aminopyridine 3, HEPES 10, glucose 10 adjusted to pH 7.4 with NaOH. In voltage-clamp experiments, the transient sodium current ($I_{Na}$) was evoked by a test pulse to +0 mV from the holding potential, -70 mV[25]. For action potential and resting membrane potential (RMP) recordings, pipette solution contained (in mM): K-gluconate 126, NaCl 10, $MgCl_2$ 1, EGTA 10, NaATP 2, and MgGTP 0.1, adjusted to pH 7.3 with KOH. The external solution was composed of (in mM): NaCl 140, KCl 5, $CaCl_2$ 2, $MgCl_2$ 1, HEPES 10, glucose 10, adjusted to pH 7.4 with NaOH. In current-clamp experiments, the action potentials were evoked by current injection steps. RMP was measured without a current injection.

Whole-cell patch clamp recordings in whole mount DRGs of mice ex vivo. L4-L5 DRGs were carefully removed 4 days after sham surgery or CCI surgery and placed in cold oxygenated ACSF. The connective tissue was gently removed under a microscope and the ganglia were digested with a mixture of 0.4 mg/mL trypsin (Sigma) and 1.0 mg/ml type-A collagenase (Sigma) for 30 min at 37° C. The intact ganglia were then incubated in ACSF oxygenated with 95% $O_2$ and 5% $CO_2$ at 28° C. for at least 1 h before transferring them to the recording chamber. DRG neurons were visualized with a 40× water-immersion objective using a BX51WI microscope (Olympus). Whole-cell current and voltage recordings were acquired with an Axon700B amplifier. Patch pipettes (4-7 MO) were pulled from borosilicate glass capillaries on P-97 puller. The recording chamber (300 µl) was continuously superfused (3-4 ml/min). Series resistance was compensated for (>80%), and leak subtraction was performed. The pipette solution contained (in mM): 140 KCl, 2 $MgCl_2$, 10 Hepes, 2 Mg-ATP, pH 7.4. Osmolarity was adjusted to 290-300 mOsm. Data was acquired with a Digidata 1322A acquisition system (molecular devices) using pCLAMP 9.0 software. Signals were low-pass filtered at 5 kHz, sampled at 10 kHz and analyzed offline.

Primary cultures and patch clam recordings in human DRG neurons. Non-diseased human DRGs were obtained from donors through NDRI with permission of exemption from Duke IRB. Postmortem L3-L5 DRGs were dissected from 5 male donors at the age of 27, 31, 43, 54, and 67 and delivered in ice-cold culture medium to the laboratory at Duke University within 24-72 hours of death. Upon the delivery, DRGs were rapidly dissected from nerve roots and minced in a calcium-free HBSS (Gibco). Human DRG cultures were prepared as previously reported (Xu, Z Z, et al. 2015). DRGs were digested at 37° C. in humidified $O_2$ incubator for 120 min with collagenase Type II (Worthington, 285 units/mg, 12 mg/ml final concentration) and dispase II (Roche, 1 unit/mg, 20 mg/ml) in PBS with 10 mM HEPES, pH adjusted to 7.4 with NaOH. DRGs were mechanically dissociated using fire-polished pipettes, filtered through a 100 µM nylon mesh and centrifuged (500×g for 5 min). The pellet was resuspended, plated on 0.5 mg/ml poly-D-lysine-coated glass coverslips, and cells were grown in Neurobasal medium supplemented with 10% FBS, 2% B-27 supplement, 1% N-2 supplement, and 1% penicillin/streptomycin. Whole-cell patch clamp recordings in small-diameter DRG neurons (<55 µm) were conducted at room temperature using patch pipettes with resistances of 2-3 MD. The recording chamber was continuously superfused (3-4 ml/min). The data were acquired at a rate of 10 kHz and filtered at 3 kHz using an EPC-10 amplifier (HEKA, Germany) and an Axopatch-200B amplifier with a Digidata 1440A (Axon Instruments). For sodium current recording, pipette solution contained (in mM): CsCl 130, NaCl 9, $MgCl_2$ 1, EGTA 10, HEPES 10, adjusted to pH 7.4 with CsOH. The external solution was composed of (in mM): NaCl 131, TEACl 10, CsCl 10, $CaCl_2$ 1, $MgCl_2$ 2, $CdCl_2$ 0.3, 4-aminopyridine 3, HEPES 10, glucose 10 adjusted to pH 7.4 with NaOH. In voltage-clamp experiments, the transient sodium current ($I_{Na}$) was evoked by a test pulse to 0 mV from the holding potential of -70 mV. Pre-treatment of the SHP-1 inhibitor SSG was performed 30 min prior to whole-cell patch-clamp recordings. For action potential and RMP recordings, pipette solution contained (in mM): K-gluconate 126, NaCl 10, $MgCl_2$ 1, EGTA 10, NaATP 2, and MgGTP 0.1, adjusted to pH 7.3 with KOH. The external solution was composed of (in mM): NaCl 140, KCl 5, $CaCl_2$ 2, $MgCl_2$ 1, HEPES 10, glucose 10, adjusted to pH 7.4 with NaOH. In current-clamp experiments, the action potentials were evoked by a current injection (Xu, Z Z, et al. 2015). The resting membrane potential was measured without a current injection.

CHO cell culture, transfection and electrophysiology. CHO cell line was purchased from Duke Cell Culture Facility. Cells were cultured in high glucose (4.5 g/L) Dulbecco's Modified Eagle's Medium containing 10% (v/v) fetal bovine serum (Gibco). Transfection (1 µg cDNA) was performed with Lipofectamine™ 2000 Reagent (Invitrogen) at 70% confluency and the transfected cells were cultured in the same growth medium for 48 h before electrophysiological and biochemical studies. PD1/PDCD1 cDNA construct (SC117011, NM_005018) and TREK2/KCNK10 cDNA construct (SC110477, NM_021161) were purchased from Origene Technologies.

Whole-cell patch clamp recordings in transfected CHO cells were conducted at room temperature using patch pipettes with resistances of 5-6 MΩ. The recording chamber was continuously superfused (3-4 ml/min). The data were acquired at a rate of 10 kHz and filtered at 3 kHz using an EPC-10 amplifier (HEKA, Germany). Pipette solution contained (in mM): K-gluconate 126, NaCl 10, $MgCl_2$ 1, EGTA 10, NaATP 2, and MgGTP 0.1, adjusted to pH 7.3 with KOH. The external solution was composed of (in mM): NaCl 140, KCl 5, $CaCl_2$ 2, $MgCl_2$ 1, HEPES 10, glucose 10, adjusted to pH 7.4 with NaOH. In voltage-clamp recordings, TREK2-induced currents were elicited by voltage-ramp from −120 mV to +100 mV every 10s interval. In current-clamp experiments, the resting membrane potential was measured without any membrane potential compensation.

Spinal cord slice preparation and patch clamp recordings in mice ex vivo. The L3-L5 lumbar spinal cord segment was removed from mice under urethane anesthesia (1.5-2.0 g/kg, i.p.) and kept in pre-oxygenated ice-cold artificial cerebrospinal fluid (aCSF) solution composed of (in mM): NaCl 126, KCl 3, $MgCl_2$ 1.3, $CaCl_2$ 2.5, $NaHCO_3$ 26; $NaH_2PO_4$ 1.25; glucose 11. Transverse slices (300-400 μm) were cut on a vibrating microslicer. The slices were perfused with aCSF solution for at least 1 h prior to experiment. The whole cell patch-clamp recordings were made from lamina 110 neurons in voltage clamp mode (Berta, T, et al. 2014). After establishing the whole-cell configuration, neurons were held at −60 mV to record spontaneous EPSCs (sEPSCs) in the presence of 10 μM picrotoxin and 2 μM strychnine. The miniature EPSCs (mEPSCs) were recorded in some neurons in the presence of 10 μM picrotoxin, 2 μM strychnine, and 0.5 μM tetrodotoxin. The resistance of a typical patch pipette is 5-6 MΩ. Signals were filtered at 2 kHz and digitized at 10 kHz. The recording data were analyzed using Mini Analysis (Synaptosoft Inc.).

Spontaneous discharge recordings in mouse sciatic nerve in vivo. Adult male mice (25-32 g) were anaesthetized with urethane (1.5 g/kg, i.p.) and monitored for loss of hind paw pinch reflex with additional injections of urethane (0.2 g/kg). The animals were artificially ventilated with oxygen on a respirator. The left thigh was shaved and an incision made parallel to the femur. The muscle was parted by blunt forceps dissection to expose the sciatic nerve proximal to the trifurcation. A cuff electrode (Microprobes) was placed loosely around the full circumference of the sciatic nerve. Skin flaps were raised to enclose a pool of mineral oil that covered the exposed regions of nerve. The spontaneous discharges in the sciatic nerve were recorded with a microelectrode AC amplifier (1800, A-M systems), filtered (low cut-off 100 Hz and hi cut-off 20 kHz) and digitized at 20 kHz (Digidata 1440A, Molecular Devices). Data were stored with a personal computer using pCLAMP 10 software and analyzed with Offline Sorter software (Plexon, Dallas, Tex.) and Origin pro 8.0 (Origin Lab). The spikes of sciatic nerve were characterized as previously reported (Xu, Z Z, et al. 2015).

Extracellular recording in rat spinal cord in vivo. Rats were anesthetized with urethane (1.5 g/kg, i.p.), and the trachea was cannulated to allow artificial respiration. A laminectomy was performed at vertebrae T13-L1 to expose the lumbar enlargement of the spinal cord. An intrathecal catheter (PE-10) was made for drug injection. The vertebral column was rigidly fixed in the frame with clamps. The exposed spinal cord was covered by warm (37° C.) saline solution. After surgery, the animal was immobilized and artificially ventilated (Capstar-100, IITC Life Science, USA). End-tidal $CO_2$ was maintained at 3.5 to 4.5% and the rectal temperature at 37-38° C. by a feedback controlled heating blanket. The electrocardiogram was monitored, and the heart rate was maintained at 250-300/min. As we reported previously (Yang, Y, et al. 2015), single unit extracellular recordings were made at L4-5 segments, 300-700 μm from the surface of the spinal cord with a glass micropipette filled with 0.5 M sodium acetate (impedance 8-10 MΩ at 1000 Hz). The micropipette was inserted perpendicularly to the spine into the dorsal horn from a point about mid-way between the midline and medial edge of the dorsal root entry zone. Each neuron was functionally identified as a wide dynamic range (WDR) neuron on the basis of their responses to innocuous or noxious mechanical stimulation to the receptive fields (RFs) in the plantar region of the hindpaw. WDR neurons responding to innocuous stimulation and to a greater degree, noxious stimulation of the RF were analyzed in the present study. The recorded signals were amplified with a microelectrode amplifier (1800 A-M System, USA) and fed to computer via a CED 1401 interface for off-line analysis using the Spike 2 software (Cambridge Electronic Design, Cambridge, UK). For low-intensity mechanical stimulation, graded stimuli with von Frey filaments (4, 8, 15, and 26 g) were applied for 15s at 30s intervals. High-intensity (pinch) stimulation with pinch produced by a clip (150 g) was also applied for 15 s. In pharmacological studies, only one cell was studied in each animal.

Measurement of hindpaw melanoma growth in mice. To assess tumor growth after melanoma cell implantation, paw volume was determined by water displacement plethysmometer (Ugo Basile, Italy). The Plethysmometer is a microcontrolled volume meter, specially designed for accurate measurement of the rodent paw swelling. It consists of a water filled Perspex cell into which the paw is dipped. A transducer of original design records small differences in water level, caused by volume displacement. The digital read-out shows the exact volume of the paw.

Behavioral analysis in mice. The following behavioral measurements were conducted in a blinded manner and during daytime (light cycle) normally starting at 9 AM.

Spontaneous pain in mouse melanoma model: We measured the time (seconds) mice spent on licking or flinching the melanoma-bearing hindpaws for 1 or 3 hours.

Von Frey test for mechanical pain: Animals were habituated to the testing environment daily for at least 2 days before baseline testing. The room temperature and humidity remained stable for all experiments. For testing mechanical sensitivity, we confined mice in boxes placed on an elevated metal mesh floor and stimulated their hindpaws with a series of von Frey hairs with logarithmically increasing stiffness (0.02-2.56 g, Stoelting), presented perpendicularly to the central plantar surface. We determined the 50% paw withdrawal threshold by up-down method (Chen, G, et al. 2015).

Hargreaves test for thermal pain: Thermal sensitivity was tested using Hargreaves radiant heat apparatus (IITC Life Science), the basal paw withdrawal latency was adjusted to 9-12 s, with a cutoff of 20 s to prevent tissue damage (Chen, G, et al. 2015).

Rota-rod test for motor function: A Rota-rod system (IITC Life Science Inc.) was used to assess the motor function. Mice were tested for three trails separated by 10 min intervals. During the tests, the speed of rotation was accelerated from 2 to 20 rpm in 3 min. The falling latency was recorded and averaged (Chen, G, et al. 2015).

Conditioned place preference (CPP) test for spontaneous/ ongoing pain: We used a single trial conditioning protocol to measure CPP (Chen, G, et al. 2015). All mice underwent a 3-day pre-conditioning habituation and animal behavior was video-recorded. Analyses of the pre-conditioning (baseline) behavior showed no pre-existing chamber preference. On the conditioning day, mice received the vehicle (PBS, 20 µl, i.pl.) paired with a randomly chosen chamber in the morning, and PD-1 (5 µg in 20 µl PBS, i.pl.) paired with the other chamber 4 h later. Chamber pairings were counterbalanced. On the test day, 20 h following the afternoon pairing, mice were placed in the CPP test box with access to both chambers and the behavior was recorded for 15 min and analyzed by ANY-maze software for chamber preference.

Statistical analyses. All the data were expressed as mean±s.e.m, as indicated in the figure legends. The sample size for each experiment was based on our previous studies on such experiment (Xu, Z Z, et al. 2015; Chen, G, et al. 2015). Statistical analyses were completed with Prism GraphPad 5.0. Biochemical and behavioral data were analyzed using two-tailed student's t-test (two groups) or Two-Way ANOVA followed by post-hoc Bonferroni test. Electrophysiological data were tested using one-way ANOVA (for multiple comparisons) or Two-Way ANOVA (for multiple time points) followed by post-hoc Bonferroni test or student's t-test (two groups). The criterion for statistical significance was P<0.05.

Example 1: PD-L1 Inhibits Acute Inflammatory Pain and Increases Pain Threshold in Nave Animals As a first step to address a role of PD-L1 in acute pain modulation, we examined the effects of PD-L1 in an acute inflammatory pain model. Intraplantar (i.pl) injection of formalin (5%) induced typical bi-phasic inflammatory pain as previously reported (Berta, T, et al. 2014), but the 2nd-phase pain (10-45 min) was substantially inhibited by PD-L1 pre-treatment (i.pl., 1-10 µg, P<0.05, One-Way ANOVA), in a dose-dependent manner (FIG. 1(a)). At high doses (5 and 10 µg), PD-L1 also caused a mild inhibition of the 1st-phase pain (FIG. 1(a)).

Next, we tested if PD-L1 would also alter pain threshold in nave mice. Von Frey test revealed a significant increase in paw withdrawal threshold after i.pl. injection of PD-L1 (5 µg=0.1 nmol, P<0.05, Two-Way ANOVA). The threshold increase was rapid and evident at 30 min and maintained for 3 h after the injection (FIG. 1(b)). Since PD-L1 (CD274) is a chimera protein fused with human IgG at the C-terminal, we used human IgG as an inactive control (http://www.abcam.com/recombinant-mouse-pd-I1-protein-fc-chimera-active-ab180058.html). Notably, this human IgG had no effect on the pain threshold (FIG. 1(b)).

Example 2: PD-L1 is an Endogenous Pain Inhibitor and Alters Basal Pain Thresholds Via PD-1

Figure 2:
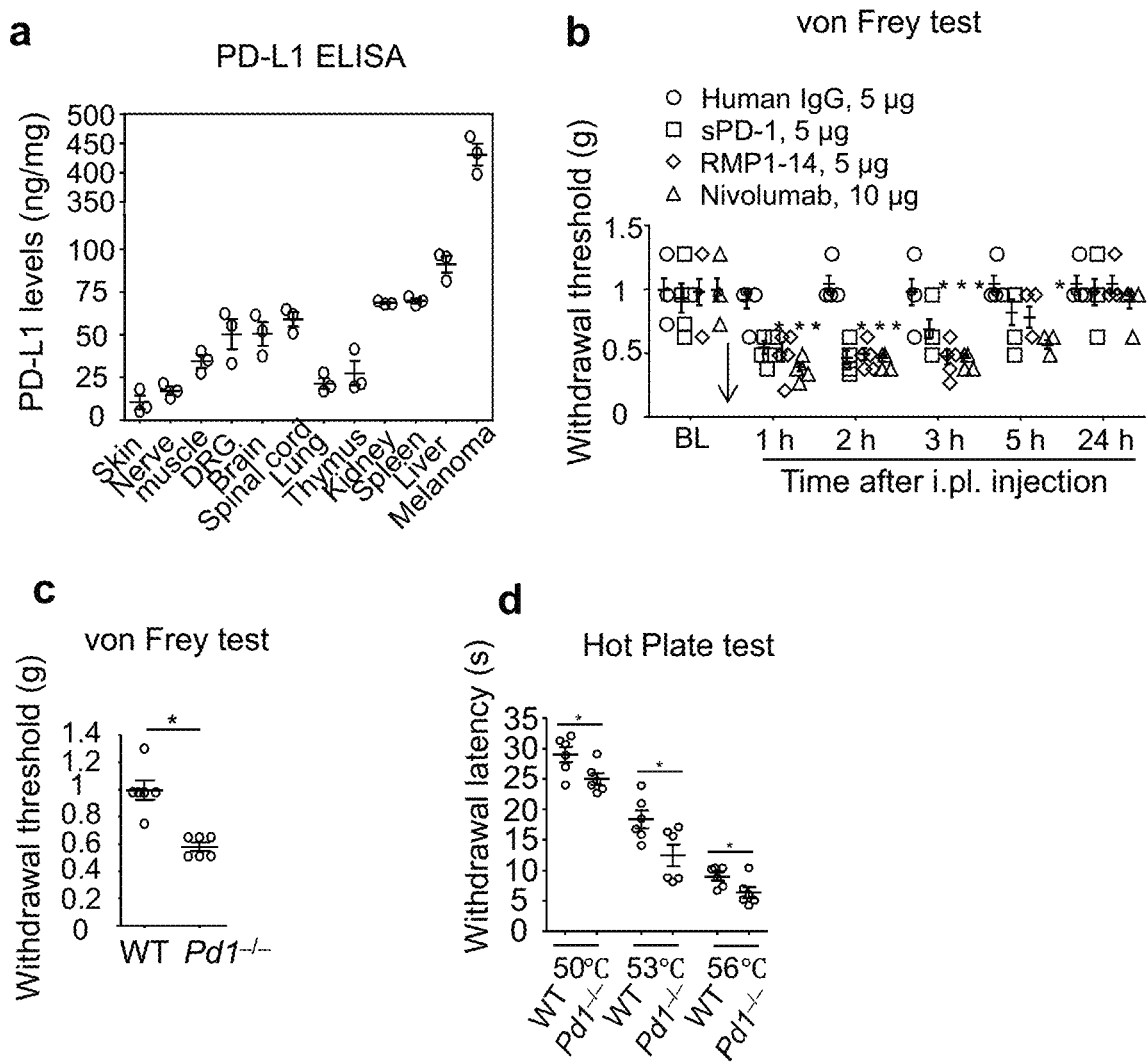
FIG. 2. Endogenous PD-L1 regulates pain sensitivity in naive mice via PD-1. (a) ELISA analysis showing endogenous expression of PD-L1 in non-malignant tissues of nave mice and melanoma tissue removed from a mouse hindpaw 4 w after melanoma cell inoculation. n=3 mice/group. (b) Inhibition of endogenous PD-L1 and PD-1 induces mechanical allodynia in nave mice. PD-L1 was neutralized with soluble PD-1 (sPD-1, 5 μg, i.pl.), and PD-1 was blocked by monoclonal antibodies RMP1-14 (mouse anti-PD-1 antibody, 5 μg, i.pl.) and Nivolumab (human anti-PD-1 antibody, 10 μg, i.pl.). *P<0.05, vs. human IgG, repeated measures Two-Way ANOVA, n=5 mice/group. Arrow indicates drug injection. (c,d) Reduced mechanical and thermal pain threshold in Pd1$^{-/-}$ mice, as shown in von Frey test (c) and hot plate test (d). *P<0.05, Two-tailed student t-test, n=6 mice/group. Data are mean±s.e.m.
Figure 9:
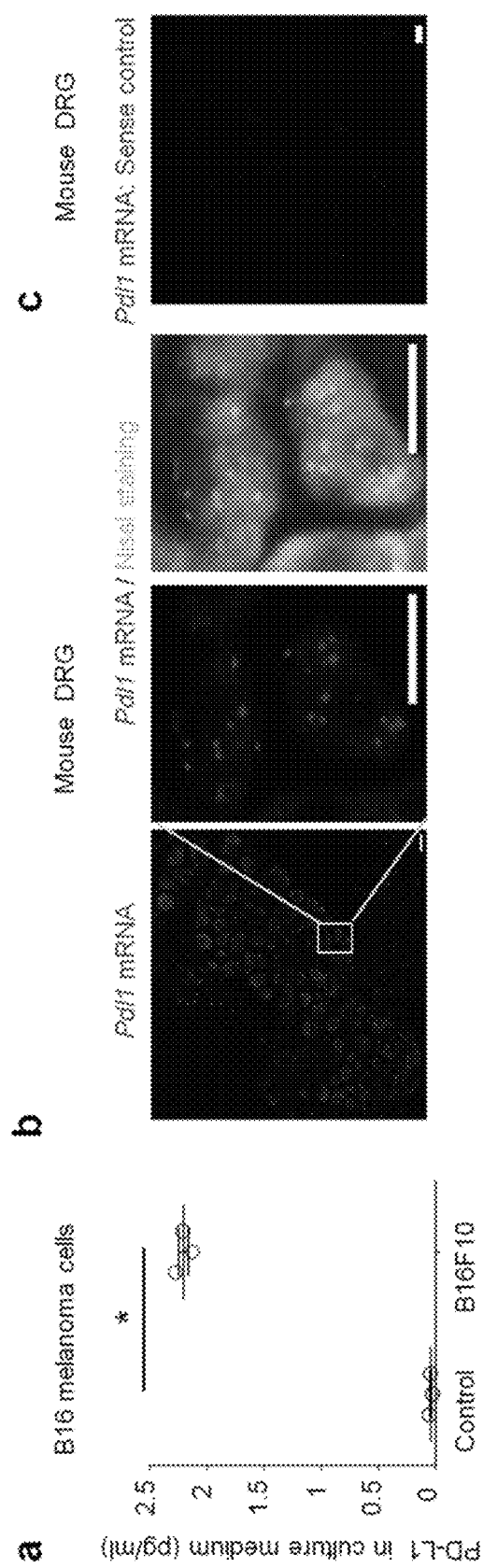
FIG. 9 (Supp.

PD-L1 is produced by malignant tissues and serves as a predictive biomarker in cancer immunotherapy (Patel, S P & Kurzrock, R. Mol Cancer Ther, 2015, 14:847-856). As expected, mouse B16 melanoma tissue has high expression levels of PD-L1 (7450 ng/mg tissue, FIG. 2(a)), as evaluated by ELISA analysis. PD-L1 was also secreted in cultured medium of melanoma cells (FIG. 9(a)). To determine if normal tissues also produce PD-L1, we compared PD-L1 contents in non-neural and neural tissues. Non-neural tissues, such as liver, spleen, and kidney have high levels of PD-L1 ($\approx$70-90 ng/mg tissue, FIG. 2(a)). Interestingly, neural tissues, including brain, spinal cord, and dorsal root ganglia (DRG) contact PD-L1 at levels around 50 ng/mg tissue (FIG. 2(a)). Furthermore, PD-L1 was detected in the sciatic nerve and hindpaw skin tissues (FIG. 2(a)), which contain pain-sensing nerve fibers. These results suggest that PD-L1 is broadly synthesized by neural and skin tissue. In agreement, in situ hybridization revealed Pdl1 mRNA expression in mouse DRG neurons (FIG. 9(b),(c)).

Figure 10:
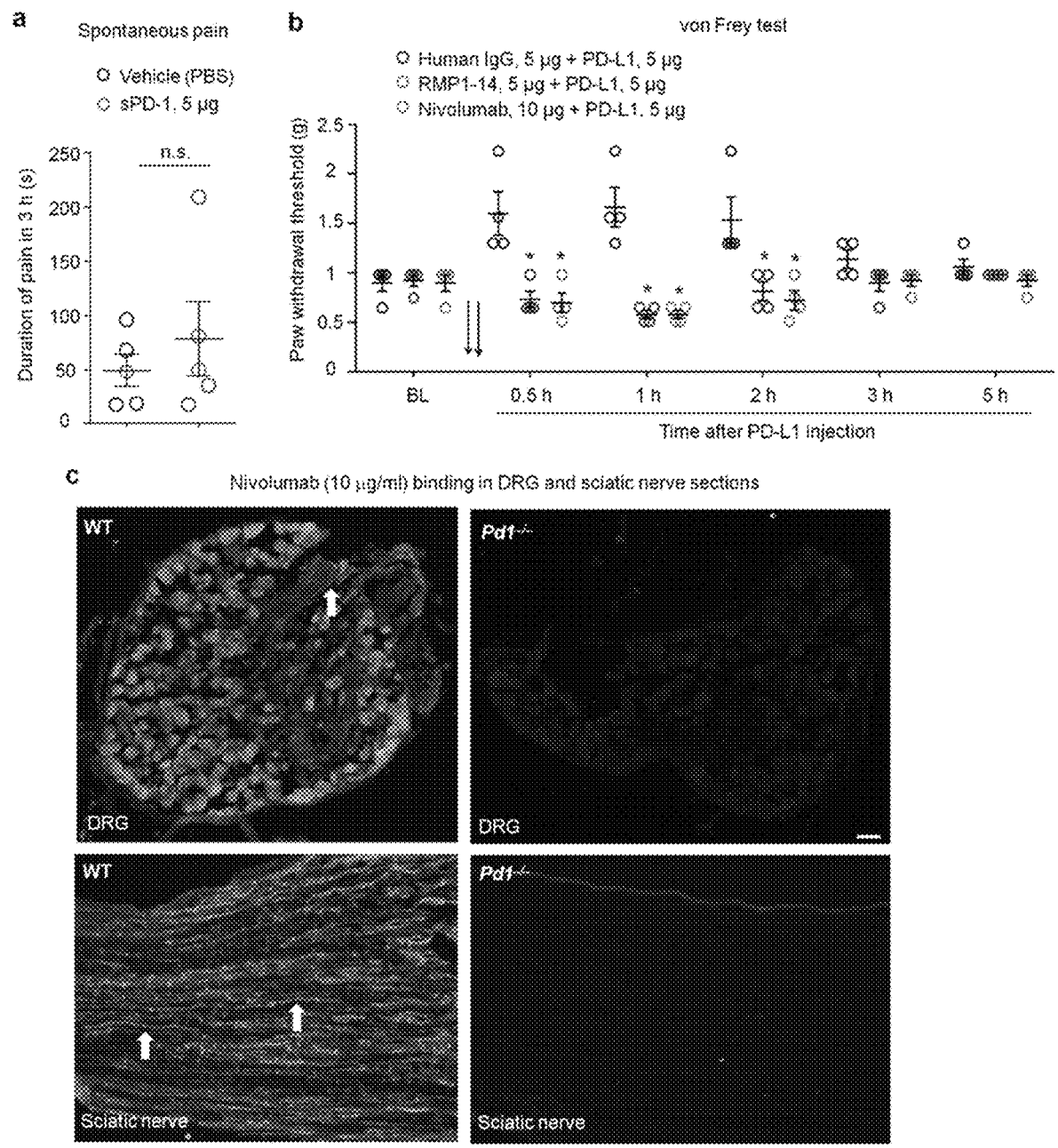
FIG. 10 (Supp.

To determine a role of endogenous PD-L1, produced by non-malignant tissues, in pain regulation, we tested mechanical pain after pharmacological blockade of either PD-L1 or PD-1 in nave mice. Neutralization of hindpaw PD-L1 by i.pl. injection of soluble PD-1 (sPD-1, 5 µg=0.1 nmol) induced a transient mechanical allodynia for 3 h (FIG. 2(b)), without causing spontaneous pain (FIG. 10(a)). Blockade of PD-1 with a mouse anti-PD-1 antibody, RMP1-14 (5 µg, =0.1 nmol, i.pl.), also induced mechanical allodynia for 3 h (FIG. 2(b)). Nivolumab is a FDA-approved fully humanized IgG4 monoclonal antibody, which selectively targets PD-1 (Weber, J S, et al., Lancet Oncol., 2015, 16:375-384) and has shown great success in treating melanoma, lymphoma, and lung cancer (Ansell, S M, et al. 2015; Weber, J S, et al. 2015; Brahmer, J R, et al. Future Oncol, 2015, 11:1307-1326). Of note Nivolumab (10 µg$\approx$0.07 nmol, i.pl.) but not control human IgG, induced marked mechanical allodynia for 5 h (FIG. 2(b)). PD-L1's analgesic effects were blocked by both RMP1-14 and Nivolumab (FIG. 10(b)), suggesting that PD-L1 inhibits pain via PD-1. As a human antibody Nivolumab showed cross-activity in mouse tissue and binding on DRG neurons and sciatic nerve fibers in wild-type (WT) mice, but this binding was absent in Pdl knockout mice (KO, Pd1$^{-/-}$, FIG. 10(c)).

Figure 11:
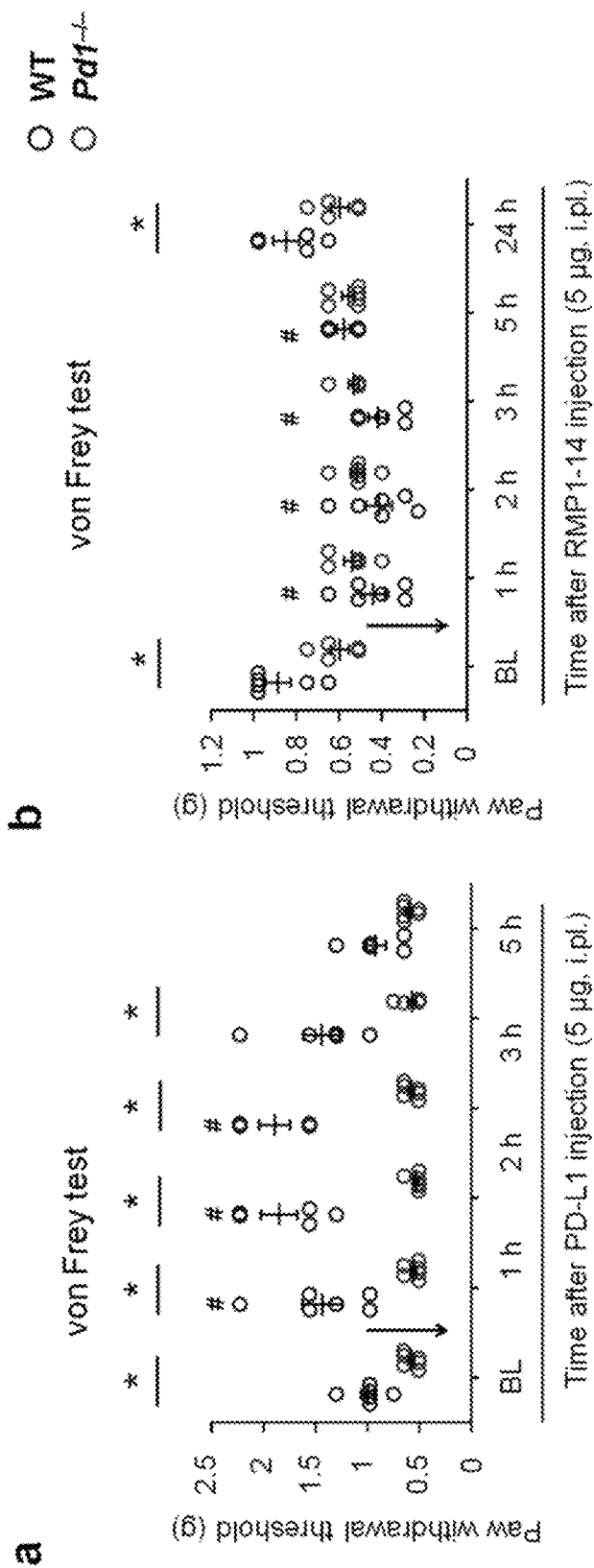
FIG. 11 (Supp.
Figure 12:
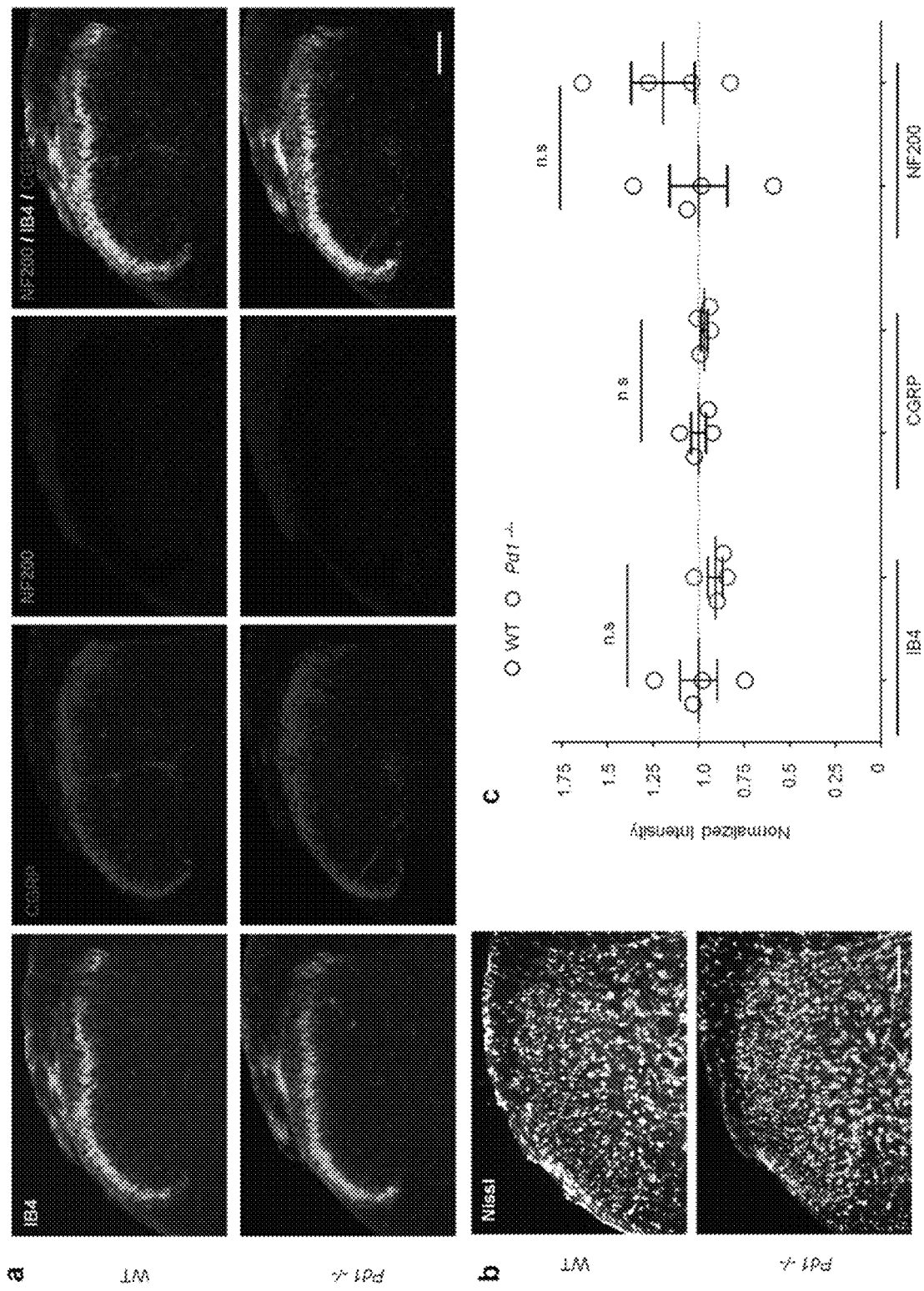
FIG. 12 (Supp.
Figure 13:
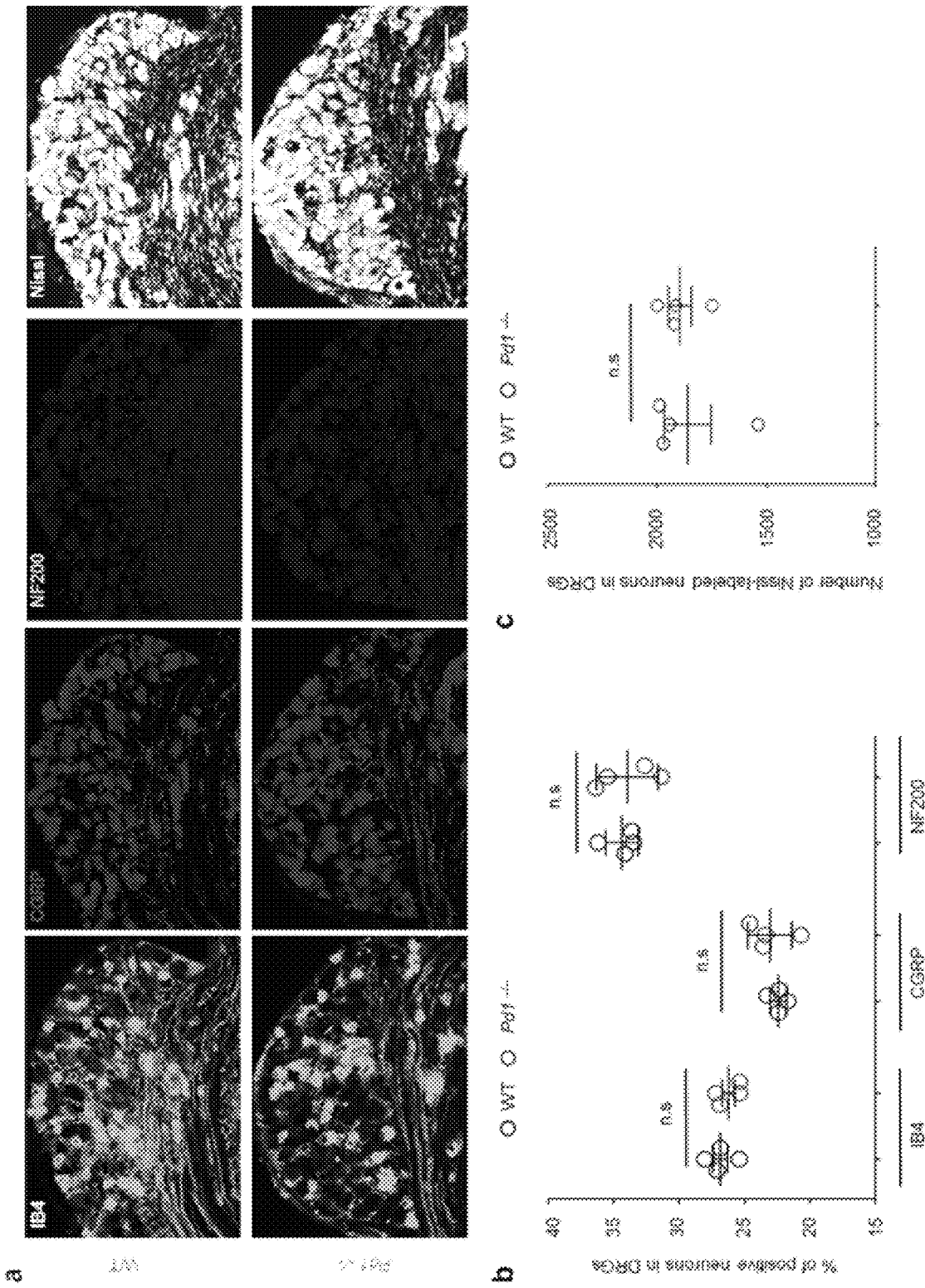
FIG. 13 (Supp.

Next we tested baseline pain and PD-L1-induced analgesia in Pd1$^{-/-}$ mice with and without PD-L1 treatment. Interestingly, baseline pain sensitivity increased in naive Pd1$^{-/-}$ mice. Compared with WT mice Pd1$^{-/-}$ mice displayed mechanical and thermal hypersensitivity, by showing decreased mechanical and thermal pain thresholds in von Frey test and hot plate test (FIG. 2(c),(d)). This result indicates an essential role of PD-1 in regulating basal pain sensitivity. As expected, both PD-L1-induced analgesic effect and RMP1-14-induced hyperalgesic effect were abolished in Pd1$^{-/-}$ mice (FIG. 11(a),(b)). Notably, Pd1$^{-/-}$ mice showed no developmental defects in sensory neurons and their innervations. The central innervations of primary afferents in the spinal cord dorsal horn are comparable in VVT and KO mice (FIG. 12). The distribution patterns of primary sensory neurons, including small-sized nociceptive neurons (CGRP$^+$ peptidergic neurons and IB4$^+$ non-peptidergic neurons) and large-sized A-fiber DRG neurons (NF200$^+$), as well as the total population of sensory neurons are also unaltered in DRG tissues of KO mice (FIG. 13). Taken together, these findings in VVT and Pd1$^{-/-}$ mice strongly suggest that 1) PD-L1 is an endogenous inhibitor of pain, 2) PD-L1 produces analgesia via PD-1, and 3) altered pain sensitivity in Pd1$^{-/-}$ mice is not a result of developmental defects in sensory neurons.

Example 3: PD-1 Receptor is Expressed by Primary Sensory Neurons in Mouse DRGs

Figure 3A:
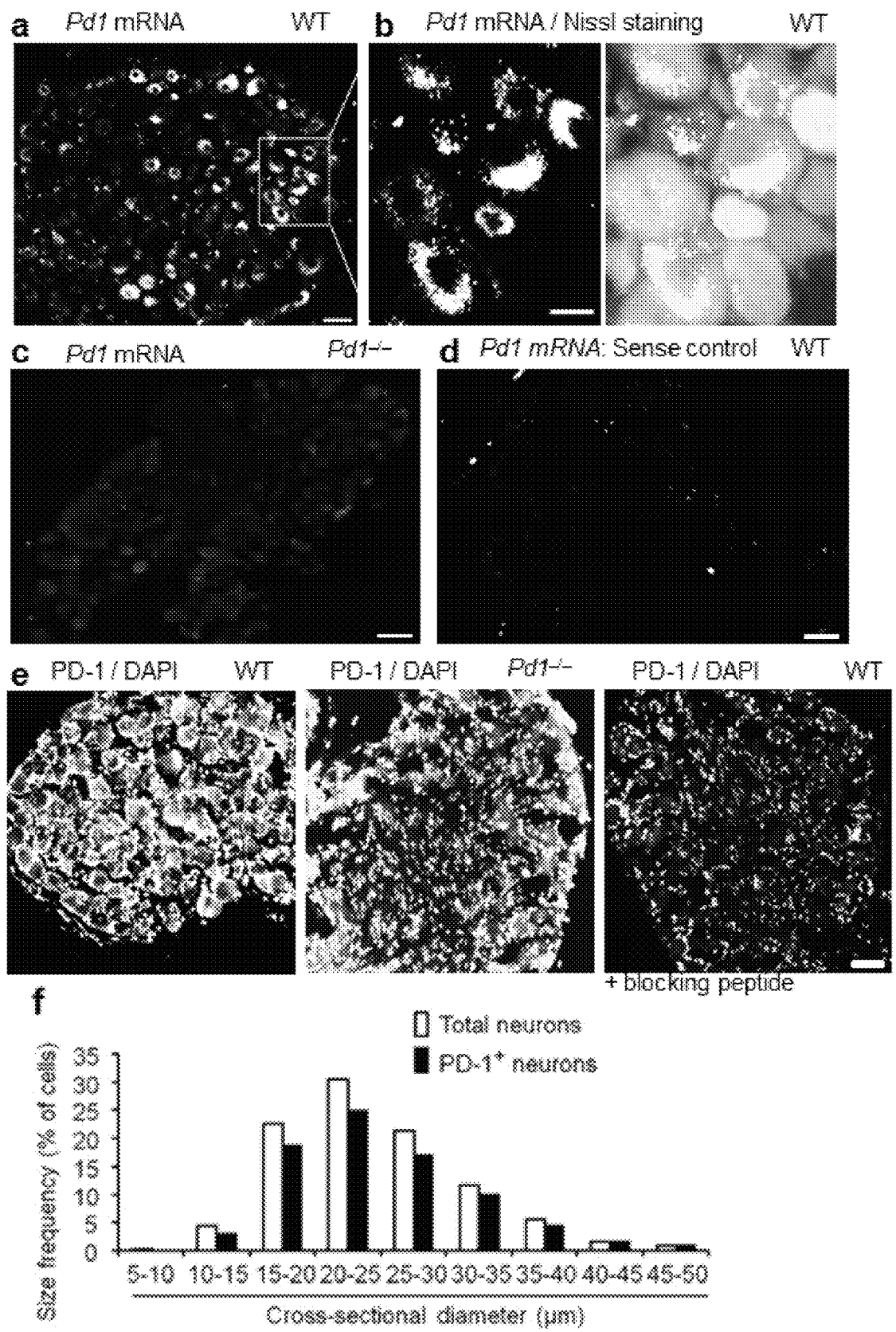
FIG. 3A and FIG. 3B. PD-1 is expressed by mouse DRG neurons and nerve axons.
Figure 3B:
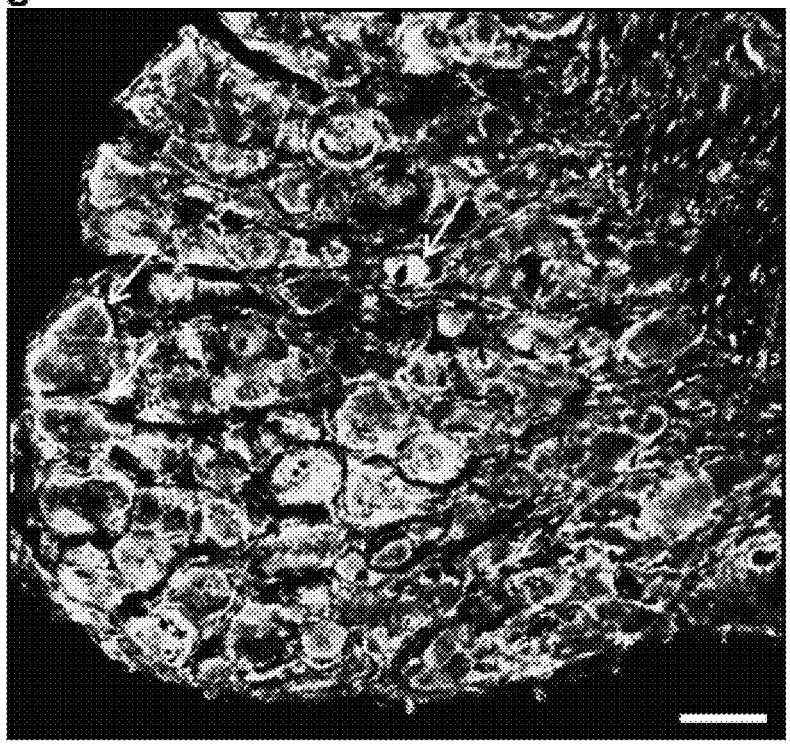
Figure 3B:
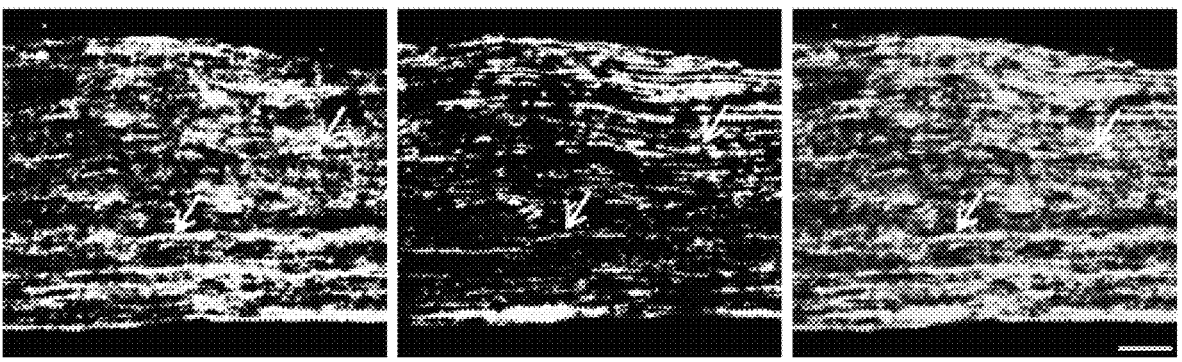
Figure 3B:
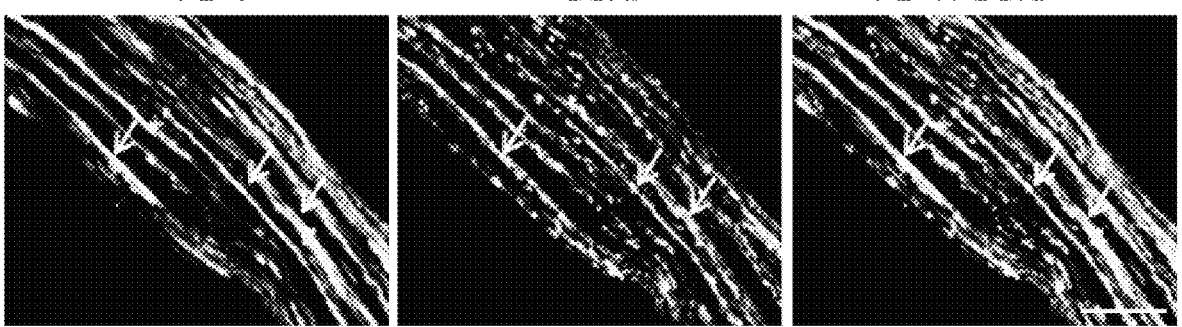

To determine peripheral mechanisms by which PD-L1 modulates pain, we examined Pd1 mRNA and PD-1 protein expression in mouse DRG neurons. In situ hybridization showed Pd1 mRNA expression in majority of DRG neurons with various sizes (FIG. 3A(a),(b)). This expression was lost in Pd1$^{-/-}$ mice (FIG. 3A(c)) and in DRG sections treated with sense control probe (FIG. 3A(d)), confirming the specificity of Pd1 mRNA expression. Immunohistochemistry reveled PD-1 immunoreactivity (IR) in majority of DRG neurons (FIG. 3A(e)). The specificity of the PD-1 antibody was validated by loss of PD-1 immunostaining in DRG neurons of Pd1$^{-/-}$ mice (FIG. 3A(e)) and further confirmed by absence of staining in WT DRG after co-incubation of the antibody with a blocking peptide (FIG. 3A(e)). Size frequency analysis showed a broad expression of PD-1 by DRG neurons with small, medium, and large sizes (FIG. 3A(f)). Double staining confirmed PD-1 expression in both large-diameter A-fiber neurons (NF2001 and small-diameter C-fiber neurons (NF200⁻, FIG. 3B(g)). PD-1-IR was present in NF200+ and NF200⁻ axons in the sciatic nerve, indicating an axonal transport of PD-1 from DRG cell bodies to peripheral axons (FIG. 3B(h)). PD-1-IR axons co-express CGRP, a marker for nociceptive peptidergic neurons (FIG. 3B(i)). Together, these results demonstrate that primary sensory neurons, including nociceptors and their axons, express PD-1, providing a neuronal base for PD-1 modulation of pain.

Example 4: PD-L1 Suppresses Nociceptive Neuron Activity in Mouse DRGs Via PD-1

Figure 4:
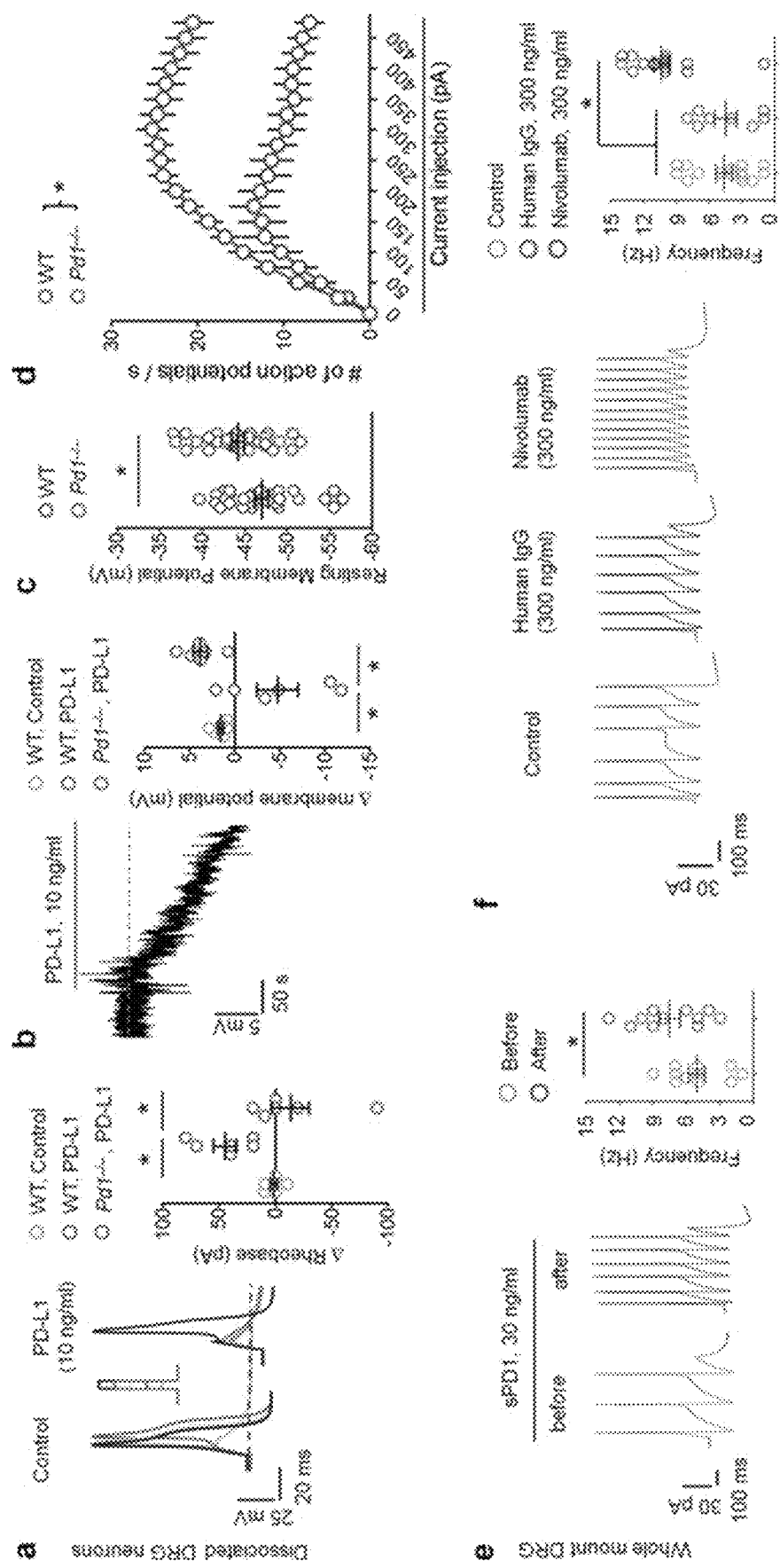
FIG. 4. PD-L1 suppresses neuronal excitability in mouse DRG neurons via PD-1. (a-f) Patch clamp recordings in dissociated (a-d) and whole-mount (e,f) mouse DRG neurons with small diameters (<25 μm). (a) Left, traces of action potentials (AP) showing inhibitory effect of PD-L1 (10 ng/ml) in VVT neurons. Current injection for AP induction starts from +10 pA and increases 10 pA per step. Right, rheobase change in VVT and Pd1$^{-/-}$ mice. n=6 neurons/2 mice. (b) PD-L1 induces hyperpolarization of the resting membrane potential (RMP). Right, change of RMP in VVT and Pd1$^{-/-}$ mice. n=6 neurons/2 mice. (c,d) Altered RMP and increased excitability in DRG neurons of Pd1$^{-/-}$ mice. (c) RMP in VVT and Pd1$^{-/-}$ mice. *P<0.05, paired two-tailed t-test, n=30 neurons/2 mice. (d) Number of action potentials evoked by current injection in WT and Pd1$^{-/-}$ mice. *P<0.05, Two-Way ANOVA followed Bonferroni's post-hoc test, n=30 neurons/2 mice. (e) Whole-mount DRG recording showing increased action potential firing in small-sized DRG neurons after perfusion of sPD-1 (30 ng/ml). Left, traces of evoked action potential before and after sPD-1 perfusion. Right, action potential frequency following sPD-1 perfusion. *P<0.05, paired two-tailed Student's t-test, n=11 neurons/3 mice. (f) Whole-mount DRG recording showing increased action potential firing in small-sized neurons following Nivolumab incubation (2 h, 300 ng/ml). Left, traces of evoked action potential in neurons incubated with control (artificial CSF), human IgG and Nivolumab. Right, frequency of action potentials showing the effects of human IgG and Nivolumab. *P<0.05, vs. control and human IgG, One-Way ANOVA, followed by Bonferroni's post-hoc test, n=8-18 neurons/3 mice. Data are mean±s.e.m.

Activation and sensitization of nociceptive sensory neurons (nociceptors) often produces pain and pain hypersensitivity (Hucho, T & Levine, J D. *Neuron,* 2007, 55:365-376; Reichling, D B & Levine, J D. *Trends Neurosci,* 2009, 32:611-618; Basbaum, A I, et al. *Cell,* 2009, 139:267-284). We postulated that PD-L1/PD-1 inhibits pain via direct modulation of nociceptor activity. We employed patch clamp recordings to evaluate excitability in dissociated small-diameter neurons (<25 μm, presumably nociceptors) in mouse DRGs. Notably, PD-L1, at a very low concentration (10 ng/ml=0.2 nM), evoked a potent and immediate inhibition of action potential induced by current injection and further increased rheobase, a minimum current to induce action potential (FIG. 4(a)). PD-L1 also induced hyperpolarization of the resting membrane potential (RMP) in DRG neurons (FIG. 4(b)). These effects of PD-L1 on action potentials and RMPs were abrogated in Pd1$^{-/-}$ mice, indicating that PD-L1 modulates neuronal excitability through PD-1 (FIG. 4(a),(b)). Furthermore, Pd1-deficient nociceptive neurons displayed increased RMP and firing frequency of action potentials (FIG. 4(c),(d)), suggesting that the intrinsic excitability of nociceptors is enhanced in Pd1 mutant mice.

To further assess the contribution of endogenous PD-L1 and PD-1 to neuronal excitability in WT neurons, we employed pharmacological approaches in a whole mount DRG preparation. Compared to dissociated DRG neurons, whole mount DRG preparation has advantage of retaining extracellular PD-L1. Neutralization of PD-L1 with sPD-1 (30 ng/ml 0.6 nM) increased the firing rate of action potentials in small-diameter DRG neurons (FIG. 4(e)). Blocking the function of PD-1 with Nivolumab, but not the control IgG (300 ng/ml=2 nM), also increased the firing rate (FIG. 4(f)). Together, both gain-of-function and loss-of-function approaches demonstrate a critical role of PD-L1/PD-1 in regulating excitability of nociceptive neurons.

Figure 5:
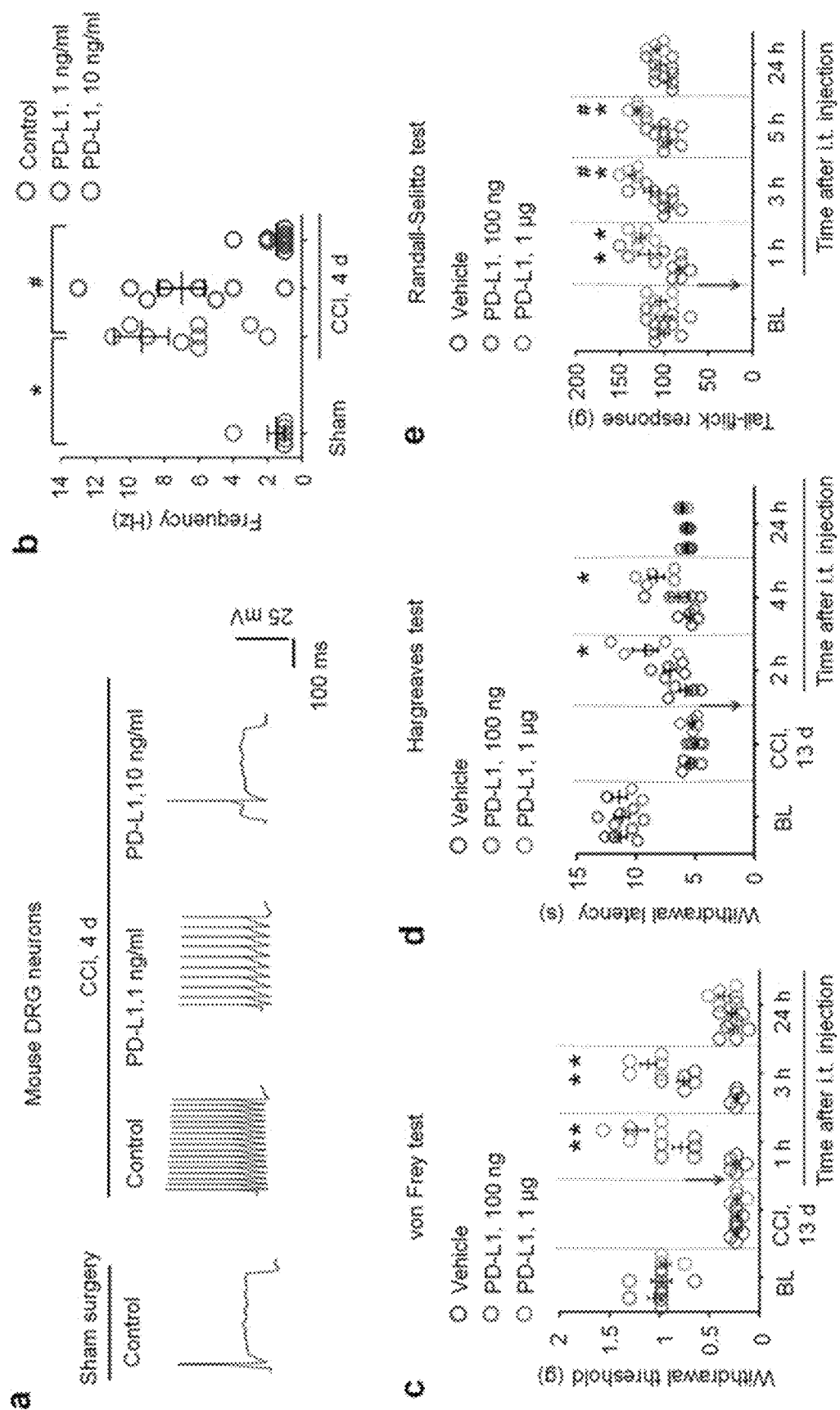
FIG. 5. PD-L1 inhibits neuronal hyperexcitability and neuropathic pain after nerve injury. (a,b) PD-L1 blocks the CCI-induced increases in action potential frequency in small-diameter neurons of whole-mount DRG. (a) Traces of action potentials 4 d after chronic constriction injury (CCI) and the effects of PD-L1 (1 and 10 ng/ml). (b) Frequency of action potentials. *P<0.05, vs. sham control, #p<0.05, vs. control (no treatment), One-Way ANOVA, n=6-9 neurons/group. (c,d) Intrathecal PD-L1 inhibits CCI-induced mechanical allodynia (c) and thermal hyperalgesia (d). *P<0.05, vs. vehicle, repeated measures Two-Way ANOVA, n=5 mice/group. Arrow indicates drug injection. (e) Randall-Selitto test showing increased baseline mechanical pain threshold after intrathecal PD-L1 injection in nave mice. *P<0.05, vs. vehicle, #P<0.05, vs. baseline (BL), repeated measures Two-Way ANOVA, n=5 mice/group. Arrow indicates drug injection. Data are mean±s.e.m.

Example 5: PD-L1 Inhibits Neuronal Hyperexcitability and Neuropathic Pain After Nerve Injury Hyperexcitability of primary sensory neurons after nerve injury has been strongly implicated in chronic pain (Hucho, T & Levine, J D. 2007; Basbaum, A I, et al. 2009; Devor, M, et al. *Pain,* 1992, 48:261-268; Chen, G, et al. 2015). We used mount mouse DRG preparation to examine hyperexcitability in small-sized nociceptive neurons after chronic nerve constriction (CCI). As expected, nociceptive neurons fired more action potentials after CCI (FIG. 5a). Notably, nerve injury-induced hyperexcitability (i.e. increased firing rate of action potentials) of DRG neurons was dose-dependently suppressed by PD-L1 (1-10 ng/ml 0.02-0.2 nM, FIG. 5(a),(b)).

The central axons of nociceptive neurons terminate in the spinal cord dorsal horn to form first-order synapses in the pain pathway (Basbaum, A I, et al. 2009). PD-L1 in DRG neurons could be transported to central axon terminals to modulate spinal cord synaptic transmission and nociception. To test this hypothesis, we examined the effects of intrathecal (i.t.) injection of PD-L1 on CCI-induced neuropathic pain in mice. PD-L1 reduced the CCI-induced mechanical allodynia at a low dose (100 ng, FIG. 5(c)). PD-L1 also significantly reduced CCI-induced heat hyperalgesia at a high dose (1 μg, P<0.05, Two-Way ANOVA, FIG. 5(d)). Randall-Selitto test further revealed that intrathecal PD-L1 increased paw withdrawal threshold in nave mice (FIG. 5(e)).

Example 6: PD-L1 Inhibits Synaptic Transmission and Injury-induced Neuronal Hyperactivities in the Spinal Cord Patch clamp recordings in spinal cord slices showed that superfusion of PD-L1 rapidly (within 1 min) reduced the frequency and amplitude of spontaneous EPSCs (sEPSCs) in lamina 110 neurons (FIG. 14(a)). These interneurons form a nociceptive circuit with C-fiber afferents and projection neurons (Todd, A J. *Nat Rev Neurosci,* 2010, 11:823-836; Braz, J., et al. *Neuron,* 2014, 82:522-536). By sharp contrast, exposure of spinal cord slices to sPD-1 (PD-L1 neutralization) and Nivolumab (PD-1 blockade) increased sEPSC frequency in lamina 110 neurons, but not amplitude (FIG. 14(b),(c)). As expected, PD-L1's inhibition of sEPSC frequency was blocked by Nivolumab (FIG. 14(d)). Thus, PD-L1/PD-1 also has an active role in modulating spinal nociceptive transmission.

Figure 15:
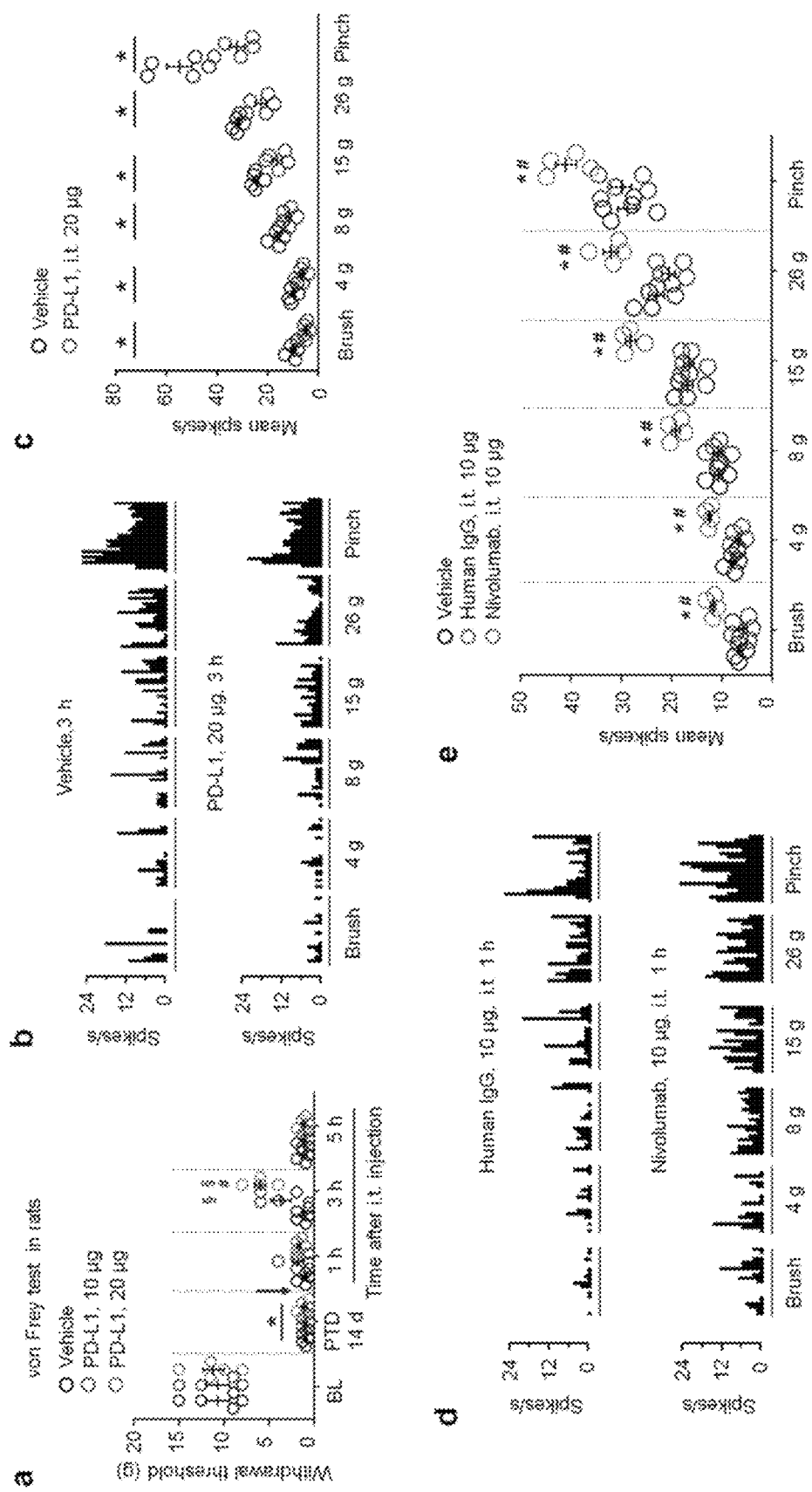
FIG. 15 (Supp.

Next, we tested the central effects of PD-L1 in a bone cancer model in rats (Yang, Y, et al. 2015). PD-L1, given two weeks after tumor cell inoculation via i.t. route, reduced bone cancer-induced mechanical allodynia (P<0.05, Two-Way ANOVA, FIG. 15(a)). Moreover, bone cancer-induced hyperexcitability of wide dynamic range (WDR) neurons in dorsal horn neurons was suppressed by PD-L1 (FIG. 15(b), (c)), whereas Nivolumab enhanced activities of WDR neurons (FIG. 15(d),(e)). Taken together, our data suggest that PD-L1 is a neuromodulator in both the peripheral and central nervous system; and in the spinal cord PD-L1 regulates acute and chronic pain by suppressing nociceptive synaptic transmission and injury-induced neuronal plasticity in dorsal horn neurons via PD-1 receptor.

Example 7: PD-L1 Modulates Sodium Currents and TREK2 Potassium Channels Via SHP-1

Figure 16:
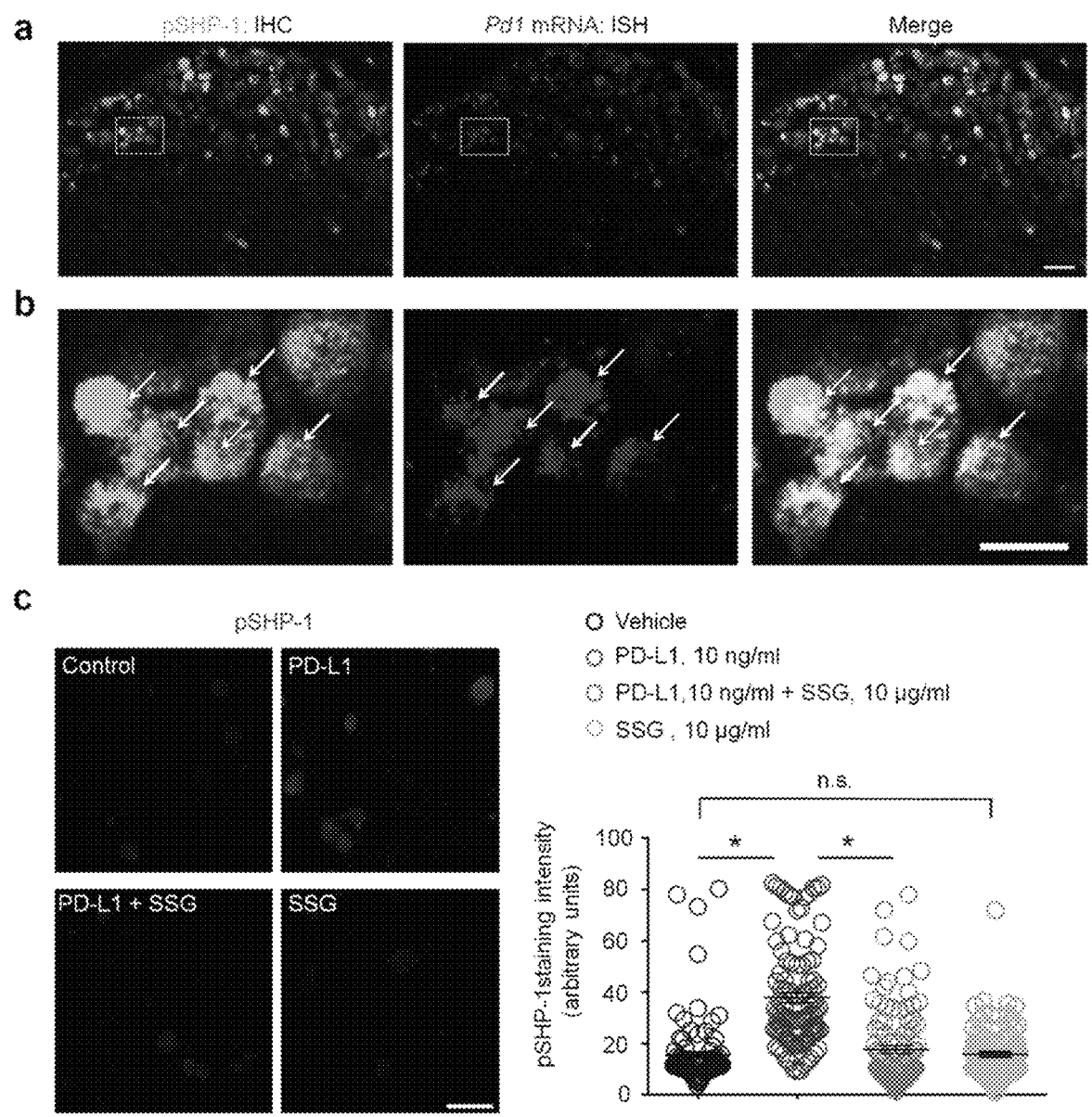
FIG. 16 (Supp.

We also assessed how PD-L1 modulates neuronal excitability. Activation of PD-1 by PD-L1 recruits the tyrosine phosphatases SHP-1/SHP-2 (Src homology region 2 domain-containing phosphatase-1 and 2) to mediate PD-L1's biological actions in immune cells (Keir, M E, et al. 2008; Hebeisen, M, et al. *J Clin Invest,* 2013, 123:1044-1056). Immunohistochemistry shows that PD-L1 is sufficient to activate SHP-1 in vivo after i.t. injection, leading to increased phosphorylation of SHP-1 (pSHP-1) in mouse DRG neurons (FIG. 6(a)). In agreement, pSHP-1 was co-localized with Pd1 mRNA in DRG neurons (FIG. 16(a),(b)). Moreover, PD-L1-induced SHP-1 phosphorylation was blocked by SHP-1 inhibitor sodium1 stibogluconate (SSG) in dissociated DRG neurons (FIG. 16(c)). Intraplantar administration of PD-L1 induced analgesia by reducing paw withdrawal frequency in nave animals; but this analgesic effect of PD-L1 was abolished by i.pl. SSG (FIG. 6(b)). Thus, SHP-1 is not only a downstream signaling event following PD-1 activation in DRG neurons but also contributes to PD-L1-evoked analgesia.

Given an important role of sodium channels in generating action potentials and pain (Bennett, D L & Woods, C G. *Lancet Neurol,* 2014, 13:587-599), we examined the effects of PD-L1 on transient sodium currents in mouse DRG neurons with small diameters. PD-L1 perfusion (10 ng/ml) caused a gradual and persistent inhibition of transient sodium currents (FIG. 6(c)). Moreover, PD-L1-induced inhibition of sodium currents was partially blocked by the SHP inhibitor SSG (FIG. 6(c)), supporting an involvement of SHP.

Figure 6:
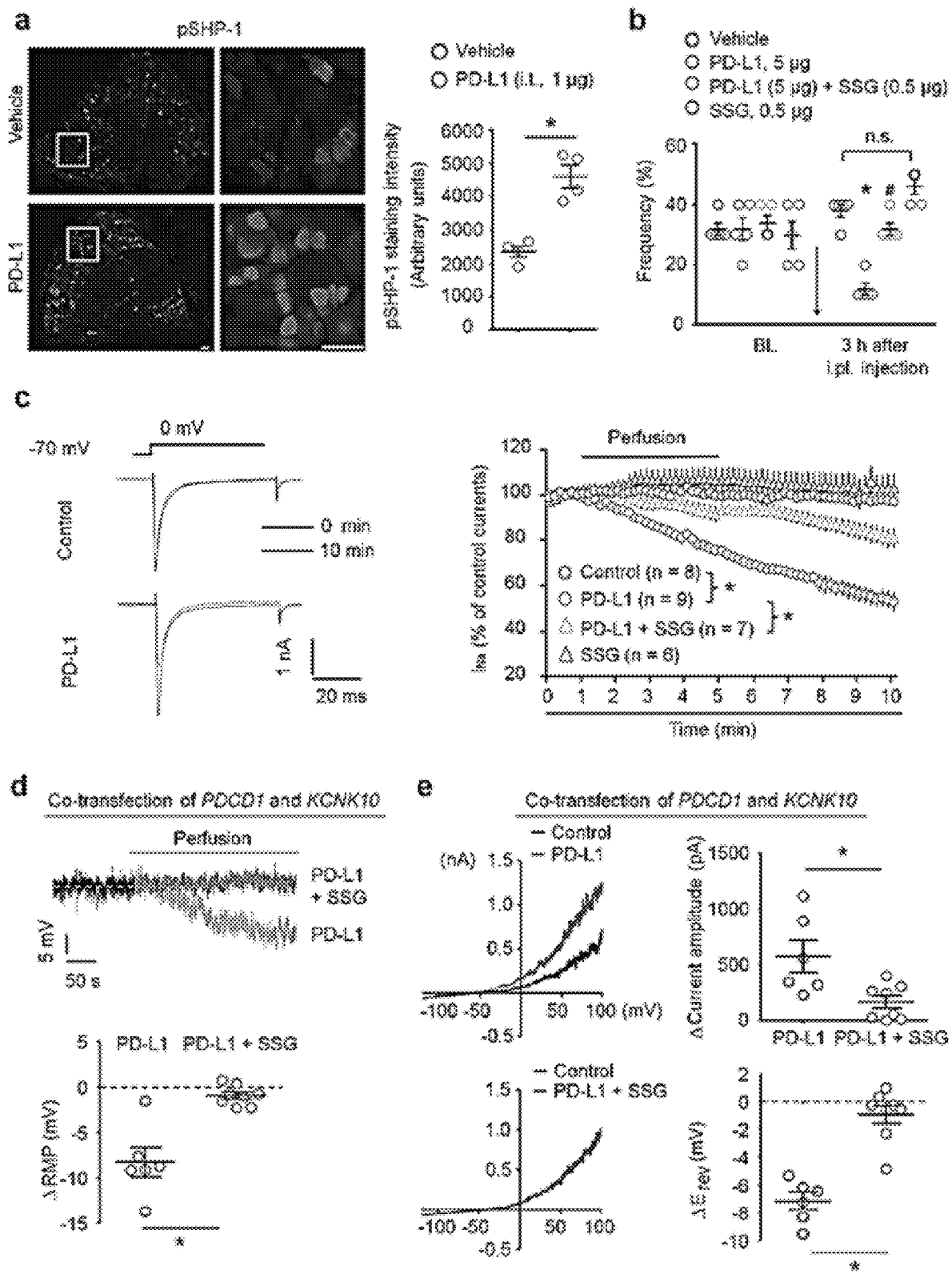
FIG. 6. PD-L1 modulates neuronal excitability and pain via SHP-1. (a) Intrathecal PD-L1 (i.t. 1 μg, 30 min) increased phosphorylation of SHP-1 (pSHP-1) in mouse DRG neurons. Left, images of pSHP-1 immunostaining in vehicle and PD-L1 treated group. Scale, 50 μm. Middle, enlarged images from the boxes. Scale, 50 μm. Right, intensity of immunofluorescence of pSHP-1$^{+}$ neurons. *P<0.05, Two-tailed t-test, n=4 mice/group. (b) Paw withdrawal frequency to a 0.6 g filament in nave mice and effects of i.pl. SSG (SHP-1 inhibitor), PD-L1, and PD-L1 plus SSG in nave mice. *P<0.05, vs. vehicle (PBS), #p<0.05, vs. PD-L1, n.s., no significance, One-Way ANOVA, n=5 mice/ group. (c) Inhibition of transient sodium currents by PD-L1 (10 ng/ml) in dissociated DRG neurons and effect of SSG (11 μM). Left, traces of sodium currents. Right, time course of relative sodium currents. *P<0.05, Two-Way repeated measures ANOVA, n=6-9 neurons/2 mice. (d) Regulation of RMP by PD-L1 (10 ng/ml) and its blockade SSG (11 μM) in dissociated DRG neurons. *P<0.05, two-tailed Student's t-test, n=6-8 neurons/2 mice. (e) PD-L1 increases TREK2 activity via SHP-1 in CHO cells. Left, traces of TREK2-induced outward currents and effects of PD-L1 and SSG. Right, quantification of outward currents and RMP changes. *P<0.05, two-tailed Student's t-test, n=6-8 cells/2 cultures. Data are mean±s.e.m.
Figure 17:
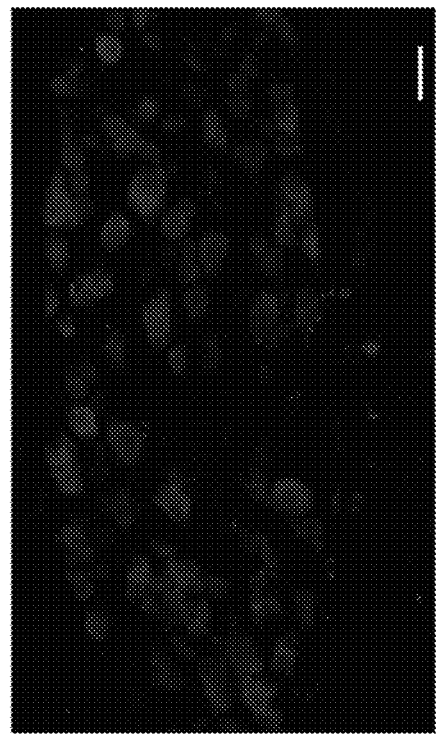
FIG. 17 (Supp.
Figure 17:
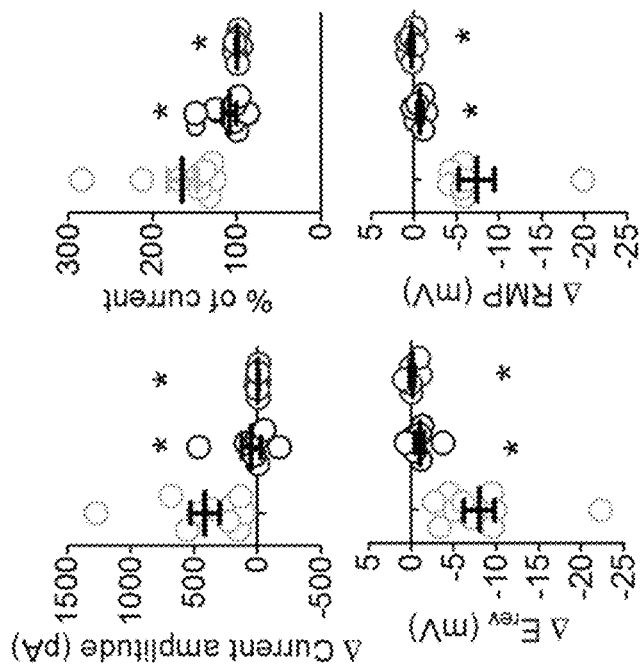
Figure 17:
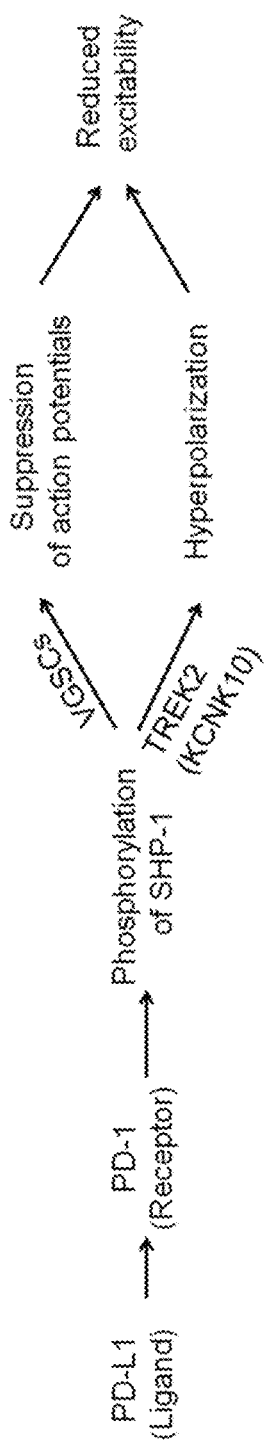

Two-pore $K^+$ channel TREK2 plays a major role in regulating RMP in DRG nociceptive neurons of rats (Acosta, C, et al., *J Neurosci,* 2014, 34:1494-1509). TREK2 also expressed in mouse DRG neurons (FIG. 17(a)). We assessed if PD-L1 would modulate TREK2 activity in heterologous CHO cells. PD-L1 caused hyperpolarization of RMP (ARMP 8 mV) in CHO cells co-expressing PD-1 (encoded by PD1 or PDCD1) and TREK2 (encoded by KCNK10), but this change was blocked by SSG (FIG. 6(d)). PD-L1 also potentiated TREK2-induced currents and produced a negative shift in reversal potential ($E_{rev}$) in PD-1/TREK2 co-expressing CHO cells; and both were abolished by SSG (FIG. 6e). However, PD-L1 alone was insufficient to alter the voltage-ramp currents and $E_{rev}$ in CHO cells expressing either TREK2 or PD-1 (FIG. 17(b)). Collectively, activation of PD-1 by PD-L1 might modulate neuronal excitability by suppressing the function of sodium channels and enhancing the function of potassium channels (TREK2) via SHP-1 (FIG. 17(c)).

Example 8: Human DRG Neurons Express Functional PD-1

Figure 7:
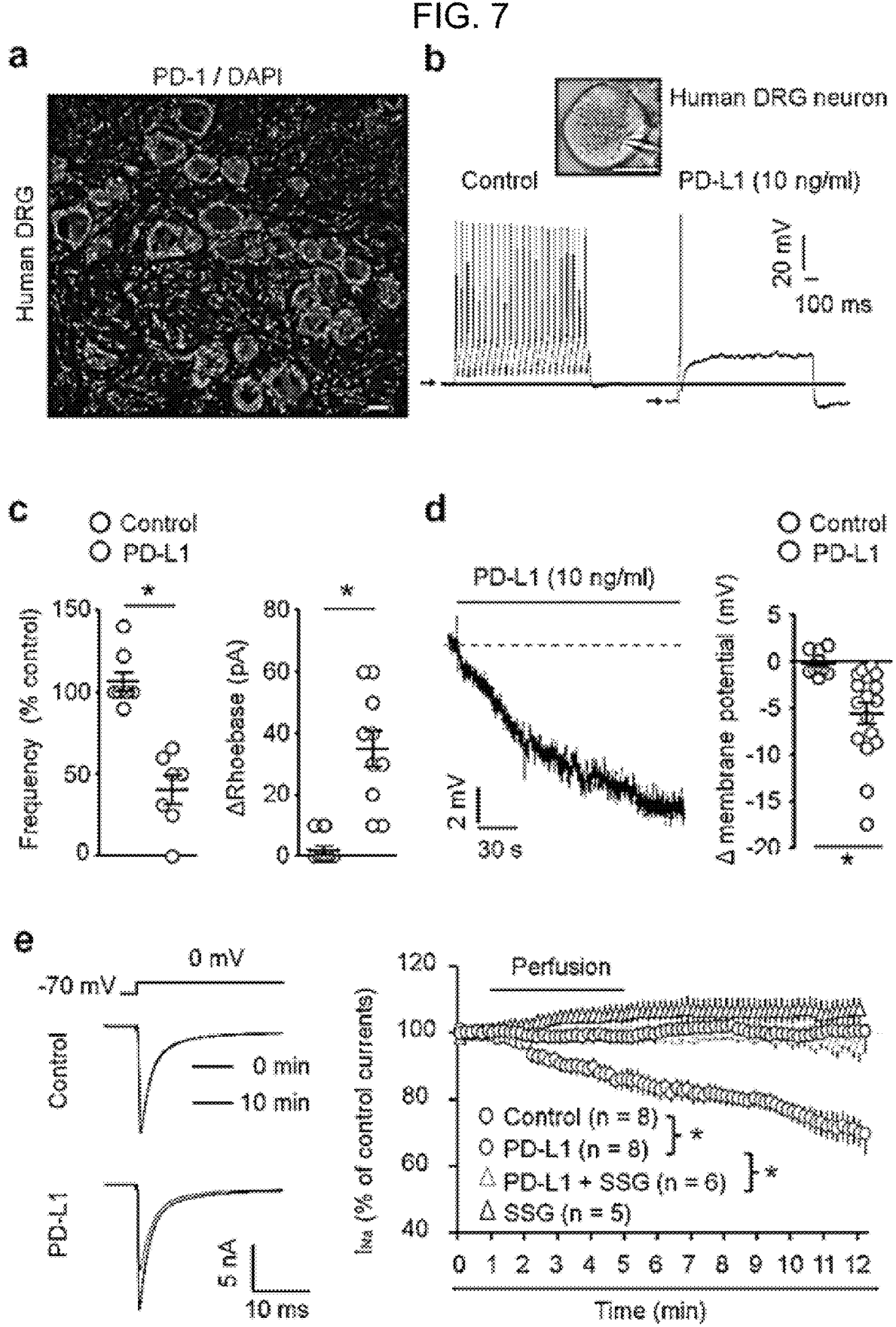
FIG. 7. PD-L1 suppresses action potential firing and sodium currents and regulates resting membrane potentials in human DRG neurons. (a) PD-1 immunostaining in human DRG section. Blue DAPI staining labels all nuclei of cells in DRG. Scale, 50 µm. (b,c) In vitro patch-clamp recording in dissociated small-diameter human DRG neurons (30-50 µm). (b) Suppression of evoked action potential firing by PD-L1. Insert shows a human DRG neuron with a recording pipette. Scale, 25 µm. Blue and red arrows show shift of RMP after PD-L1 treatment. (c) Percentage change of action potential frequency (left) and rheobase change (right) following PD-L1 perfusion (10 ng/ml). *P<0.05, vs. vehicle, Two-tailed Student's t-test, n=7-10 neurons/3 donors. (d) Reduction of RMP after PD-L1 perfusion. Right, quantification of RMP change. *P<0.05, vs. vehicle, Two-tailed Student's t-test, n=13 and 17 neurons/3 donors. (e) Inhibition of transient sodium currents in dissociated human DRG neurons by PD-L1 (10 ng/ml) and effect of SSG (11 µM). Left, traces of sodium currents. Right, time course of relative sodium currents showing time-dependent inhibition by PD-L1. *P<0.05, Two-Way repeated measures ANOVA, n=5-8 neurons/2 donors. Data are mean±s.e.m.
Figure 18:
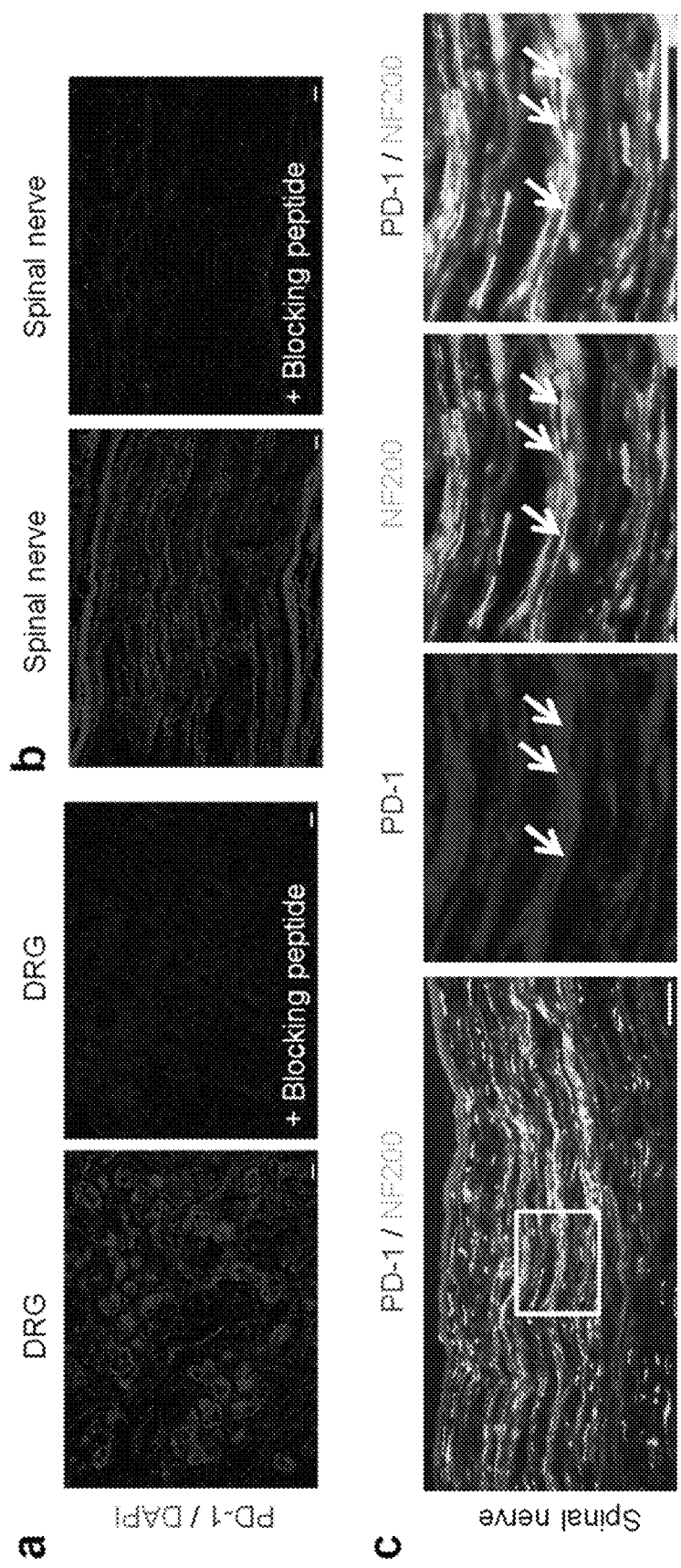
FIG. 18 (Supp.

A translational gap from rodents to humans was blamed for many failures in developing pain therapeutics (Woolf, C J. *Nat Med,* 2010, 16:1241-1247; Mogil, J S. *Nat Rev Neurosci,* 2009, 10:283-294). To this end, we examined the PD-1 expression and function in human DRG neurons from non-diseased donors, as shown in our previous studies (Xu, Z Z, et al. 2015; Han, Q, et al. Neuron, 2016). PD-1 IR was observed on cell surface of human DRG neurons with small and large sizes as well as in human spinal nerve axons (FIG. 7(a), FIG. 18(a),(b)). This staining in human DRG and nerve sections was abolished by the immunizing blocking peptide (FIG. 18(a),(b)). Both NF200 positive and negative axons of human spinal nerve expressed PD-1 (FIG. 18(c)).

Importantly, PD-1 receptor is functional in human DRG neurons: incubation of dissociated small-diameter nociceptive neurons (30-50 μm) with PD-L1 directly altered neuronal activities. At an concentration (10 ng/ml) that is effective in suppressing mouse nociceptive neuron activity (FIG. 4(a),(b)), PD-L1 markedly inhibited the firing frequency of action potentials and further increased the threshold for action potential induction (rheobase) in human DRG neurons (FIG. 7(b),(c)). PD-L1 also caused hyperpolarization of human nociceptive neurons by decreasing RMP (FIG. 7(d)). Additionally, PD-L1 perfusion (10 ng/ml) caused a gradual and persistent inhibition of transient sodium currents in human DRG neurons (FIG. 7(e)). Notably, PD-L1-induced inhibition of sodium currents was partially blocked by SSG in mouse DRG neurons (FIG. 6(c)) but completely blocked by SSG in human DRG neurons (FIG. 7(e)), supporting an important role of SHP in regulating PD-L1 signaling in human sensory neurons.

Figure 8A:
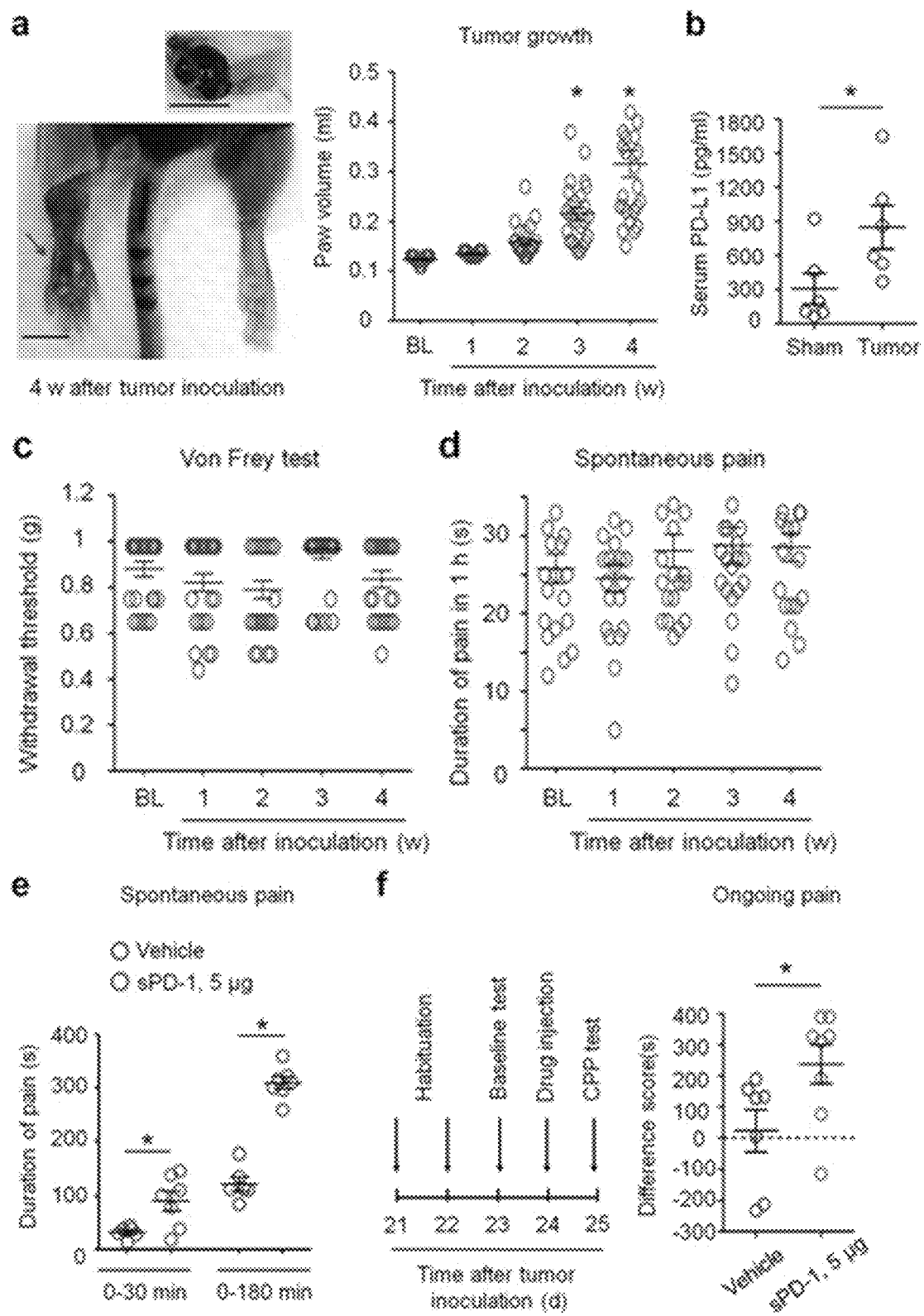
FIG. 8A(a)-(f) and FIG. 8B(g)-(l). Blocking of PD-L1 or PD-1 signaling induces spontaneous pain and allodynia in a mouse melanoma model.

Example 9: PD-L1 and PD-1 Mask Spontaneous Pain and Allodynia in a Mouse Melanoma Model Given the high expression of PD-L1 in melanoma (FIG. 2(a)), we examined the contribution of PD-L1 and PD-1 to altered pain sensitivity in a mouse model of melanoma. Intraplantar injection of mouse melanoma cells ($5 \times 10^5$ cells in 20 μl) into C57BL/6 mice lead to time-dependent tumor growth in a hindpaw, showing a 3-fold increase in paw volume 4 weeks after melanoma cell implantation (MCI-4w, FIG. 8A(a)). Melanoma-bearing mice also exhibited increased PD-L1 levels in serum at MCI-4w (FIG. 8A(b)). Despite profound tumor growth, we did not observe cardinal features of cancer pain, including mechanical allodynia and spontaneous pain (licking/flinching the tumor-bearing paw) in tumor-bearing hind paws (FIG. 8A(c),(d)).

Figure 19:
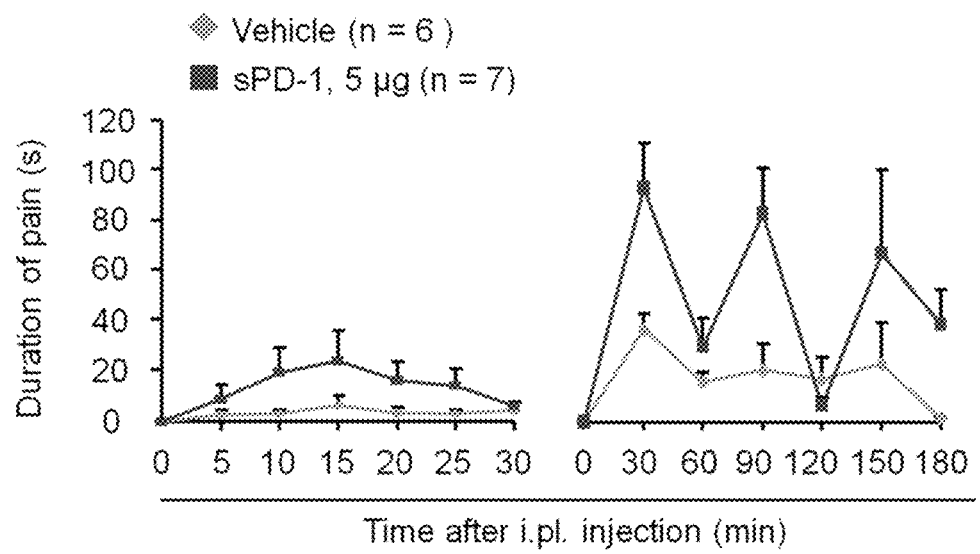
FIG. 19 (Supp.
Figure 19:
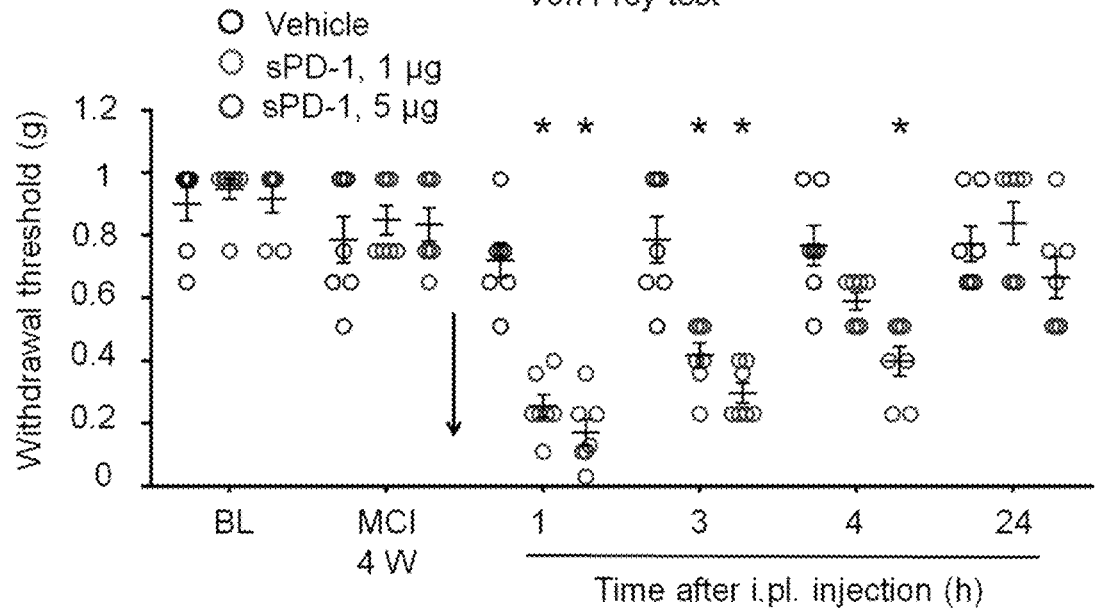

Next, we tested the hypothesis that pain after melanoma could be masked by upregulated PD-L1 function. We employed several pharmacological approaches to block PD-L1/PD-1 signaling. Strikingly, local neutralization of PD-L1, by i.pl. injection of soluble PD-1 (sPD-1, 5 μg, MCI-4w), elicited marked spontaneous pain (FIG. 8A(e)). The onset of spontaneous pain was very rapid: mice displayed licking/flinching behavior in melanoma-bearing paws within 10-30 min after the injection. This spontaneous pain was also phasic, showing a peak every hour for the first 3 h (FIG. 19(a)). The same sPD-1 treatment also induced mechanical allodynia (FIG. 19(b)). Conditioned place preference (CPP) is an operant measurement of ongoing pain (Chen, G, et al. 2015). Using a two-chamber test, we found that i.pl. sPD-1 treatment also resulted in marked CPP (FIG. 8A(f)).

Given an important role of PD-L1 in regulating the function of immune system, we also investigated the effects of sPD-1 treatment on T cell and inflammatory markers in the ipsilateral hindpaw skin surrounding melanoma and control skin in the contralateral paw. To correlate the changes of these immune markers with pain, we collected skin tissues in the acute phase, 3 h after the sPD-1 treatment when robust allodynia and spontaneous pain developed. MCI resulted in increased mRNA levels of T cell markers (CD2, CD3), macrophage marker (CD68), and inflammatory cytokine markers (TNF, IL-1B, IL-6, IFNG, CCL2) in the ipsilateral skin, compared with the contralateral skin (FIG. 20). However, the mRNA levels of these immune/inflammatory markers did not alter after the sPD-1 treatment (FIG. 20). This result further indicates that sPD-1 induces pain via non-immune modulation, at least in the acute phase (i.e. first 3 h).

To further test a peripheral and neuronal role of PD-1 in regulating pain in melanoma, we employed a gene therapy method we recently established (Berta, T, et al. 2014) in which small interfering RNA (siRNA) was used to knockdown PD-1 expression specifically in DRG neurons. This method allows siRNA uptake by DRG sensory neurons via axonal retrograde transport of siRNA (Berta, T, et al. 2014).

Figure 8B:
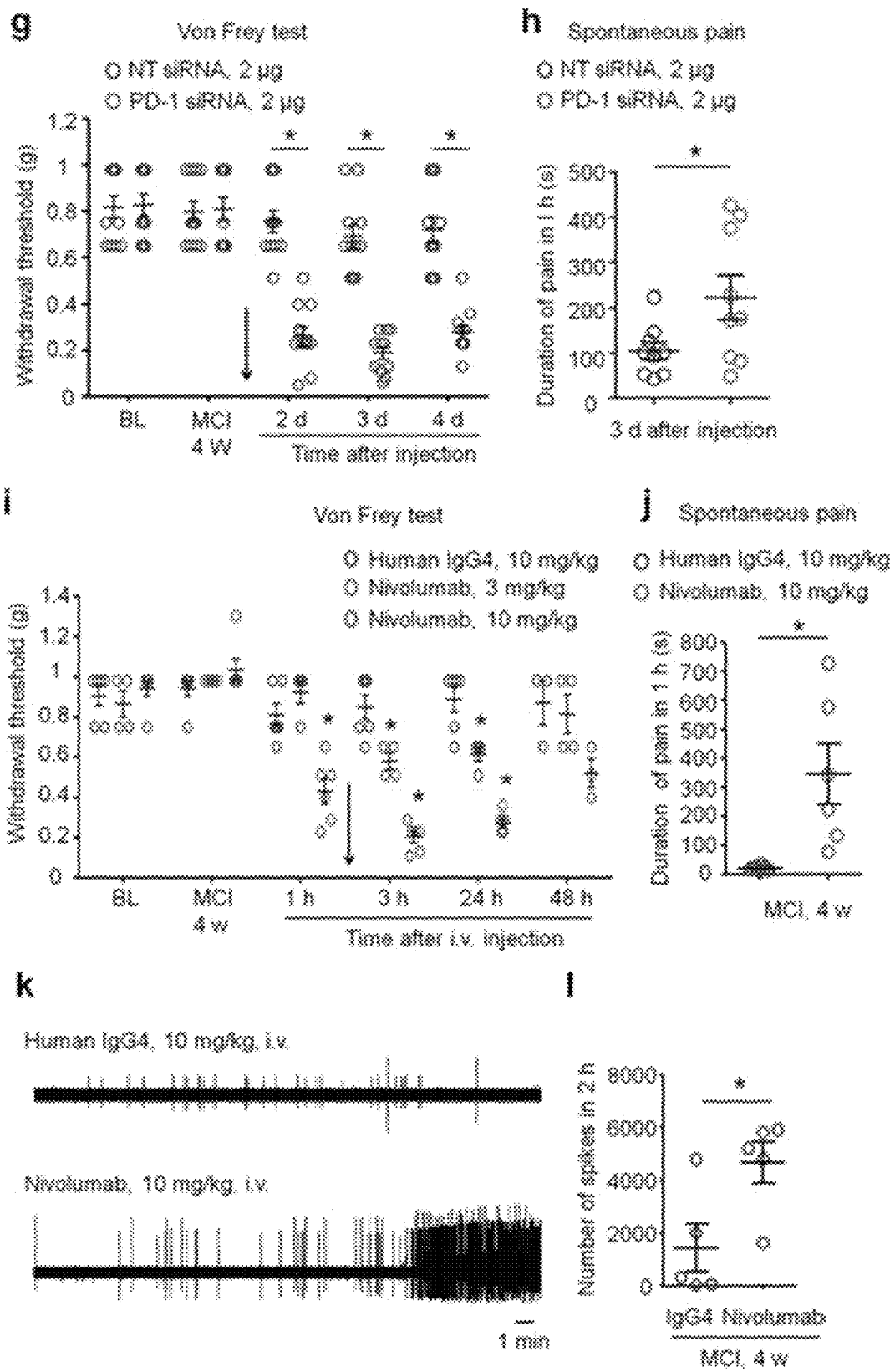
FIG. 8B(g)-(l): (g,h) Induction of mechanical allodynia (g, n=11 mice/group) and spontaneous pain (h, n=9 mice/group) by peri sciatic injection of PD-1-targeting siRNA (2 µg) but not by control non-targeting siRNA (NT, 2 µg), given at MCI-4w. *P<0.05, repeated measures Two-Way ANOVA (g) and two-tailed Student's t-test (h). (i,j) Intravenous Nivolumab (3 and 10 mg/kg), given at MCI-4w (indicated with an arrow), induces mechanical allodynia (i, n=4-6 mice/group) and spontaneous pain 3 h after injection (j, n=6 mice/group). *P<0.05, compared with control human IgG4, repeated measures Two-Way ANOVA (i) and two-tailed Student's t-test (j). (k,l) Intravenous Nivolumab (10 mg/kg, MCI-4w) increases spontaneous firing of afferent fibers in sciatic nerve 3 h after injection. (k) Traces of discharge in melanoma-bearing mice treated with Nivolumab and human IgG4 control. (l) Number of spikes in 2 hours after treatment. *P<0.05, two-tailed student's t-test, n=5 mice/group. Data expressed as mean±s.e.m.

Peri-sciatic injection of PD-1-targeting siRNA at MCI-4w induced marked and persistent mechanical allodynia for >4 days (FIG. 8B(g)) and further evoked spontaneous pain in melanoma-bearing mice (FIG. 8B(h)). Compared to non-targeting control siRNA, this Pd1-targeitng siRNA partly but significantly reduced PD-1 expression in mouse DRG and sciatic nerve but not in spinal cord tissues (P<0.05, FIG. 21A, 21B). Thus, PD-1 expressed by DRG neurons could be sufficient to mask cancer pain.

Figure 22A:
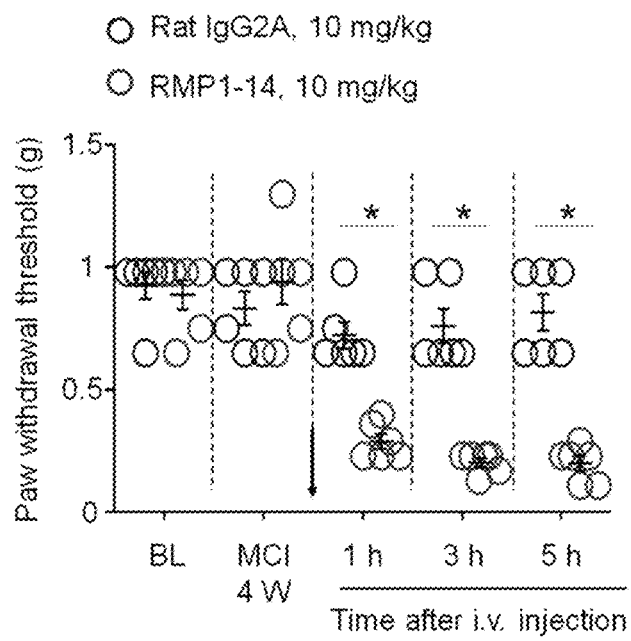
FIG. 22A(a)-(c) and FIG. 22B(d)-(f) (Supp.
Figure 22A:
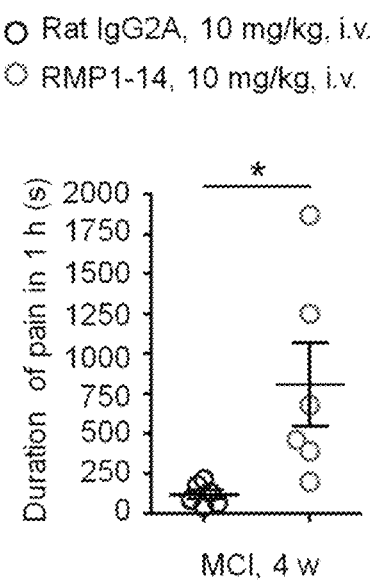
Figure 22A:
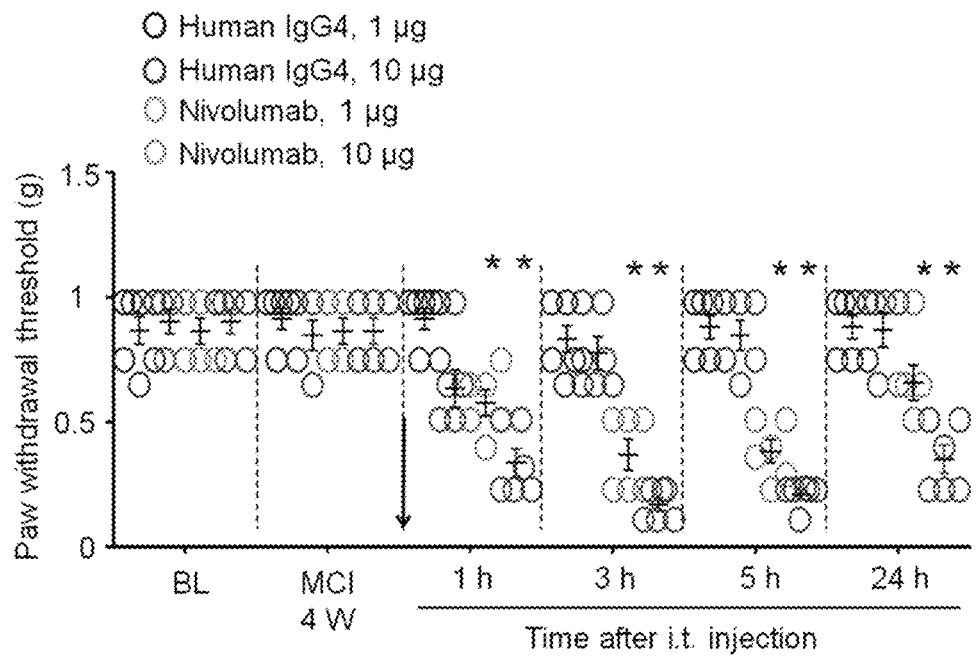
Figure 22B:
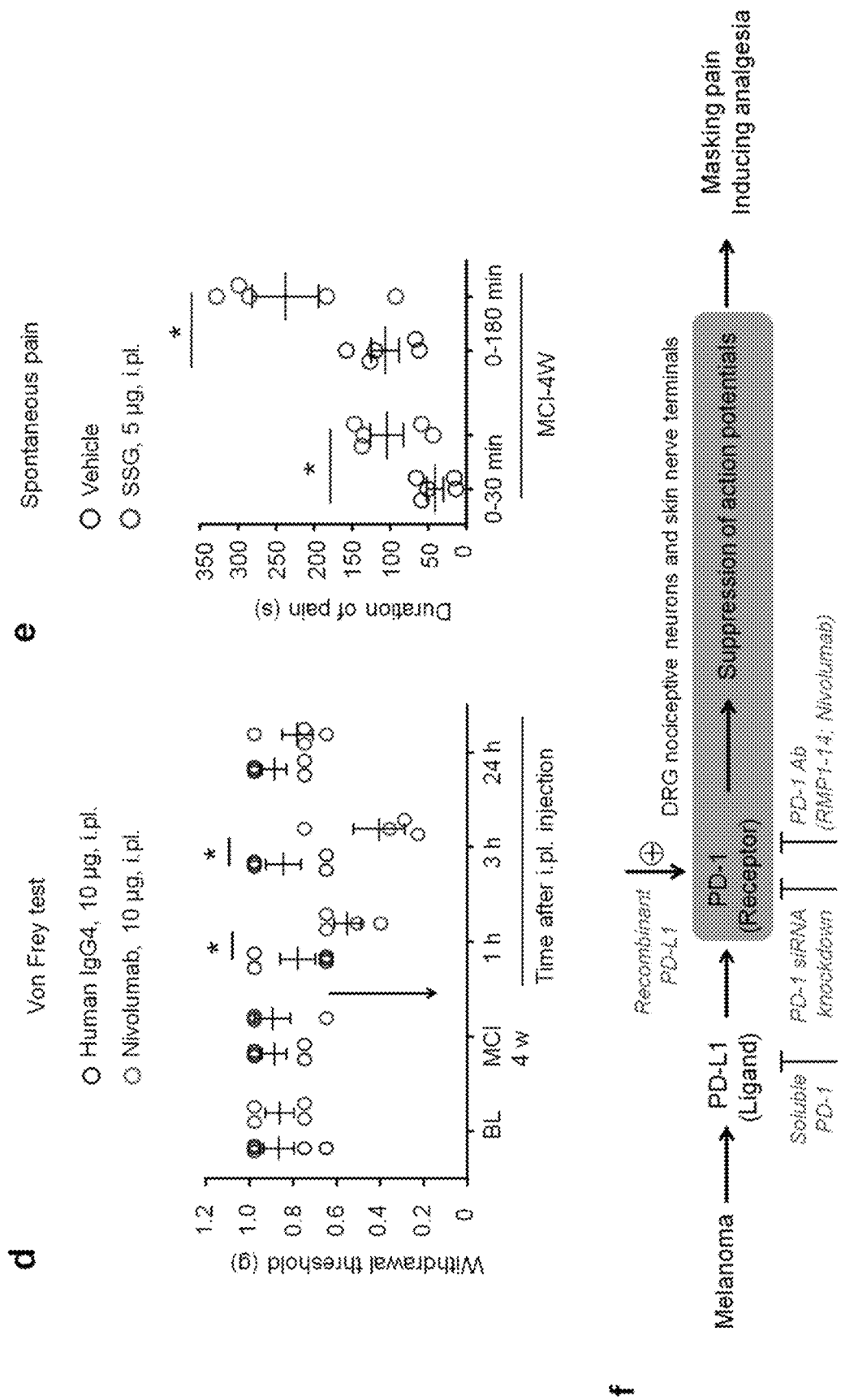
FIG. 22B(d)-(f): (d) Intraplantar injection of Nivolumab (10 µg, n=4 and 5 mice/group), given at MCI-4w (shown with the arrow), induces mechanical allodynia. *P<0.05, compared with control human IgG4, repeated measures Two-Way ANOVA. (e) Induction of spontaneous pain (flinching/licking behavior) by SHP-1 inhibitor SSG (5 µg, i.pl.) given at MCI-4w. *P<0.05, two-tailed Student's t-test. n=5 mice/group. (f) Schematic illustration of PD-L1 evoked pain masking in melanoma. Pharmacological agents used for targeting the PD-L1/PD-1 pathway are in gray. Data are mean±s.e.m.

Finally, we evaluated if anti-PD-1 antibodies would also unmask pain as sPD-1 and Pd1 siRNA in the melanoma model. Intravenous injection of Nivolumab, but not the control human IgG4 (3-10 mg/kg), caused rapid, persistent, and dose-dependent mechanical allodynia and also elicited marked spontaneous pain (FIG. 8B(i),(j)). Furthermore, RMP1-14 (10 mg/kg, i.v.), a mouse anti-PD-1 antibody, evoked remarkable spontaneous pain and mechanical allodynia (FIG. 22A(a),(b)). In vivo recordings in the mouse sciatic nerve showed that i.v. Nivolumab significantly increased spontaneous discharges in nerve fibers (FIG. 8B(k),(l)), indicating that anti-PD-1 treatment can unmask pain by increasing the excitability of primary afferent fibers. Moreover, local injection of Nivolumab via intrathecal or intraplantar route each evoked mechanical allodynia in melanoma-bearing mice (FIG. 22A(c), 22B(d)). Blocking the downstream signaling of PD-1 with SHP-1 inhibitor SSG also elicited spontaneous pain (FIG. 22B(e)). Together, these findings suggest that PD-L1 can mask pain in non-metastatic melanoma via PD-1 and SHP (FIG. 22B(f)).

Example 10. PD-L1 Potentiates Morphine Analgesia (antinociception) in a Mouse Model Animals. Pd1 (Pdcd1) knockout mice with a C57BL/6 background and C57BL/6 mice were purchased from the Jackson Laboratory (Stock No: 021157) and maintained at the Duke animal facility. Young mice (5-7 weeks of both sexes) were used for electrophysiological studies in the spinal cord and DRG neurons. Adult male mice (8-10 weeks), including knockout mice and corresponding wild-type control mice, as well as some CD1 mice, were used for behavioral and pharmacological studies. Mice were group-housed on a 12-hour light/12-hour dark cycle at 22±1° C. with free access to food and water. No statistical method was used to predetermine sample size. All the mice were randomized and applied to the animal experiments. All the animal procedures were approved by the Institutional Animal Care & Use Committee of Duke University. Animal experiments were conducted in accordance with the National Institutes of Health Guide for the Care and Use of Laboratory Animals.

Tail-flick test. All animals were habituated to testing environment for at least 2 days before baseline testing. Mice were gently held by a hand with a terry glove and with tails exposed. The distal 3 cm of the tail was immersed into the 50° C. hot water. The tail-flick latency was the time required for a mouse to flick or remove its tail out of the water. A maximum cut-off value of 15 seconds was set to avoid thermal injury. Tail-flick latency was determined both before and after drug injection. Data are expressed as the maximum possible effect (MPE) calculated as MPE (%)=100×[(post-drug response baseline response)/(cutoff response–baseline response)]. The MPE (%) data from each animal were converted to area under the curve (AUC).

Hot-plate test. All animals were habituated to testing environment for at least 2 days before baseline testing. A mouse was placed on a hot plate at 53° C. and the reaction time was scored when the animal began to exhibit signs of avoidance such as jumping or paw licking. A maximum cut-off value of 40 seconds was set to avoid tissue injury. Data are expressed as the maximum possible effect (MPE) calculated as MPE (%)=100×[(postdrug response–baseline response)/(cutoff response–baseline response)]. The MPE (%) data from each animal were converted to area under the curve (AUC).

Statistical analyses. All data were expressed as mean±s.e.m, as indicated in the figure legends. Statistical analyses were completed with Prism GraphPad 6.1. Behavioral data were analyzed using One-Way or Two-Way ANOVA followed by post-hoc Bonferroni test.

Figure 23:
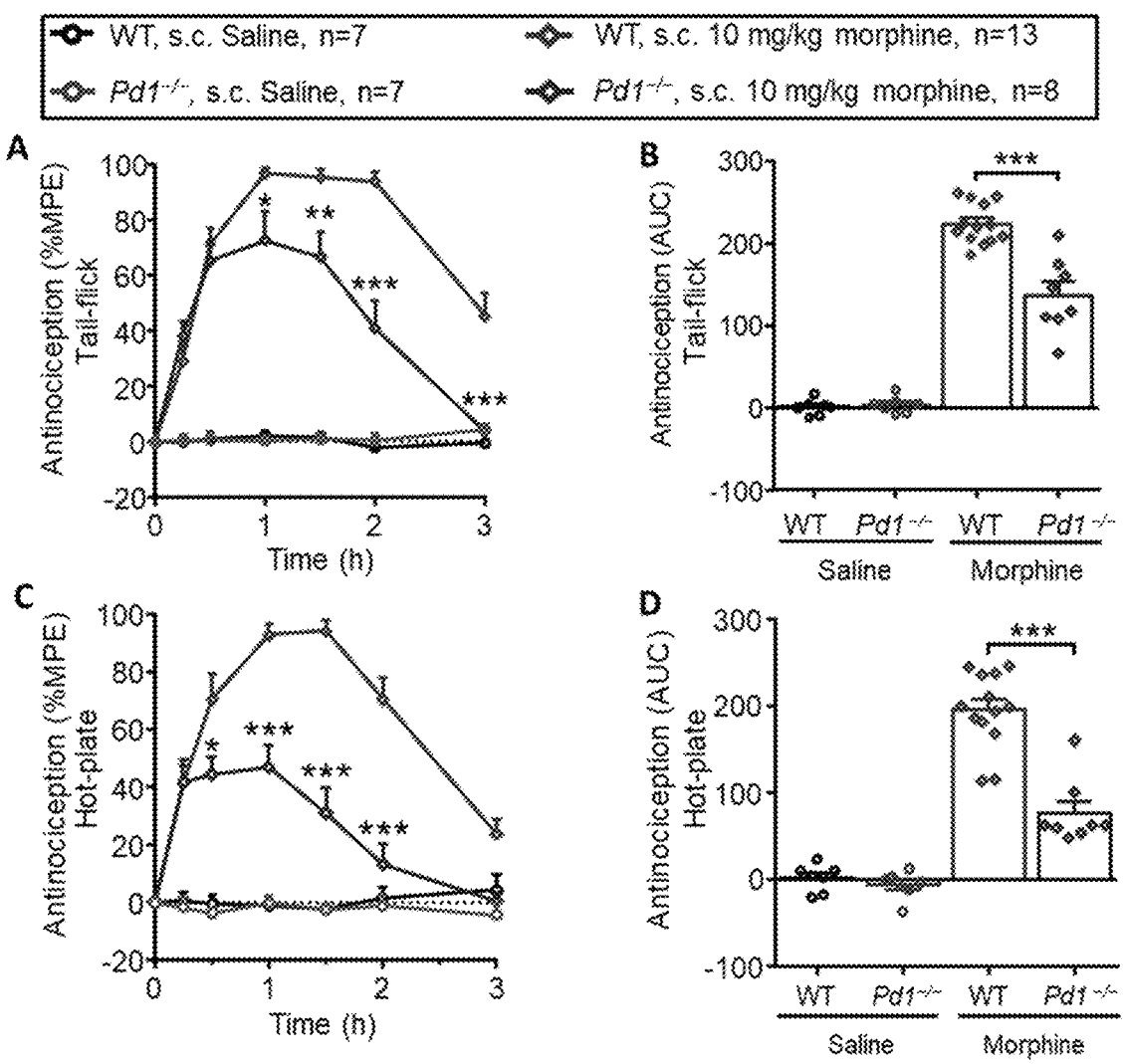
FIG. 23. Morphine analgesia (antinociception) is compromised in mice lacking Pdcd1 (Pd1n, as evaluated by tail-flick test (A,B) and hot plate test (C,D). (A) Tail-flick test showing time course of morphine antinociception, revealed as percentage of maximum possible effect (% MPE), after subcutaneous injection (s.c., 10 mg/kg). *P<0.05, P<0.01, *P<0.001, vs. WT morphine group, two-way ANOVA, followed by Bonferroni's post hoc test, n=7-13 mice per group. (B) Area under the curve (AUC) analysis of tail-flick % MPE data shown in A. ***P<0.001, one-way ANOVA, followed by Bonferroni's post hoc test. (C) Hot plate test showing time course of morphine antinociception (% MPE). *P<0.05, *P<0.001, vs. WT morphine group, two-way ANOVA, followed by Bonferroni's post hoc test, n=7-13 mice per group. (D) Area under the curve (AUC) analysis of hot-plate % MPE data shown in C. *P<0.001, one-way ANOVA, followed by Bonferroni's post hoc test.
Figure 24:
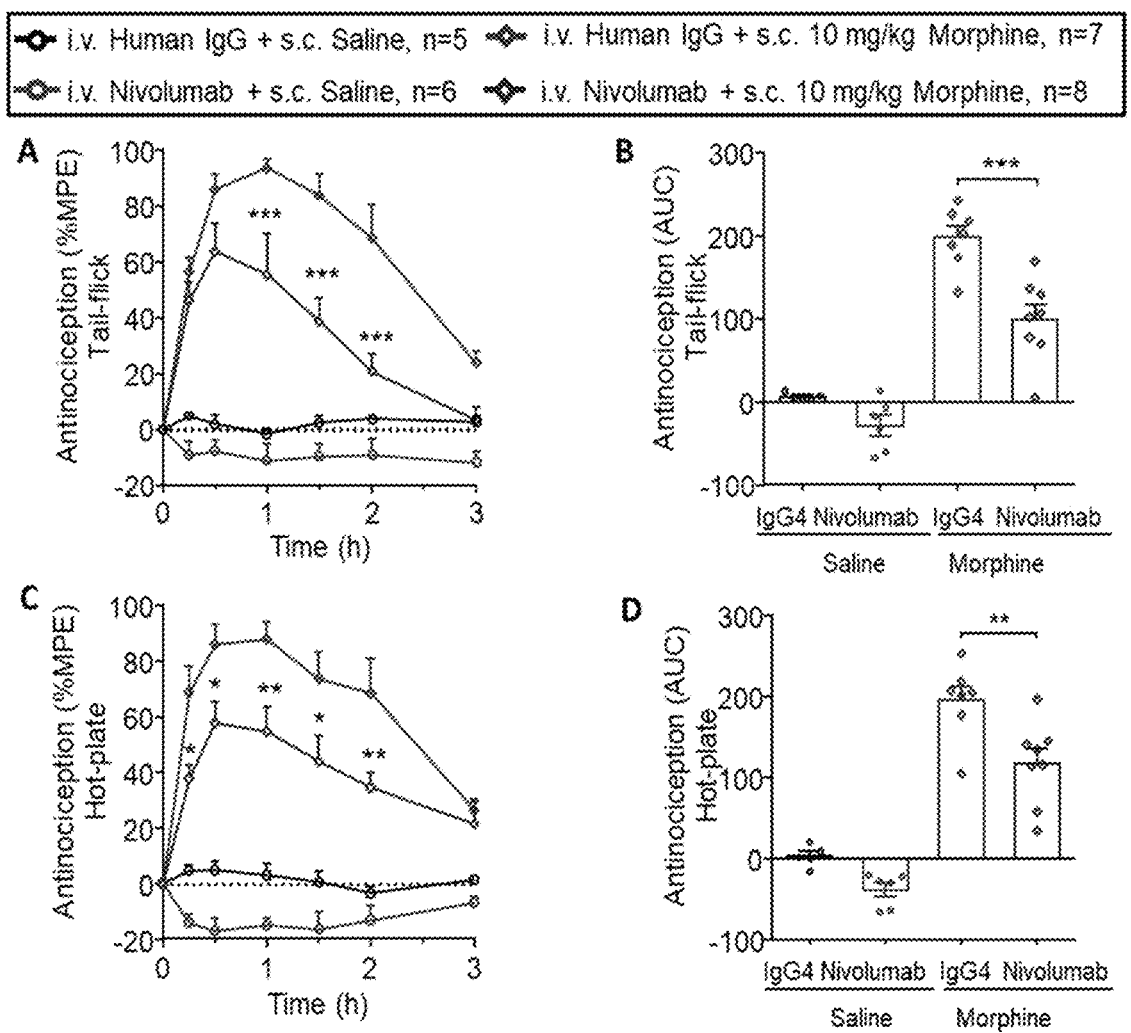
FIG. 24. Intravenous injection of the anti-PD1 antibody Nivolumab suppresses morphine's analgesic effect in tail-flick test (A,B) and hot-plate test (C,D). (A) Tail-flick test showing time course of morphine's antinociception (% MPE). *P<0.001, vs. human IgG morphine group, two-way ANOVA, followed by Bonferroni's post hoc test, n=5-8 mice per group. (B) Area under the curve (AUC) analysis of the % MPE data shown in A. *P<0.001, one-way ANOVA, followed by Bonferroni's post hoc test. (C) Hot plate test showing time course of morphine antinociception (% MPE). *P<0.05, P<0.01, vs. human IgG morphine group, two-way ANOVA, followed by Bonferroni's post hoc test, n=5-8 mice per group. (D) Area under the curve (AUC) analysis of hot-plate % MPE data shown in C. P<0.01, one-way ANOVA, followed by Bonferroni's post hoc test. Nivolumab or human IgG4 (10 mg/kg, i.v.) was injected 30 min prior to morphine injection (10 mg/kg, s.c.).
Figure 25:
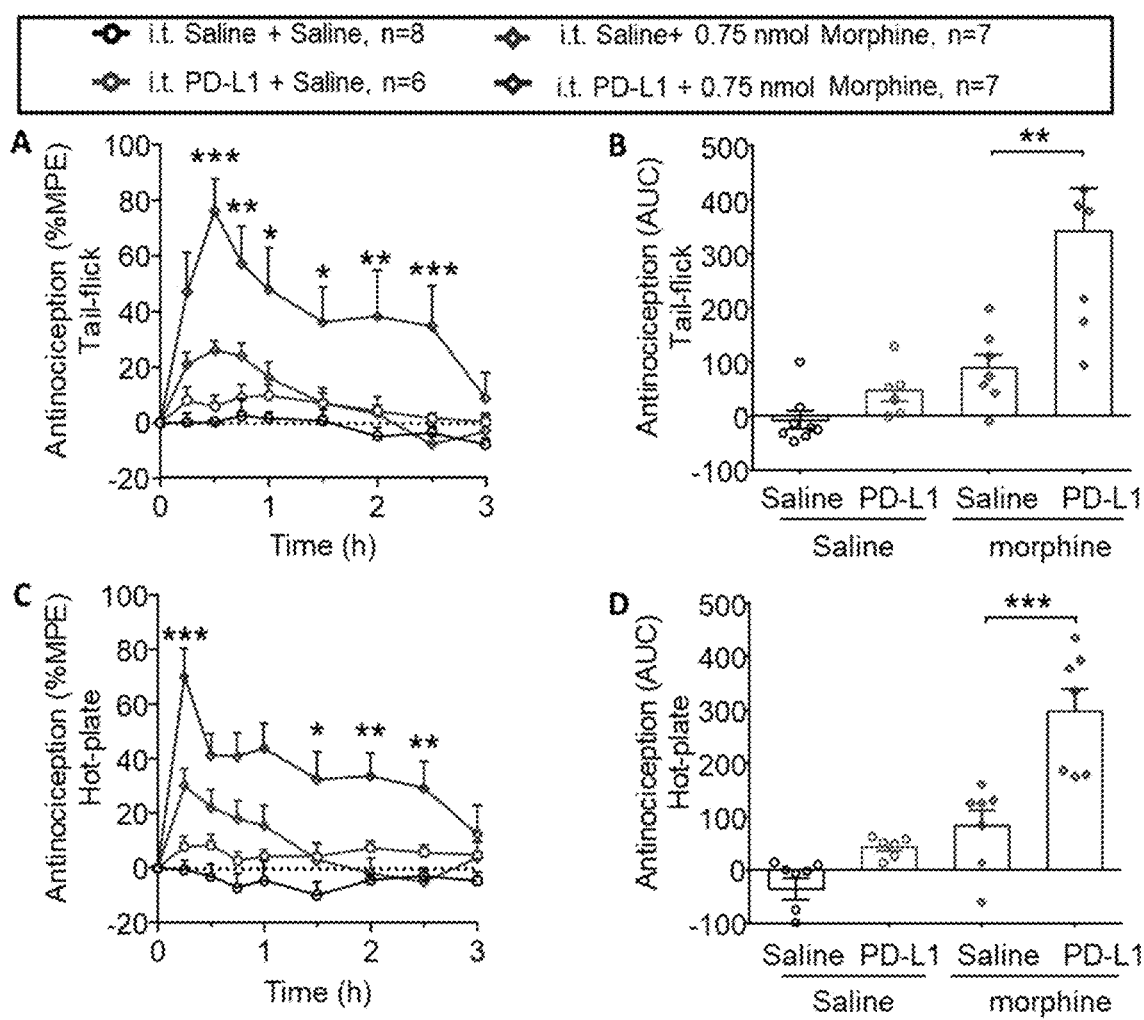
FIG. 25. PD-L1 potentiates morphine antinociception in tail-flick test (A,B) and hot plate tests (C,D). (A) Tail-flick test showing time course of spinal morphine antinociception (% MPE). *P<0.05, P<0.01, *P<0.001, vs. saline morphine group, two-way ANOVA, followed by Bonferroni's post hoc test, n=6-8 mice per group. (B) Area under the curve (AUC) analysis of tail-flick % MPE data shown in A. ***P<0.001, one-way ANOVA, followed by Bonferroni's post hoc test. (C) Hot plate test showing time course of spinal morphine antinociception (% MPE). *P<0.05, P<0.01, vs. saline morphine group, two-way ANOVA, followed by Bonferroni's post hoc test, n=6-8 mice per group. (D) Area under the curve (AUC) analysis of hot-plate % MPE data shown in C. P<0.01, one-way ANOVA, followed by Bonferroni's post hoc test. PD-L1 (3 µg) or saline was intrathecally (i.t.) injected 30 min prior to i.t. morphine injection (0.75 nmol).

The results of both the tail-flick and hot-plate tests show that subcutaneous injection of saline does not produce any analgesic effect in either wild-type (WT) mice or mice lacking PD-1 (Pd1$^{-/-}$) (FIG. 23). However, when WT and Pd1$^{-/-}$ mice receive subcutaneous injections of morphine (10 mg/kg), the Pd1$^{-/-}$ mice exhibit a reduced analgesic (antinociceptive) effect of the morphine, as compared to WT (FIG. 23). In further tests, mice were given an intravenous (i.v.) injection of either human IgG or anti-PD-1 antibody Nivolumab (10 mg/kg, i.v.) 30 minutes before subcutaneous injection with either saline (control) or morphine (10 mg/kg, s.c.) (FIG. 24). Interestingly, mice given Nivolumab and saline exhibited greater sensitivity to pain in both the tail-flick and hot-plate tests (FIG. 24). Mice that received IgG and morphine exhibited a typical analgesic effect from the morphine (FIG. 24). However, mice that received Nivolumab and morphine exhibited reduced analgesic effect from the morphine (FIG. 24). These results show that blocking PD-L1/PD-1 suppresses the analgesic effect of morphine. In view of these results, further tests were performed to confirm the effects of PD-1/PD-L1 on the analgesic effect of morphine. Mice were given intrathecal (i.t.) injections of either saline or PD-L1 (3 µg, i.t.) 30 minutes before intrathecal injection with either saline (control) or morphine (0.75 nmol, i.t.) (FIG. 25). Mice that received only saline injections did not exhibit any analgesic effects, while mice that received PD-L1 injections with saline did exhibit some analgesic effect (FIG. 25). Mice that received PD-L1 and morphine injections exhibited substantially increased analgesic effects from the morphine, when compared to mice receiving saline and morphine injections (FIG. 25). These results show that PD-L1 potentiates morphine analgesic (antinociceptive) effects, which may lead to more effective treatment of pain.

Figure 26:
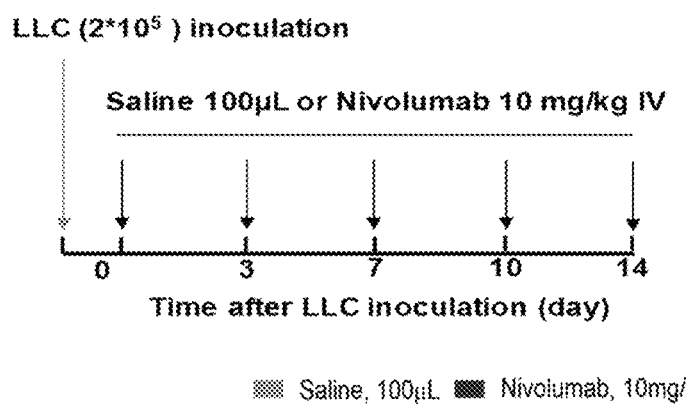
FIG. 26. Intravenous Nivolumab injections attenuate bone cancer pain following inoculation of Lewis lung cancer (LLC) cells into tibia bone cavity of mice. (A) Paradigm showing Nivolumab injections (10 mg/kg, IV) on day 0, 3, 7, 10, 14 of tumor inoculation (2,000,000 LLC cells). (B) Cancer pain, as measured by mechanical pain sensitivity (paw withdrawal threshold) in von Frey test. (C) Mechanical allodynia (paw withdrawal frequency to a subthreshold filament, 0.4 g) in von Frey test. (D) Cold allodynia (lifting and licking time) in acetone test. (E) Heat hyperalgesia (paw withdrawal latency) in Hargreaves test. (B-E) n=9-11 mice in each group; Two-way ANOVA with Bonferroni's hoc-test; *P<0.05, compared with baseline; #P<0.05, compared with Saline group.
Figure 26:
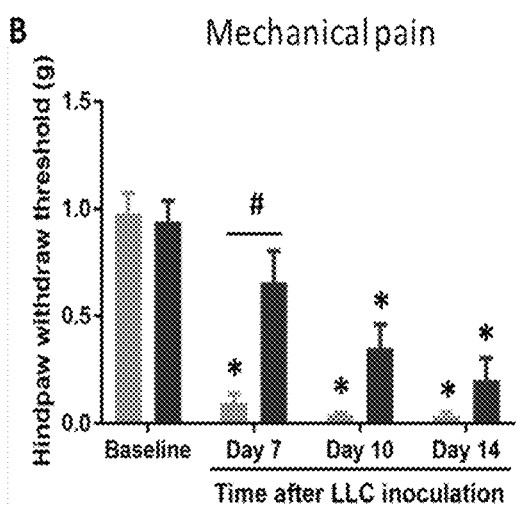
Figure 26:
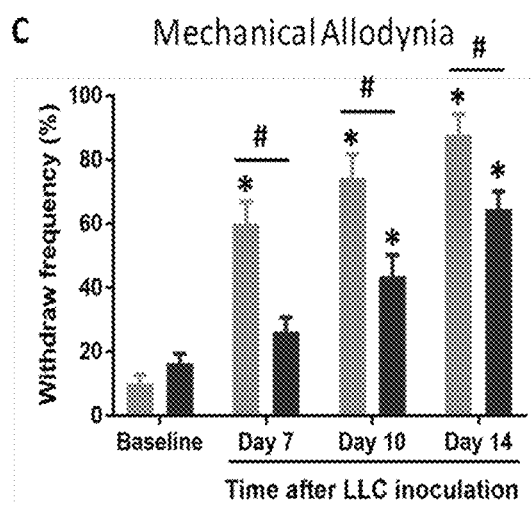
Figure 26:
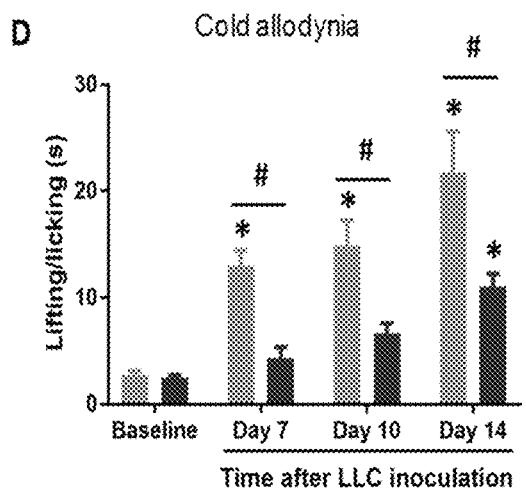
Figure 26:
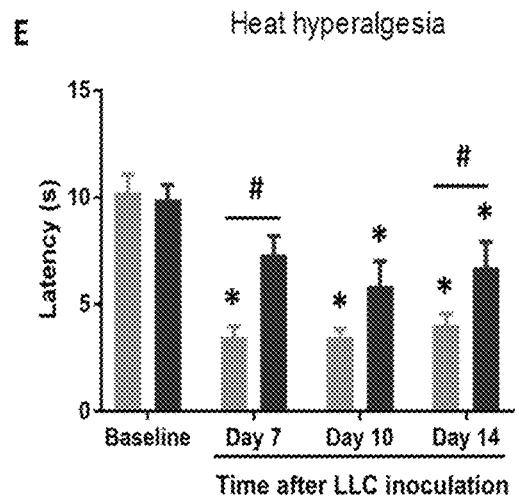
Figure 27:
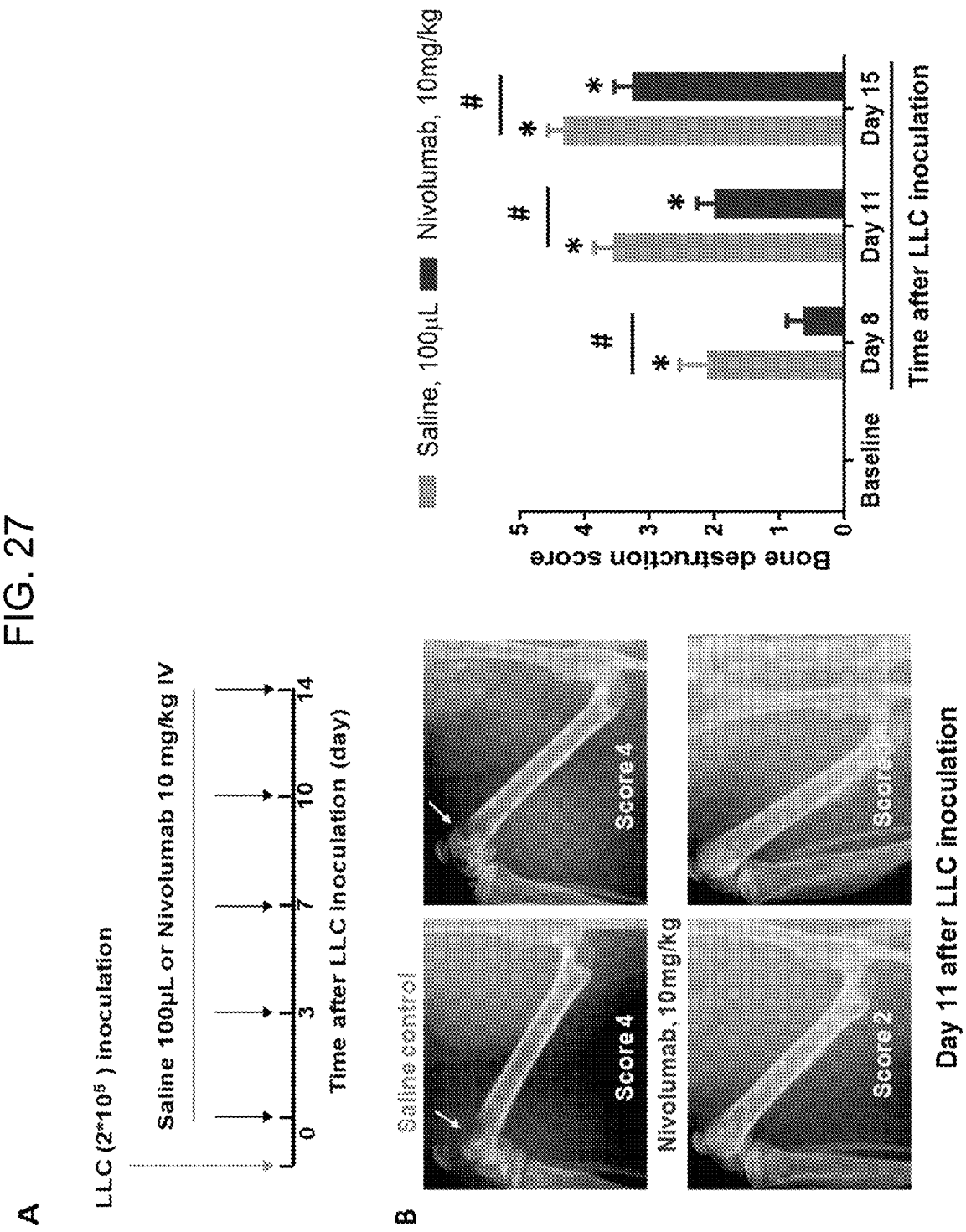
FIG. 27. Intravenous injections of Nivolumab protect against bone destruction after tumor inoculation. (A) Paradigm showing time of Nivolumab injections (10 mg/kg, IV) on day 0, 3, 7, 10, 14 of tumor inoculation (2,000,000 LLC cells). (B) X-ray images showing tibia bones 11 days after tumor inoculation. Arrows show bone destruction in saline-treated animals. (C) Bone destruction scores 8, 11, and 15 days after tumor inoculation. The scores were assessed as follows: Score 0, normal bone with no signs of destruction; Score1, small radiolucent lesions indicative of bone destruction (one to three lesions); Score 2, increased number of lesions (three to six lesions) and loss of medullary bone; Score 3, loss of medullary bone and erosion of cortical bone; Score 4, full-thickness unicortical bone loss; Score 5, full-thickness bicortical bone loss and displaced skeletal fracture. n=9-11 in each group, male, 8-10 weeks; Two-way ANOVA with Bonferroni's hoc-test; *P<0.05, compared with baseline; #P<0.05, compared with Saline group; Scores n were shown by the arrows in B.

Example 11: Anti-PD-1 Monoclonal Antibody Nivolumab Protects Against Bone Destruction and Alleviates Cancer Pain in a Mouse Model of Bone Cancer Since cancers often become painful after metastasis to bone tissue, we examined the role of PD-1 in a bone cancer pain model following inoculation of Lewis lung cancer (LLC) cells into tibia bone cavity. Intravenous injections of Nivolumab produced a rapid increase, within several hours after each injection, in mechanical and thermal pain sensitivity, due to possible activation of nociceptor terminals as we previously showed. However, Nivolumab also produced sustained beneficial effects on cancer pain relief, days after each treatment (FIG. 26). X-ray analysis revealed that tibia bone destruction during cancer progression is also protected by Nivolumab (FIG. 27). Bone destruction scores 8, 11, and 15 days after tumor inoculation were assessed as previously described (Chen, et al. *Nature Medicine,* 2000, 6(5): 521–

528): Score 0, normal bone with no signs of destruction; Score 1, small radiolucent lesions indicative of bone destruction (one to three lesions); Score 2, increased number of lesions (three to six lesions) and loss of medullary bone; Score 3, loss of medullary bone and erosion of cortical bone; Score 4, full-thickness unicortical bone loss; Score 5, full-thickness bicortical bone loss and displaced skeletal fracture. Consistently, mice lacking Pdcd1, the gene encoding PD-1, exhibited lower baseline pain thresholds, as we previously demonstrated (FIG. 23-24). However, bone cancer pain and bone destruction were also protected in these knockout (KO) mice (FIG. 27). Our findings suggest that despite transient increase in pain sensitivity, anti-PD-1 treatment may produce long-term benefits for cancer pain and bone protection due to possible suppression of tumor growth. This, anti-PD-1 monoclonal antibodies such as Nivolumab may be used to treat bone cancer pain and protect bone in cancer patients.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A method of treating a subject suffering from pain comprising administering to the subject a therapeutically effective amount of a compound capable of suppressing PD-1-associated nociceptive neuron activity such that the pain is treated, wherein the compound comprises the extracellular domain of a mature mammalian PD-L1 protein.

2. The method according to claim 1, wherein the compound is administered to the subject's dorsal root ganglia, skin, muscle, joint or cerebral spinal fluid (CSF).

3. The method according to claim 1, further comprising administering to the subject a pain reliever simultaneously or serially, wherein the PD-L1 potentiates the analgesic effect of said pain reliever.

4. The method according to claim 3, wherein the pain reliever is morphine.

5. The method according to claim 1, wherein the subject is a human.

6. A method of determining the efficacy of PD-1-associated nociceptive neuron activity suppression in a subject comprising:
   a. administering to the subject a therapeutically effective amount of a compound capable of suppressing PD-1-associated nociceptive neuron activity, wherein the compound comprises the extracellular domain of a mature mammalian PD-L1 protein; and
   b. conducting one or more quantitative sensory test(s) on the subject, wherein the one or more quantitative sensory test(s) is administered immediately after administration of the compound, and at one or more time periods after administration of the compound, wherein a rapid change in mechanical pain sensitivity after administration of the compound indicates target engagement and efficacy of the therapy.

7. The method according to claim 6, wherein the one or more time periods after administration of said compound is selected from the list consisting of 30 minutes, 45 minutes, 1 hour, 2 hours, 3 hours, 6 hours and 12 hours.

8. A method of treating pain in a subject suffering from bone cancer pain comprising administering to the subject a therapeutically effective amount of an anti-PD-1 compound.

9. The method according to claim 8, wherein the subject suffers from bone destruction.

10. The method according to claim 8, wherein the anti-PD-1 compound comprises Nivolumab, Pembrolizumab or Atezolizumab.

11. A kit for the treatment of pain in a subject comprising:
   a. a therapeutically effective amount of a compound capable of suppressing PD-1-associated nociceptive neuron activity, wherein the compound comprises the extracellular domain of a mature mammalian PD-L1 protein;
   b. an apparatus for administering said compound; and
   c. instructions for use.

* * * * *